(12) United States Patent
Kellar et al.

(10) Patent No.: US 10,820,594 B2
(45) Date of Patent: *Nov. 3, 2020

(54) STABLE INOCULANT COMPOSITIONS AND METHODS FOR PRODUCING SAME

(71) Applicant: NOVOZYMES BIOAG A/S, Bagsvaerd (DK)

(72) Inventors: Kenneth Edmund Kellar, Fuquay-Varina, NC (US); Yaowei Kang, Durham, NC (US); Claire Pelligra, Raleigh, NC (US); Emily Barnett, Bedford, VA (US); Caitlin Burklew, Salem, VA (US); Anna Wysinski, Roanoke, VA (US); Jarrod E. Leland, Blacksburg, VA (US); Ben Doughan, Salem, VA (US); Michael Harrison Fethe, Raleigh, NC (US); Ashley Delanie Trahan, Hillsborough, NC (US); David Greenshields, Saskatchewan (CA); Kristi Woods, Blacksburg, VA (US)

(73) Assignee: NOVOZYMES BIOAG A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/758,871

(22) PCT Filed: Sep. 8, 2016

(86) PCT No.: PCT/US2016/050647
§ 371 (c)(1),
(2) Date: Mar. 9, 2018

(87) PCT Pub. No.: WO2017/044545
PCT Pub. Date: Mar. 16, 2017

(65) Prior Publication Data
US 2018/0279624 A1    Oct. 4, 2018

Related U.S. Application Data

(60) Provisional application No. 62/343,250, filed on May 31, 2016, provisional application No. 62/296,766, filed on Feb. 18, 2016, provisional application No. 62/273,054, filed on Dec. 30, 2015, provisional application No. 62/217,250, filed on Sep. 11, 2015.

(51) Int. Cl.
| | | |
|---|---|---|
| *A01N 63/00* | (2020.01) | |
| *A01N 63/10* | (2020.01) | |
| *A01N 63/30* | (2020.01) | |
| *A01N 25/26* | (2006.01) | |
| *A01N 25/00* | (2006.01) | |
| *A01N 25/14* | (2006.01) | |
| *C12N 1/04* | (2006.01) | |
| *C09D 105/00* | (2006.01) | |
| *A01C 1/06* | (2006.01) | |
| *A01N 25/10* | (2006.01) | |
| *C09D 105/02* | (2006.01) | |
| *A01N 43/16* | (2006.01) | |

(52) U.S. Cl.
CPC .............. *A01N 63/00* (2013.01); *A01C 1/06* (2013.01); *A01N 25/10* (2013.01); *A01N 25/14* (2013.01); *A01N 25/26* (2013.01); *A01N 43/16* (2013.01); *A01N 63/10* (2020.01); *A01N 63/30* (2020.01); *C09D 105/00* (2013.01); *C09D 105/02* (2013.01); *C12N 1/04* (2013.01)

(58) Field of Classification Search
None
See application file for complete search history.

(56) References Cited

U.S. PATENT DOCUMENTS

| | | |
|---|---|---|
| 5,104,437 A | 4/1992 | Hadwiger |
| 5,358,863 A | 10/1994 | Quimby, Jr. |
| 5,484,464 A | 1/1996 | Gleddie |
| 5,586,411 A | 12/1996 | Gleddie |
| 5,695,541 A | 12/1997 | Kosanke |
| 5,804,208 A | 9/1998 | Andersch |
| 5,916,029 A | 6/1999 | Smith |
| 5,928,469 A | 7/1999 | Franks |
| 6,426,210 B1 | 7/2002 | Franks |
| 6,569,425 B2 | 5/2003 | Drahos |
| 6,808,917 B1 | 10/2004 | Johnson |
| 6,824,772 B2 | 11/2004 | Drahos |
| 7,429,477 B2 | 9/2008 | Johnson |
| 8,011,132 B2 | 9/2011 | Pearce |
| 8,148,138 B2 | 4/2012 | Johnson |

(Continued)

FOREIGN PATENT DOCUMENTS

| | | |
|---|---|---|
| EP | 0906951 A2 | 4/1999 |
| WO | 2009/010561 A1 | 1/2009 |

(Continued)

OTHER PUBLICATIONS

Behboudi-Jobbehdar et al, 2013, Drying Technology 31(11), 1274-1283.
Anonymous, 2013, Jumpstart LCO Extended Label, Internet website.
Oldenhof et al, 2005, Biotechnol Progr 21(3), 885-892.
Friesen et al, 2005, Appl Microbiol Biotechnol 68(3), 397-404.
Shahidi et al, 1993, Crit Rev Food Sci Nutri 33(6), 501-547.
Fu et al, 2011, Food Res Int 44(5), 1127-1149.

(Continued)

*Primary Examiner* — Alton N Pryor
(74) *Attorney, Agent, or Firm* — Adam Rucker

(57) ABSTRACT

The present disclosure provides non-aqueous inoculant compositions and methods for enhancing the survival and/or stability of microbial spores in an inoculant composition. In some embodiments, inoculant compositions of the present disclosure comprise microbial spores, one or more dispersants, one or more dust suppressants and a solid non-aqueous carrier.

15 Claims, 2 Drawing Sheets

(56) References Cited

U.S. PATENT DOCUMENTS

| | | |
|---|---|---|
| 8,278,247 B2 | 10/2012 | Hnatowich |
| 8,445,256 B2 | 5/2013 | Woods |
| 8,883,679 B2 | 11/2014 | Woods |
| 8,921,089 B2 | 12/2014 | Kang |
| 8,940,510 B2 | 1/2015 | Subramanian |
| 8,999,698 B2 | 4/2015 | Kang |
| 9,017,442 B2 | 4/2015 | Johnson |
| 9,090,884 B2 | 7/2015 | Harman |
| 9,101,088 B2 | 8/2015 | Hnatowich |
| 9,102,893 B2 | 8/2015 | Custis |
| 9,234,251 B2 | 1/2016 | Snyder |
| 9,340,464 B2 | 5/2016 | Hnatowich |
| 2002/0015988 A1 | 2/2002 | Enzmann |
| 2003/0138936 A1 | 7/2003 | Mizuguchi |
| 2004/0022860 A1 | 2/2004 | Johson |
| 2009/0142303 A1 | 6/2009 | Edwards |
| 2010/0160160 A1 | 6/2010 | Hewlett |
| 2013/0061645 A1 | 3/2013 | Smith |
| 2014/0143909 A1 | 5/2014 | Greenshields |
| 2016/0298201 A1 | 10/2016 | Siepe |

FOREIGN PATENT DOCUMENTS

| | | |
|---|---|---|
| WO | 2009/049747 A2 | 4/2009 |
| WO | 2010/037228 A1 | 4/2010 |
| WO | 2013/044214 A1 | 3/2013 |
| WO | 2013/096883 A2 | 6/2013 |
| WO | 2015/063090 A2 | 5/2015 |
| WO | 2017/044473 A1 | 3/2017 |
| WO | 2017/116837 A1 | 7/2017 |
| WO | 2017/116846 A1 | 7/2017 |

OTHER PUBLICATIONS

Colaco et al, 1992, Biotechnology 10(9), 1007-1011.
Boos et al, 1998, Microbiol Mol Biol Revs 62(1), 204-229.
Campos et al, 2014, World J Microbiol Biotechnol 30(9), 2371-2378.
Hewitt et al, 2013, Food and bioproducts processing 91, 362-369.
Ibatsam et al, 2012, African journal of food 12(3), 1-10.
Kawai et al, 2005, Pharmaceutical research 22(3), 490-495.
Mary et al, 1994, Soil Biol Biochem 26(9), 1125-1132.
Pispan et al, 2013, Food and bioproducts processing 91(4), 362-369.
Schoebitz et al, 2013, Agronomy for Sustainable Development 33(4), 751-765.
Semyonov et al, 2011, LWT-Food science and technology 44(9), 1844-1852.
Streeter, 2003, J Appl Microbiol 95(3), 484-491.

STABLE INOCULANT COMPOSITIONS AND METHODS FOR PRODUCING SAME

CROSS-REFERENCE TO RELATED APPLICATIONS

This application is a 35 U.S.C. 371 national application of international application no. PCT/US2016/050647 filed Sep. 8, 2016, which claims priority or the benefit under 35 U.S.C. 119 of U.S. provisional application Nos. 62/217,250, 62/273,054, 62/296,766 and 62/343,250 filed Sep. 11, 2015, Dec. 30, 2015, Feb. 18, 2016 and May 31, 2016, respectively, the contents of which are fully incorporated herein by reference.

FIELD OF THE INVENTION

The present disclosure relates to compositions and methods for enhancing the stability and survival of microbial spores in inoculant compositions.

BACKGROUND OF THE INVENTION

Inoculant compositions comprising agriculturally beneficial microorganisms are well known in the art. See, e.g., U.S. Pat. Nos. 5,484,464; 5,586,411; 5,695,541; 5,804,208; 5,916,029; 6,569,425; 6,808,917; 6,824,772; 7,429,477; 8,148,138; 8,278,247; 8,445,256; 8,883,679; 8,921,089; 8,999,698; 9,017,442; 9,101,088; 9,234,251; 9,340,464.

Because the effectiveness of such inoculant compositions generally depends on the ability of the microorganisms therein to survive and propagate following application, much effort has been made to increase the stability of agriculturally beneficial microorganisms in inoculant compositions. See, e.g., U.S. Pat. No. 8,011,132 (describing a method of adding trehalose, sucrose or glycerol to the substantially stationary phase of fermentation) and U.S. Pat. No. 9,090,884 (describing the microencapsulation of microorganisms in a water-soluble encapsulating material).

Nevertheless, there remains a need for improved compositions and methods for enhancing the stability and survival of microorganisms in inoculant compositions.

SUMMARY OF THE CLAIMED INVENTION

The present disclosure provides stable inoculant compositions and methods for enhancing the survival and/or stability of microbial spores in inoculant compositions.

A first aspect of the present disclosure is a non-aqueous inoculant composition comprising *Penicillium* spores, one or more dispersants and a solid non-aqueous carrier. In some embodiments, the inoculant composition comprises one or more dust suppressants, one or more pesticides, one or more lipo-chitooligosaccharides, one or more chitooligosaccharides, one or more chitinous compounds, one or more flavonoids and/or one or more drying agents.

A second aspect of the present disclosure is a coated plant propagation material comprising a plant propagation material and a coating that covers at least a portion of an outer surface of the plant propagation material, said coating comprising a non-aqueous inoculant composition of the present disclosure.

A third aspect of the present disclosure is a kit comprising a coated plant propagation material of the present disclosure and a container housing the coated plant propagation material.

A fourth aspect of the present disclosure is a plant germinated from a coated plant propagation material of the present disclosure.

A fifth aspect of the present disclosure is a plant part harvested from a plant that was germinated from a coated plant propagation material of the present disclosure.

A sixth aspect of the present disclosure is a processed product derived from a plant that was germinated from a coated plant propagation material of the present disclosure.

A seventh aspect of the present disclosure is a crop comprising a plurality of plants germinated from coated plant propagation materials of the present disclosure.

An eighth aspect of the present disclosure is a method that comprises applying a non-aqueous inoculant composition of the present disclosure to a plant propagation material.

A ninth aspect of the present disclosure is a method that comprises, consists essentially of or consisting of planting a coated plant propagation material of the present disclosure.

DETAILED DESCRIPTION

Figure 1:
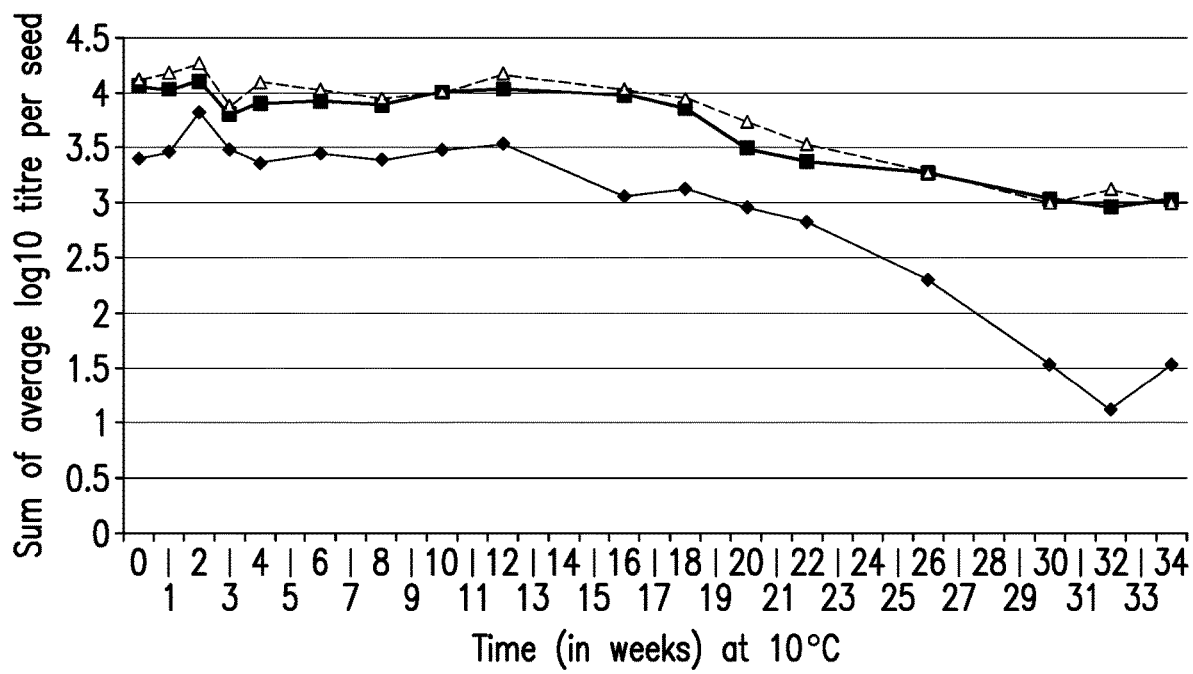
FIGS. 1-3 are graphs showing the survivability of spray-dried *Penicillium bilaiae* on corn seeds and 50% relative humidity and 10° C., 20° C. or 30° C., respectively. Triangles=corn seeds coated with a spray-dried composition comprising *Penicillium bilaiae* spores (10% w/w), MAL-TRIN QD® M580 (78.469% w/w), maltose monohydrate (8.719% w/w) and BIOSOFT® N23-3 (2.813% w/w). Squares=corn seeds coated with a spray-dried composition comprising *Penicillium bilaiae* spores (10% w/w), MAL-TRIN QD® M580 (74.879% w/w), maltose monohydrate (8.320% w/w), MULTIWET® MO-85P-PW-(AP) (2.750% w/w) and SUNSPRAY® 6N (4.051% w/w). Diamonds=corn seeds coated with a commercially available wettable powder comprising *Penicillium bilaiae* spores.

The present disclosure is explained in greater detail below. This description is not intended to be a detailed catalog of all the different ways in which the invention may be implemented or of all the features that may be added to the instant invention. For example, features illustrated with respect to one embodiment may be incorporated into other embodiments and features illustrated with respect to a particular embodiment may be deleted from that embodiment. In addition, numerous variations and additions to the various embodiments suggested herein, which do not depart from the instant invention, will be apparent to those skilled in the art in light of the instant disclosure. Hence, the following specification is intended to illustrate some particular embodiments of the invention and not to exhaustively specify all permutations, combinations and variations thereof.

The terminology used herein is for the purpose of describing particular embodiments only and is not intended to be limiting of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. For the sake of brevity and/or clarity, well-known functions or constructions may not be described in detail.

As used herein, the singular forms "a," "an," and "the" are intended to include the plural forms as well, unless the context clearly indicates otherwise. Thus, unless the context clearly indicates otherwise, "a maltodextrin" is to be interpreted as "one or more maltodextrins," "a microorganism" is to be interpreted as "one or more microorganisms," "a lipo-chitooligosaccharide" is to be interpreted as "one or more lipo-chitooligosaccharides," etc.

As used herein, the term "about," when used in reference to a measurable value such as an amount of mass, dose, time, temperature and the like, is meant to encompass variations of 0.1%, 0.25%, 0.5%, 0.75%, 1%, 2%, 3%, 4%, 5%, 6%, 7%, 8%, 9%, 10%, 11%, 12%, 13%, 14%, 15%, 16%, 17%, 18%, 19% or 20% of the specified amount. Unless otherwise indicated, all numerical values in the specification are to be understood as being modified by the term "about."

As used herein, the term "agriculturally beneficial agent" refers to any agent (e.g., chemical or biological agent) or combination of agents the application of which causes or provides a beneficial and/or useful effect in agriculture including, but not limited to, agriculturally beneficial microorganisms, biostimulants, nutrients, pesticides (e.g., fungicides, herbicides, insecticides, and nematicides) and plant signal molecules.

As used herein, the term "agriculturally beneficial microorganism" refers to a microorganism having at least one agriculturally beneficial property (e.g., the ability to fix nitrogen, the ability to solubilize phosphate and/or the ability to produce an agriculturally beneficial agent, such as a plant signal molecule).

As used herein, the term "agriculturally acceptable carrier" refers to a material that can be used to deliver an agriculturally beneficial agent to a plant, plant part or plant growth medium (e.g., soil). As used herein, the term "soil-compatible carrier" refers to a material that can be added to a soil without causing/having an unduly adverse effect on plant growth, soil structure, soil drainage, or the like. As used herein, the term "seed-compatible carrier" refers to a material that can be added to a seed without causing/having an unduly adverse effect on the seed, the plant that grows from the seed, seed germination, or the like. As used herein, the term "foliar-compatible carrier" refers to a material that can be added to a plant or plant part without causing/having an unduly adverse effect on the plant, plant part, plant growth, plant health, or the like.

As used herein, the term "and/or" is intended to include any and all combinations of one or more of the associated listed items, as well as the lack of combinations when interpreted in the alternative ("or").

As used herein, the term "aqueous" refers to a composition that contains more than a trace amount of water (i.e., more than 0.5% water by weight, based upon the total weight of the composition).

As used herein, the term "biostimulant" refers to an agent or combination of agents the application of which enhances one or more metabolic and/or physiological processes of a plant or plant part (e.g., carbohydrate biosynthesis, ion uptake, nucleic acid uptake, nutrient delivery, photosynthesis and/or respiration).

As used herein, the term "colony forming unit" refers to a microbial cell/spore capable of propagating on or in a substrate (e.g., a soil) when conditions (e.g., temperature, moisture, nutrient availability, pH, etc.) are favorable for microbial growth.

As used herein, the terms "comprise," "comprises," "comprising," "include," "includes" and "including" specify the presence of stated features, steps, operations, elements and/or components, but do not preclude the presence or addition of one or more other features, steps, operations, elements, components and/or groups thereof.

As used herein, the term "consists essentially of" (and grammatical variants thereof), as applied to the compositions and methods of the present disclosure, means that the compositions/methods may contain additional components so long as the additional components do not materially alter the composition/method. The term "materially alter," as applied to a composition/method, refers to an increase or decrease in the effectiveness of the composition/method of at least about 20% or more. For example, a component added to an inoculant composition of the present disclosure "materially alters" the composition if it increases or decreases the composition's ability to enhance microbial survival by at least about 50%.

As used herein, the terms "effective amount," "effective concentration," and "effective dosage" (and grammatical variants thereof) refer to an amount, concentration or dosage that is sufficient to cause a desired effect (e.g. enhanced microbial survival). The absolute value of the amount/concentration/dosage that is sufficient to cause the desired effect may be affected by factors such as the type and magnitude of effect desired, the type, size and volume of seeds to which the inoculant composition will be applied, the stability of the microorganisms in the inoculant composition and the storage conditions (e.g., temperature, relative humidity, duration). Those skilled in the art will understand how to select an effective amount/concentration/dosage using routine dose-response experiments.

As used herein, the term "enhanced stability" refers to an improvement in one or more characteristics of microbial stability as compared to one or more controls (e.g., a control composition that is identical to an inoculant composition of the present disclosure except that it lacks one or more of the components found in the inoculant composition of the present disclosure). Exemplary microbial stability characteristics include, but are not limited to, the ability to cause a desired effect (e.g., enhanced plant yield and/or increased pesticidal activity) after being coated on a seed and/or stored for a defined period of time and survival rate after being coated on a seed and/or stored for a defined period of time. A microorganism that exhibits improvement in one or more microbial stability characteristics as compared to a control microorganism when each is subjected to the same conditions (e.g., seed coating and storage conditions) displays enhanced stability and can be referred to as a "stable microorganism." An inoculant composition that improves one or more microbial stability characteristics of the microorganism(s) contained therein as compared to a control composition (e.g., a control composition that is identical to the inoculant composition except that it lacks one or more of the components found in the inoculant composition) provides enhanced stability and can be referred to as a "stable inoculant composition."

As used herein, the term "enhanced survival" refers to an improvement in the survival rate of one or more microorganisms in an inoculant composition as compared to one or more microorganisms in a control composition (e.g., a control composition that is identical to an inoculant composition of the present disclosure except that it lacks one or more of the components found in the inoculant composition of the present disclosure). An inoculant composition that improves the survival rate of one or more of the microorganisms contained therein as compared to a control composition (e.g., a control composition that is identical to the inoculant composition except that it lacks one or more of the components found in the inoculant composition) provides enhanced survival and can be referred to as a stable inoculant composition.

As used herein, the terms "enhanced yield" and "enhanced plant yield" refer to an improvement in one or more characteristics of plant yield as compared to one or more control plants (e.g., a control plant germinated from an untreated seed). Exemplary plant yield characteristics include, but are not limited to, biomass; bushels per acre; grain weight per plot (GWTPP); nutritional content; percentage of plants in a given area (e.g., plot) that fail to produce grain; yield at standard moisture percentage (YSMP), such as grain yield at standard moisture percentage (GYSMP); yield per plot (YPP), such as grain weight per plot (GWTPP); and yield reduction (YRED). Unless otherwise indicated, references to enhanced plant yield are to be interpreted as meaning that compositions and methods of the present disclosure may be capable of enhancing plant yield by enhancing nutrient availability, improving soil characteristics, etc. and are not to be interpreted as suggesting that compositions and methods of the present disclosure act as plant growth regulators. As used herein, the term "foliage" refers to those portions of a plant that normally grow above the ground, including, but not limited to, leaves, stalks, stems, flowers, fruiting bodies and fruits.

As used herein, the terms "foliar application," "foliarly applied" and grammatical variations thereof, refer to the application of one or more active ingredients to the foliage of a plant (e.g., to the leaves of the plant). Application may be effected by any suitable means, including, but not limited to, spraying the plant with a composition comprising the active ingredient(s). In some embodiments, the active ingredient(s) is/are applied to the leaves, stems and/or stalk of the plant and not to the flowers, fruiting bodies or fruits of the plant.

As used herein, the term "glass transition temperature" and its abbreviation "Tg" refer to the midpoint of the temperature range over which a composition transitions from a glassy state to a rubbery state.

As used herein, the term "glassy state" refers to an amorphous solid.

As used herein, the terms "inoculant composition" and "inoculum" refer to compositions comprising microbial cells and/or spores, said cells/spores being capable of propagating on or in a substrate (e.g., a soil) when conditions (e.g., temperature, moisture, nutrient availability, pH, etc.) are favorable for microbial growth.

As used herein, the term "isomer" includes all stereoisomers of the compounds and/or molecules to which it refers, including enantiomers and diastereomers, as well as all conformers, roatmers and tautomers, unless otherwise indicated. Compounds and/or molecules disclosed herein include all enantiomers in either substantially pure levorotatory or dextrorotatory form, or in a racemic mixture, or in any ratio of enantiomers. Where embodiments disclose a (D)-enantiomer, that embodiment also includes the (L)-enantiomer; where embodiments disclose a (L)-enantiomer, that embodiment also includes the (D)-enantiomer. Where embodiments disclose a (+)-enantiomer, that embodiment also includes the (−)-enantiomer; where embodiments disclose a (−)-enantiomer, that embodiment also includes the (+)-enantiomer. Where embodiments disclose a (S)-enantiomer, that embodiment also includes the (R)-enantiomer; where embodiments disclose a (R)-enantiomer, that embodiment also includes the (S)-enantiomer. Embodiments are intended to include any diastereomers of the compounds and/or molecules referred to herein in diastereomerically pure form and in the form of mixtures in all ratios. Unless stereochemistry is explicitly indicated in a chemical structure or chemical name, the chemical structure or chemical name is intended to embrace all possible stereoisomers, conformers, rotamers and tautomers of compounds and/or molecules depicted.

As used herein, the term "nitrogen fixing organism" refers to an organism capable of converting atmospheric nitrogen ($N_2$) into a form that may be utilized by a plant or plant part (e.g., ammonia ($NH_3$), ammonium ($NH_4+$), etc.).

As used herein, the term "non-aqueous" refers to a composition that comprises no more than a trace amount of water (i.e., no more than 0.5% water by weight, based upon the total weight of the composition).

As used herein, the term "nutrient" refers to a compound or element useful for nourishing a plant (e.g., vitamins, macrominerals, micronutrients, trace minerals, organic acids, etc. that are necessary for plant growth and/or development).

As used herein, the term "onset temperature" refers to the temperature at which a composition begins the transition from a glassy state to a rubbery state.

As used herein, the term "*Penicillium bilaiae*" is intended to include all iterations of the species name, such as "*Penicillium bilaji*" and "*Penicillium bilaii*."

As used herein, the term "pest" includes any organism or virus that negatively affects a plant, including, but not limited to, organisms and viruses that spread disease, damage host plants and/or compete for soil nutrients. The term "pest" encompasses organisms and viruses that are known to associate with plants and to cause a detrimental effect on the plant's health and/or vigor. Plant pests include, but are not limited to, arachnids (e.g., mites, ticks, spiders, etc.), bacteria, fungi, gastropods (e.g., slugs, snails, etc.), invasive plants (e.g., weeds), insects (e.g., white flies, *thrips*, weevils, etc.), nematodes (e.g., root-knot nematode, soybean cyst nematode, etc.), rodents and viruses (e.g., tobacco mosaic virus (TMV), tomato spotted wilt virus (TSWV), cauliflower mosaic virus (CaMV), etc.).

As used herein, the terms "pesticide" and "pesticidal" refer to agents or combinations of agents the application of which is toxic to a pest (i.e., kills a pest, inhibits the growth of a pest and/or inhibits the reproduction of a pest). Non-limiting examples of pesticides include fungicides, herbicides, insecticides, and nematicides, etc.

As used herein, the term "phosphate-solubilizing microorganism" refers to a microorganism capable of converting insoluble phosphate into a soluble form of phosphate.

As used herein, the term "plant" includes all plant populations, including, but not limited to, agricultural, horticultural and silvicultural plants. The term "plant" encompasses plants obtained by conventional plant breeding and optimization methods (e.g., marker-assisted selection) and plants obtained by genetic engineering, including cultivars protectable and not protectable by plant breeders' rights.

As used herein, the term "plant cell" refers to a cell of an intact plant, a cell taken from a plant, or a cell derived from a cell taken from a plant. Thus, the term "plant cell" includes cells within seeds, suspension cultures, embryos, meristematic regions, callus tissue, leaves, shoots, gametophytes, sporophytes, pollen and microspores.

As used herein, the term "plant part" refers to any part of a plant, including cells and tissues derived from plants. Thus, the term "plant part" may refer to any of plant components or organs (e.g., leaves, stems, roots, etc.), plant tissues, plant cells and seeds. Examples of plant parts, include, but are not limited to, anthers, embryos, flowers, fruits, fruiting bodies, leaves, ovules, pollen, rhizomes, roots, seeds, shoots, stems and tubers, as well as scions, rootstocks, protoplasts, calli and the like.

As used herein, the term "plant propagation material" refers to a plant part from which a whole plant can be generated. Examples of plant propagation materials include, but are not limited to, cuttings (e.g., leaves, stems), rhizomes, seeds, tubers and cells/tissues that can be cultured into a whole plant.

As used herein, the term "protectant" refers to an agent or combination of agents the application of which enhances the survival and/or stability of a microorganism in an inoculant composition.

As used herein, the term "rubbery state" refers to an amorphous, viscoelastic liquid.

As used herein, the terms "signal molecule" and "plant signal molecule" refer to an agent that, when applied to a plant or plant part, results in enhanced growth and/or development as compared to untreated plants or plant parts (e.g., seeds and plants harvested from untreated seeds). Non-limiting examples of signal molecules include lipo-chitooligosaccharides, chitooligosaccharides, chitinous compounds, flavonoids, jasmonic acid or derivatives thereof, linoleic acid or derivatives thereof, linolenic acid or derivatives thereof, karrikins, etc.

As used herein, the term "solid" refers to a composition that is neither a gas nor a liquid.

As used herein, the terms "spore" and "microbial spore" refer to a microorganism in its dormant, protected state.

As used herein with respect to inoculant compositions, the term "stable" refers to an inoculant composition in which microorganisms exhibit enhanced stability and/or enhanced survival. In general, an inoculant composition may be labeled "stable" if it improves the survival rate and/or at least one microbial stability characteristic of at least one microorganism contained therein.

As used herein with respect to microbial spores, the term "survival rate" refers to the percentage of microbial spores that are viable (i.e., capable of propagating on or in a substrate (e.g., on a seed and/or in a soil) when conditions (e.g., temperature, moisture, nutrient availability, pH, etc.) are favorable for microbial growth) at a given period of time.

While certain aspects of the present disclosure will hereinafter be described with reference to embodiments thereof, it will be understood by those of ordinary skill in the art that various changes in form and details may be made therein without departing from the spirit and scope of the present disclosure as defined by the claims.

All publications, patent applications, patents and other references mentioned herein are incorporated by reference in their entirety, except insofar as they contradict any disclosure expressly set forth herein.

The present disclosure provides inoculant compositions and methods for enhancing the stability and/or survival of microbial spores.

The present disclosure provides non-aqueous inoculant compositions comprising, consisting essentially of, or consisting of one or more microbial spores and a non-aqueous carrier.

In some embodiments, inoculant compositions of the present disclosure improve the stability of one or more microbial spores contained therein by at least about 0.1, 0.5, 1, 2, 3, 4, 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition (e.g., a control composition that is identical to the inoculant composition of the present disclosure except that it lacks one or more of the components found in the inoculant composition and/or contains one or more components not found in the inoculant composition of the present disclosure). For example, inoculant compositions of the present disclosure may improve one or more microbial stability characteristics of one or more of the microbial spores contained therein by at least about 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition that is identical to the inoculant composition except that lacks one or more of the protectants/dispersants found in the inoculant composition and/or comprises a reduced amount of one or more of the protectants/dispersants found in the inoculant composition.

In some embodiments, microbial spores remain viable in inoculant compositions of the present disclosure for at least 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more (e.g., at least 12, 16, 20, 24, 28, 32, 36, 40, 44, 48, 52, 56, 60, 64, 68, 72, 76, 80, 84, 88, 92, 96, 100, 104 weeks or more when stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity).

In some embodiments, inoculant compositions of the present disclosure improve the survival rate of one or more microbial spores contained therein by at least about 0.1, 0.5, 1, 2, 3, 4, 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition (e.g., a control composition that is identical to the inoculant composition of the present disclosure except that it lacks one or more of the components found in the inoculant composition and/or contains one or more components not found in the inoculant composition of the present disclosure). For example, inoculant compositions of the present disclosure may improve the survival rate of one or more of the microbial spores contained therein by at least about 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition that is identical to the inoculant composition except that lacks one or more of the protectants/dispersants found in the inoculant composition and/or comprises a reduced amount of one or more of the protectants/dispersants found in the inoculant composition.

In some embodiments, inoculant compositions of the present disclosure improve the survival of one or more of the microbial spores contained therein to the extent that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the microbial spores survive when the inoculant composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more. In some embodiments, inoculant compositions of the present disclosure improve the survival of one or more of the microbial spores contained therein to the extent that at least about 5, 6, 7, 8, 9, 10, 11, 12, 13, 14, 15, 16, 17, 18, 19, 20, 25, 30, 35, 40, 45, 50, 55, 60, 65, 70% or more of the microbial spores survive when the inoculant composition is stored at 20, 21, 22, 23, 24, 25, 26, 27, 28, 29 and/or 30° C. for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure improve the survival of one or more of the microbial spores contained therein to the extent that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the microbial spores survive when the inoculant composition is desiccated by about 5, 10, 15, 20, 25, 30, 35, 40, 45, 50, 55, 60, 65, 70, 75, 80, 85, 90, 95% or more and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more. In some embodiments, inoculant compositions of the present disclosure improve the survival of one or more of the microbial spores contained therein to the extent that at least about 5, 6, 7, 8, 9, 10, 11, 12, 13, 14, 15, 16, 17, 18, 19, 20, 25, 30, 35, 40, 45, 50, 55, 60, 65, 70% or more of the microbial spores survive when the inoculant composition is coated on a seed, dried and stored at 20, 21, 22, 23, 24, 25, 26, 27, 28, 29 and/or 30° C. and 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure improve the survival of one or more of the microbial spores contained therein to the extent that at least $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$ cfu/gram or milliliter or more of the microbial spores survive when the inoculant composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more. In some embodiments, inoculant compositions of the present disclosure improve the survival of one or more of the microbial spores contained therein to the extent that at least $1 \times 10^4$, $1 \times 10^5$, $1 \times 10^6$, $1 \times 10^7$ cfu/seed or more of the microbial spores survive when the inoculant composition is stored at 20, 21, 22, 23, 24, 25, 26, 27, 28, 29 and/or 30° for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure improve the survival of one or more of the microbial spores contained therein to the extent that at least $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$ cfu/gram or milliliter or more of the microbial spores survive when the inoculant composition is desiccated by about 5, 10, 15, 20, 25, 30, 35, 40, 45, 50, 55, 60, 65, 70, 75, 80, 85, 90, 95% or more and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more. In some embodiments, inoculant compositions of the present disclosure improve the survival of one or more of the microbial spores contained therein to the extent that at least $1 \times 10^4$, $1 \times 10^5$, $1 \times 10^6$, $1 \times 10^7$ cfu/seed or more of the microbial spores survive when the inoculant composition is coated on a seed, dried and stored at 20, 21, 22, 23, 24, 25, 26, 27, 28, 29 and/or 30° C. and 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure improve both the survival rate and one, two, three, four, five, six, seven, eight, nine, ten or more microbial stability characteristics of the microbial spore(s) contained therein.

In some embodiments, inoculant compositions of the present disclosure improve the dispersion of one or more microbial spores contained therein by at least about 0.1, 0.5, 1, 2, 3, 4, 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition (e.g., a control composition that is identical to the inoculant composition of the present disclosure except that it lacks one or more of the components found in the inoculant composition and/or contains one or more components not found in the inoculant composition of the present disclosure). For example, inoculant compositions of the present disclosure may improve the dispersion of one or more of the microbial spores contained therein by at least about 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition that is identical to the inoculant composition except that lacks one or more of the protectants/dispersants found in the inoculant composition and/or comprises a reduced amount of one or more of the protectants/dispersants found in the inoculant composition.

In some embodiments, inoculant compositions of the present disclosure improve the dispersion of one or more of the microbial spores contained therein to the extent that at least about 50, 55, 60, 65, 70, 75, 80, 85, 90, 95% or more of the microbial spores are present as single spores (rather than as members of a clump comprising two or more microbial spores).

Inoculant compositions of the present disclosure may be used to improve any suitable microbial stability characteristic(s), including, but not limited to, the ability of microbial spores therein to enhance plant yield after being coated on a seed and stored for a defined period of time prior to planting the seed. For example, in some embodiments, inoculant compositions of the present disclosure improve the ability of the microbial spores therein to propagate and increase yield after being coated on a plant propagation material (e.g., seed) and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

Inoculant compositions of the present disclosure may comprise any suitable spores(s), including, but not limited to, the spores of agriculturally beneficial microorganisms such as diazotrophs, phosphate-solubilizing microorganisms and biopesticides.

In some embodiments, inoculant compositions of the present disclosure comprise spores from one or more Gram-negative bacteria.

In some embodiments, inoculant compositions of the present disclosure comprise spores from one or more Gram-positive bacteria.

Non-limiting examples of bacterial spores that may be useful in compositions of the present disclosure include spores of *Bacillus amyloliquefaciens* D747, *Bacillus amyloliquefaciens* NRRL B-50349, *Bacillus amyloliquefaciens* TJ1000, *Bacillus amyloliquefaciens* FZB24, *Bacillus amyloliquefaciens* FZB42, *Bacillus amyloliquefaciens* IN937a, *Bacillus amyloliquefaciens* IT-45, *Bacillus amyloliquefaciens* TJ1000, *Bacillus amyloliquefaciens* MBI600, *Bacillus amyloliquefaciens* BS27 (deposited as NRRL B-5015), *Bacillus amyloliquefaciens* BS2084 (deposited as NRRL B-50013), *Bacillus amyloliquefaciens* 15AP4 (deposited as ATCC PTA-6507), *Bacillus amyloliquefaciens* 3AP4 (deposited as ATCC PTA-6506), *Bacillus amyloliquefaciens* LSSA01 (deposited as NRRL B-50104), *Bacillus amyloliquefaciens* ABP278 (deposited as NRRL B-50634), *Bacillus amyloliquefaciens* 1013 (deposited as NRRL B-50509), *Bacillus amyloliquefaciens* 918 (deposited as NRRL B-50508), *Bacillus amyloliquefaciens* 22CP1 (deposited as ATCC PTA-6508) and *Bacillus amyloliquefaciens* BS18 (deposited as NRRL B-50633), *Bacillus cereus* 1-1562, *Bacillus firmus* 1-1582, *Bacillus* lichenformis BA842 (deposited as NRRL B-50516), *Bacillus* lichenformis BL21 (deposited as NRRL B-50134), *Bacillus mycoides* NRRL B-21664, *Bacillus pumilus* NRRL B-21662, *Bacillus pumilus* NRRL B-30087, *Bacillus pumilus* ATCC 55608, *Bacillus pumilus* ATCC 55609, *Bacillus pumilus* GB34, *Bacillus pumilus* KFP9F, *Bacillus pumilus* QST 2808, *Bacillus subtilis* ATCC 55078, *Bacillus subtilis* ATCC 55079, *Bacillus subtilis* MBI 600, *Bacillus subtilis* NRRL B-21661, *Bacillus subtilis* NRRL B-21665, *Bacillus subtilis* CX-9060, *Bacillus subtilis* GB03, *Bacillus subtilis* GB07, *Bacillus subtilis* QST-713, *Bacillus subtilis* FZB24, *Bacillus subtilis* D747, *Bacillus subtilis* 3BP5 (deposited as NRRL B-50510), *Bacillus thuringiensis* ATCC 13367, *Bacillus thuringiensis* GC-91, *Bacillus thuringiensis* NRRL B-21619, *Bacillus thuringiensis* ABTS-1857, *Bacillus thuringiensis* SAN 401 I, *Bacillus thuringiensis* ABG-6305, *Bacillus thuringiensis* ABG-6346, *Bacillus thuringiensis* AM65-52, *Bacillus thuringiensis* SA-12, *Bacillus thuringiensis* SB4, *Bacillus thuringiensis* ABTS-351, *Bacillus thuringiensis* HD-1, *Bacillus thuringiensis* EG 2348, *Bacillus thuringiensis* EG 7826, *Bacillus thuringiensis* EG 7841, *Bacillus thuringiensis* DSM 2803, *Bacillus thuringiensis* NB-125, *Bacillus thuringiensis* NB-176 and combinations thereof, as well as spores of microorganisms having at least at least 75%, 80%, 85%, 90%, 95%, 96%, 97%, 98%, 99% or more identical to any of the aforementioned strains on the basis of 16S rDNA sequence identity.

In some embodiments, inoculant compositions of the present disclosure comprise one or more fungal spores.

Non-limiting examples of fungal spores that may be useful in compositions of the present disclosure include spores of *Gliocladium virens* ATCC 52045, *Gliocladium virens* GL-21, *Glomus infraradices* RTI-801, *Metarhizium anisopliae* F52, *Penicillium bilaiae* (formerly known as *P. bilaii* and *P. bilaji*) ATCC 18309, *Penicillium bilaiae* ATCC 20851, *Penicillium bilaiae* ATCC 22348, *Penicillium bilaiae* NRRL 50162, *Penicillium bilaiae* NRRL 50169, *Penicillium bilaiae* NRRL 50776, *Penicillium bilaiae* NRRL 50777, *Penicillium bilaiae* NRRL 50778, *Penicillium bilaiae* NRRL 50777, *Penicillium bilaiae* NRRL 50778, *Penicillium bilaiae* NRRL 50779, *Penicillium bilaiae* NRRL 50780, *Penicillium bilaiae* NRRL 50781, *Penicillium bilaiae* NRRL 50782, *Penicillium bilaiae* NRRL 50783, *Penicillium bilaiae* NRRL 50784, *Penicillium bilaiae* NRRL 50785, *Penicillium bilaiae* NRRL 50786, *Penicillium bilaiae* NRRL 50787, *Penicillium bilaiae* NRRL 50788, *Penicillium bilaiae* RS7B-SD1, *Penicillium brevicompactum* AgRF18, *Penicillium canescens* ATCC 10419, *Penicillium expansum* ATCC 24692, *Penicillium expansum* YT02, *Penicillium* fellatanum ATCC 48694, *Penicillium gaestrivorus* NRRL 50170, *Penicillium glabrum* DAOM 239074, *Penicillium glabrum* CBS 229.28, *Penicillium janthinellum* ATCC 10455, *Penicillium lanosocoeruleum* ATCC 48919, *Penicillium radicum* ATCC 201836, *Penicillium radicum* FRR 4717, *Penicillium radicum* FRR 4719, *Penicillium radicum* N93/47267, *Penicillium raistrickii* ATCC 10490, *Trichoderma asperellum* SKT-1, *Trichoderma asperellum* ICC 012, *Trichoderma atroviride* LC52, *Trichoderma atroviride* CNCM 1-1237, *Trichoderma fertile* JM41R, *Trichoderma gamsii* ICC 080, *Trichoderma hamatum* ATCC 52198, *Trichoderma harzianum* ATCC 52445, *Trichoderma harzianum* KRL-AG2, *Trichoderma harzianum* T-22, *Trichoderma harzianum* TH-35, *Trichoderma harzianum* T-39, *Trichoderma harzianum* ICC012, *Trichoderma reesi* ATCC 28217, *Trichoderma virens* ATCC 57678, *Trichoderma virens* G1-3, *Trichoderma virens* GL-21, *Trichoderma virens* G-41, *Trichoderma viridae* ATCC 52440, *Trichoderma viridae* ICC080, *Trichoderma viridae* TV1 and combinations thereof, as well as spores of microorganisms having at least at least 75%, 80%, 85%, 90%, 95%, 96%, 97%, 98%, 99% or more identical to any of the aforementioned strains on the basis of internal transcribed spacer (ITS) and/or cytochrome c oxidase (CO1) sequence identity.

In some embodiments, inoculant compositions of the present disclosure comprise spores from one or more mycorrhizal fungi (e.g., one or more endomycorrhizal fungi and/or one or more ectomycorrhizal fungi).

Non-limiting examples of mycorrhizal spores that may be useful in compositions of the present disclosure includes pores of mycorrhizal strains such as *Gigaspora margarita*, *Glomus aggregatum*, *Glomus brasilianum*, *Glomus clarum*, *Glomus deserticola*, *Glomus etunicatum*, *Glomus intraradices*, *Glomus monosporum*, *Glomus mosseae*, *Laccaria bicolor*, *Laccaria laccata*, *Paraglomus brazilianum*, *Pisolithus tinctorius*, *Rhizopogon amylopogon*, *Rhizopogon fulvigleba*, *Rhizopogon luteolus*, *Rhizopogon villosuli*, *Scleroderma cepa* and *Scleroderma cifrinum* and combinations thereof.

In some embodiments, inoculant compositions of the present disclosure comprise spores from one or more diazotrophs.

In some embodiments, inoculant compositions of the present disclosure comprise spores from one or more phosphate-solubilizing microorganisms.

In some embodiments, inoculant compositions of the present disclosure comprise spores from one or more biofungicides, bioherbicides, bioinsectides and/or bionematicides. See generally Burges, Formulation of Microbial Biopesticides: Beneficial Microorganisms, Nematodes and Seed Treatments (Springer Science & Business Media) (2012); Hall & Menn, Biopesticides: Use and Delivery (Humana Press) (1998); McCoy, et al., *Entomogenous fungi*, in CRC Handbook of Natural Pesticides. Microbial Pesticides, Part A. ENTOMOGENOUS PROTOZOA AND FUNGI (C. M. Inoffo, ed.), Vol. 5:151-236 (1988); SAMSON, et al., ATLAS OF ENTOMOPATHOGENIC FUNGI (Springer-Verlag, Berlin) (1988); and deFaria and Wraight, *Mycoinsecticides and Mycoacaricides: A comprehensive list with worldwide coverage and international classification of formulation types*, BIOL. CONTROL (2007), doi: 10.1016/j.biocontrol.2007.08.001.

Microbial spores may be incorporated into inoculant compositions of the present disclosure in any suitable amount(s)/concentration(s).

In some embodiments, microbial spores comprise about 0.1 to about 30% (by weight) of the inoculant composition. For example, inoculant compositions of the present disclosure may comprise about 0.1, 0.2, 0.3, 0.4, 0.5, 0.6, 0.7, 0.8, 0.9, 1, 1.25, 1.5, 1.75, 2, 2.25, 2.5, 2.75, 3, 3.25, 3.5, 3.75, 4, 4.25, 4.5, 4.75, 5, 6, 7, 8, 9, 10, 11, 12, 13, 14, 15, 16, 17, 18, 19, 20, 21, 22, 23, 24, 25, 26, 27, 28, 29, 30% or more (by weight) of one or more microbial spores. In some embodiments, the microbial spore amount/concentration is about 1, 2, 3, 4 or 5 to about 5, 6, 7, 8, 9, 10, 11, 12, 13, 14, 15, 16, 17, 18, 19, 20, 21, 22, 23, 24 or 25% (by weight) of the inoculant composition.

In some embodiments, microbial spores are present in an amount ranging from about $1\times10^1$ to about $1\times10^{20}$ colony-forming units (cfu) per gram and/or milliliter of inoculant composition. For example, inoculant compositions of the present disclosure may comprise about $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ or more microbial spores per gram and/or milliliter of inoculant composition (e.g., about $1\times10^4$ to about $1\times10^9$ *Bacillus amyloliquefaciens* TJ1000 (also known as 1BE, isolate ATCC BAA-390), *Metarhizium anisopliae* F52, *Penicillium bilaiae* ATCC 20851, *Penicillium bilaiae* RS7B-SD1 and/or *Trichoderma virens* G1-3 spores per gram/milliliter).

In some embodiments, the amount/concentration of spores is that amount/concentration which is effective to enhance the yield of the plant or plant part to which the inoculant composition is applied.

Microbial spores may be produced by any suitable method(s), including, but not limited to, liquid fermentation and solid state fermentation. See, e.g., Cunningham et al., CAN. J. BOT. 68:2270 (1990); Friesen et al., APPL. MICROBIOL. BIOTECH. 68:397 (2005).

Although the primary foci of the present disclosure are compositions and methods for enhancing the stability and/or survival of microbial spores, it is to be understood that inoculant compositions of the present disclosure may comprise one or more microorganisms (e.g., diazotrophs, phosphate-solubilizing microorganisms and/or biopesticides) in a vegetative state. See International Patent Application No. PCT/US2016/050529, the disclosure of each of which is incorporated herein by reference in its entirety.

Vegetative cells may be incorporated into inoculant compositions of the present disclosure in any suitable amount(s)/concentration(s). In some embodiments, inoculant compositions of the present disclosure are devoid of vegetative cells.

In some embodiments, vegetative cells are present in an amount ranging from about $1\times10^1$ to about $1\times10^{20}$ colony-forming units (cfu) per gram and/or milliliter of inoculant composition. For example, inoculant compositions of the present disclosure may comprise about $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ or more cfu of agriculturally beneficial microorganisms per gram and/or milliliter of inoculant composition.

In some embodiments, the amount/concentration of vegetative cells is an amount effective to enhance the yield of the plant or plant part to which the inoculant composition is applied.

In some embodiments, the amount/concentration of vegetative cells is $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ or more cfu per gram/milliliter of inoculant composition.

Inoculant compositions of the present disclosure may comprise any suitable non-aqueous carrier(s), including, but not limited to, foliar-compatible carriers, seed-compatible carriers and soil-compatible carriers. Selection of appropriate carrier materials will depend on the intended application(s) and the microorganism(s) present in the inoculant composition.

In some embodiments, the carrier material(s) are selected to provide an inoculant composition in the form of a powder or granuale. For example, carrier materials may be selected to provide inoculant compositions that are formulated as freeze-dried powders, spray-dried powders, spray-freeze-dried powders and combinations thereof.

Non-limiting examples of solid carriers that may be useful in compositions of the present disclosure include disaccharides, maltodextrins, monosaccharides, oligosaccharides, peat-based powders and granuales, and agriculturally acceptable polymers.

Additional examples of solid carriers that may be included in inoculant compositions of the present disclosure may be found in BURGES, FORMULATION OF MICROBIAL BIOPESTICIDES: BENEFICIAL MICROORGANISMS, NEMATODES AND SEED TREATMENTS (Springer Science & Business Media) (2012).

Carriers incorporated into inoculant compositions of the present disclosure may comprise a growth medium suitable for culturing one or more of the microorganisms in the inoculant composition. For example, in some embodiments, inoculant compositions of the present disclosure comprise Czapek-Dox medium, glycerol yeast extract, mannitol yeast extract, potato dextrose broth and/or YEM media.

The non-aqueous carrier may constitute any suitable portion of the inoculant composition. In some embodiments, the non-aqueous carrier(s) comprise(s) about 1 to about 99% (by weight) of the inoculant composition. For example, inoculant compositions of the present disclosure, the non-aqueous carrier(s) constitute(s) about 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, 99.5% or more (by weight) of the inoculant composition. In some embodiments, the carrier amount/concentration is about 50 to about 99%, about 55% to about 95%, about 60% to about 95%, about 65% to about 90%, about 70 to about 90%, about 75 to about 90%, about 80 to about 90% or about 80 to about 85% (by weight) of the inoculant composition. In some embodiments, inoculant compositions of the present disclosure comprise one or more commercial carriers used in accordance with the manufacturer's recommended amounts/concentrations.

In some embodiments, the non-aqueous carrier comprises, consists essentially of, or consists of one or more maltodextrins.

Inoculant compositions of the present disclosure may comprise any suitable maltodextrins, including, but not limited to, maltodextrins having a dextrose equivalent value (DEV) of about 3, 4, 5, 6, 7, 8, 9, 10, 11, 12, 13, 14, 15, 16, 17, 18, 19, 20, 21, 22, 23, 24, or 25. In some embodiments, inoculant compositions of the present disclosure comprise one or more maltodextrins having a DEV of about 5 to about 6, 7, 8, 9, 10, 11, 12, 14, 15, 16, 17, 18, 19, 20, 21, 22, 23, 24, or 25, about 10 to about 11, 12, 14, 15, 16, 17, 18, 19, 20, 21, 22, 23, 24, or 25, or about 15 to about 16, 17, 18, 19, 20, 21, 22, 23, 24, or 25. In some embodiments, the non-aqueous carrier comprises a combination of maltodextrins having a DEV of about 5 to about 6, 7, 8, 9, 10, 11, 12, 14, 15, 16, 17, 18, 19, 20, 21, 22, 23, 24, or 25, about 10 to about 11, 12, 14, 15, 16, 17, 18, 19, 20, 21, 22, 23, 24, or 25, or about 15 to about 16, 17, 18, 19, 20, 21, 22, 23, 24, or 25. In some embodiments, the non-aqueous carrier comprises one or more maltodextrins having a DEV of about 10 to about 25 (e.g., one or more maltodextrins having a DEV of about 15 to about 20). In some embodiments, the non-aqueous carrier comprises a combination of maltodextrins having a DEV of about 10 to about 25 (e.g., a combination of maltodextrins having a DEV of about 15 to about 20).

Non-limiting examples of maltodextrins that may be useful in compositions of the present disclosure include MALTRIN® M150 (DEV=15; molecular weight=1200; Grain Processing Corporation, Muscatine, Iowa), MALTRIN® M180 (DEV=18; molecular weight=1050; Grain Processing Corporation, Muscatine, Iowa), MALTRIN® M200 (DEV=20; molecular weight=900; Grain Processing Corporation, Muscatine, Iowa), MALTRIN® M250 (DEV=25; molecular weight=720; Grain Processing Corporation, Muscatine, Iowa); MALTRIN QD® M580 (DEV=16.5-19.9; Grain Processing Corporation, Muscatine, Iowa); MALTRIN QD® M585 (DEV=15.0-19.9; Grain Processing Corporation, Muscatine, Iowa); MALTRIN QD® M600 (DEV=20.0-23.0; Grain Processing Corporation, Muscatine, Iowa); GLOBE® Plus 15 DE (Ingredion Inc., Westchester, Ill.); and combinations thereof. In some embodiments, the maltodextrin (or combination of maltodextrins) has a DEV of 15 to 20.

Maltodextrins may be incorporated into inoculant compositions of the present disclosure in any suitable form. In some embodiments, the maltodextrin(s) included in inoculant compositions of the present disclosure is/are at least 70, 75, 80, 85, 90, 91, 92, 93, 94, 95, 96, 97, 98, 99, 99.5% or more pure.

Maltodextrins may be incorporated into inoculant compositions of the present disclosure in any suitable amount(s)/concentration(s). In some embodiments, the maltodextrin(s) comprise about 5 to about 99% or more (by weight) of the inoculant composition. For example, in some embodiments, the non-aqueous carrier comprises about 5, 10, 15, 20, 25, 30, 35, 40, 45, 50, 55, 60, 65, 70, 75, 80, 85, 90, 95, 96, 97, 98, 99% or more of one or more maltodextrins (each and/or collectively) having a DEV value of about 15 to about 20. In some embodiments, the maltodextrin amount/concentration is about 50 to about 95%, about 55% to about 90%, about 60% to about 85%, about 65% to about 80%, or about 70 to about 80% (by weight) of the non-aqueous carrier.

In some embodiments, the non-aqueous carrier comprises, consists essentially of, or consists of one or more monosaccharides, disaccharides and/or oligosaccharides.

Inoculant compositions of the present disclosure may comprise any suitable monosaccharide, including, but limited to, allose, altrose, arabinose, fructose, galactose, glucose, gulose, iodose, lyxose, mannose, ribose, talose, threose and xylose. In some embodiments, the non-aqueous carrier comprises glucose. In some embodiments, the non-aqueous carrier does not comprise glucose.

Inoculant compositions of the present disclosure may comprise any suitable disaccharide, including, but limited to, cellobiose, chitobiose, gentiobiose, gentiobiulose, isomaltose, kojibiose, lactose, lactulose, laminaribiose, maltose (e.g., maltose monohydrate, anhydrous maltose), maltulose, mannobiose, melibiose, melibiulose, nigerose, palatinose, rutinose, mtinulose, sophorose, sucrose, trehalose, turanose and xylobiose. In some embodiments, the the non-aqueous carrier comprises maltose. In some embodiments, the non-aqueous carrier comprises sucrose. In some embodiments, the non-aqueous carrier comprises trehalose. In some embodiments, the non-aqueous carrier does not comprise trehalose.

Inoculant compositions of the present disclosure may comprise any suitable oligosaccharide, including, but limited to, fructo-oligosaccharides, galacto-oligosaccharides, mannon-oligosaccharides and raffinose.

Mono-, di- and/or oligosaccharides may be incorporated into inoculant compositions of the present disclosure in any suitable form. In some embodiments, the mono-, di- and/or oligosaccharide(s) included in inoculant compositions of the present disclosure is/are at least 70, 75, 80, 85, 90, 91, 92, 93, 94, 95, 96, 97, 98, 99, 99.5% or more pure.

Mono-, di- and oligosaccharides may be incorporated into inoculant compositions of the present disclosure in any suitable amount(s)/concentration(s). In some embodiments, the mono-, di- and/or oligosaccharide(s) comprise(s) about 5 to about 95% (by weight) of the inoculant composition. For example, in some embodiments, the non-aqueous carrier comprises about 5, 10, 15, 20, 25, 30, 35, 40, 45, 50, 55, 60, 65, 70, 75, 80, 85, 90, 95% or more (by weight) of one or more mono-, di- and/or oligosaccharides (e.g., maltose and/or trehalose). In some embodiments, the mono-, di- and/or oligosaccharide (e.g., maltose) amount/concentration is about 1 to about 65%, about 5% to about 20%, about 10% to about 25%, about 20% to about 50%, or about 30 to about 60% (by weight) of the non-aqueous carrier.

In some embodiments, the non-aqueous carrier comprises, consists essentially of, or consists of one or more malt extracts.

Inoculant compositions of the present disclosure may comprise any suitable malt extract(s).

Malt extracts may be incorporated into inoculant compositions of the present disclosure in any suitable form. In some embodiments, the malt extracts(s) included in inoculant compositions of the present disclosure is/are at least 70, 75, 80, 85, 90, 91, 92, 93, 94, 95, 96, 97, 98, 99, 99.5% or more pure.

Malt extracts may be incorporated into inoculant compositions of the present disclosure in any suitable amount(s)/concentration(s). In some embodiments, the malt extract(s) comprise(s) about 5 to about 95% (by weight) of the inoculant composition. For example, in some embodiments, the non-aqueous carrier comprises about 5, 10, 15, 20, 25, 30, 35, 40, 45, 50, 55, 60, 65, 70, 75, 80, 85, 90% or more (by weight) of one or more malt extracts. In some embodiments, the malt extract amount/concentration is about 50 to about 99%, about 55% to about 95%, about 60% to about 90%, about 65% to about 90%, or about 70 to about 90% (by weight) of the non-aqueous carrier.

In some embodiments, the non-aqueous carrier comprises, consists essentially of, or consists of one or more peat-based powders and/or granuales.

Inoculant compositions of the present disclosure may comprise any suitable peat-based powder(s) and/or granuale(s).

Peat-based powders and/or granuales extracts may be incorporated into inoculant compositions of the present disclosure in any suitable form. In some embodiments, the peat-based powder(s) and/or granuale(s) included in inoculant compositions of the present disclosure is/are at least 70, 75, 80, 85, 90, 91, 92, 93, 94, 95, 96, 97, 98, 99, 99.5% or more pure.

Peat-based powders and/or granuales may be incorporated into inoculant compositions of the present disclosure in any suitable amount(s)/concentration(s). In some embodiments, the peat-based powder(s) and/or granuale(s) comprise(s) about 5 to about 95% (by weight) of the inoculant composition. For example, in some embodiments, the non-aqueous carrier comprises about 5, 10, 15, 20, 25, 30, 35, 40, 45, 50, 55, 60, 65, 70, 75, 80, 85, 90, 95% or more (by weight) of one or more peat-based powders and/or granuales. In some embodiments, the peat extract amount/concentration is about 50 to about 99%, about 55% to about 95%, about 60% to about 90%, about 65% to about 90%, or about 70 to about 90% (by weight) of the non-aqueous carrier.

In some embodiments, the non-aqueous carrier comprises, consists essentially of, or consists of one or more agriculturally acceptable polymers.

Inoculant compositions of the present disclosure may comprise any suitable agriculturally acceptable polymer(s), including, but not limited to, biodegradable polymers and synthetic polymers. For example, in some embodiments, inoculant compositions of the present disclosure comprise agar, alginate, carrageenan, cellulose, guar gum, locust bean gum, methylcellulose, pectin, polycaprolactone, polylactide, polyvinyl alcohol, polyvinyl pyrrolidone, sodium carboxymethyl cellulose, starch and xanthan gum.

Non-limiting examples of polymers that may be useful in compositions of the present disclosure include TICAXAN® xanthan powders, such as PRE-HYDRATED® TICAXAN® Rapid-3 Powder (TIC Gums, White Marsh, Md.) and combinations thereof.

Additional examples of polymers that may be included in inoculant compositions of the present disclosure may be found in Pouci, et al. AM. J. AGRIC. BIOL. SCI. 3(1):299 (2008).

Agriculturally acceptable polymers may be incorporated into inoculant compositions of the present disclosure in any suitable amount(s)/concentration(s). In some embodiments, the agriculturally acceptable polymer(s) comprise(s) about 5 to about 95% (by weight) of the inoculant composition. For example, in some embodiments, the non-aqueous carrier comprises about 5, 10, 15, 20, 25, 30, 35, 40, 45, 50, 55, 60, 65, 70, 75, 80, 85, 90, 95% or more (by weight) of one or more agriculturally acceptable polymers. In some embodiments, the agriculturally acceptable polymers amount/concentration is about 50 to about 99%, about 55% to about 95%, about 60% to about 90%, about 65% to about 90%, or about 70 to about 90% (by weight) of the non-aqueous carrier.

In some embodiments, inoculant compositions of the present disclosure comprise one or more commercial polymers used in accordance with the manufacturer's recommended amounts/concentrations.

It is to be understood that monosaccharides, disaccharides, oligosaccharides, maltodextrins, malt extracts, agriculturally acceptable polymers and peat-based powders/granuales may be combined to form dry non-aqueous carriers having beneficial properties, including, but not limited to, enhanced stabilization of microbial spores. Thus, in some embodiments, inoculant compositions of the present disclosure comprise a dry non-aqueous carrier that comprises one or more maltodextrins in combination with one or more mono-, di- and/or oligosaccharides, one or more sugar alcohols, one or more malt extracts, one or more agriculturally acceptable polymers and/or one or more peat-based powders and/or granuales.

Maltodextins and mono-, di- and/or oligosaccharides may be incorporated into inoculant compositions of the present disclosure in any suitable ratio(s). In some embodiments, the non-aqueous carrier has a maltodextrin:(mono-, di- and/or oligosaccharide) (e.g., maltodextrin:maltose) ratio of about 1:99 to about 99:1 (by weight, based upon the respective weight percentages of the maltodextrin(s) and mono-, di- and/or oligosaccharide(s) in the non-aqueous carrier). For example, in some embodiments, the non-aqueous carrier has a maltodextrin:(mono-, di- and/or oligosaccharide) (e.g., maltodextrin:maltose) ratio of about 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5 or more. In some embodiments, the maltodextrin:(mono-, di- and/or oligosaccharide) (e.g., maltodextrin:maltose) ratio is about 45:55 to about 95:5. Thus, in some embodiments, inoculant compositions of the present disclosure comprise one or more maltodextrins having a DEV of about 15 to about 20 and one or more mono-, di- and/or oligosaccharides (e.g., maltose) in a ratio of about 45:55, 50:50, 55:45, 60:40, 65:35, 70:30, 75:25, 80:20, 85:15, 90:10, 95:5.

Maltodextins and malt extracts may be incorporated into inoculant compositions of the present disclosure in any suitable ratio(s). In some embodiments, the non-aqueous carrier has a maltodextrin:malt extract ratio of about 1:99 to about 99:1 (by weight, based upon the respective weight percentages of the maltodextrin(s) and malt extract(s) in the non-aqueous carrier). For example, in some embodiments, the non-aqueous carrier has a maltodextrin:malt extract ratio of about 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5 or more. In some embodiments, the maltodextrin:malt extract ratio is about 45:55 to about 95:5. Thus, in some embodiments, inoculant compositions of the present disclosure comprise one or more maltodextrins having a DEV of about 15 to about 20 and one or more malt extracts in a ratio of about 45:55, 50:50, 55:45, 60:40, 65:35, 70:30, 75:25, 80:20, 85:15, 90:10, 95:5.

Maltodextins and peat-based powders and/or granuales may be incorporated into inoculant compositions of the present disclosure in any suitable ratio(s). In some embodiments, the non-aqueous carrier has a maltodextrin:peat powder/granuale ratio of about 1:99 to about 99:1 (by weight, based upon the respective weight percentages of the maltodextrin(s) and peat powder(s)/granuale(s) in the non-aqueous carrier). For example, in some embodiments, the non-aqueous carrier has a maltodextrin:peat powder/granuale ratio of about 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5 or more. In some embodiments, the maltodextrin:peat powder/granuale ratio is about 45:55 to about 95:5. Thus, in some embodiments, inoculant compositions of the present disclosure comprise one or more maltodextrins having a DEV of about 15 to about 20 and one or more peat-based powders and/or granuales in a ratio of about 45:55, 50:50, 55:45, 60:40, 65:35, 70:30, 75:25, 80:20, 85:15, 90:10, 95:5.

Non-aqueous carriers may be incorporated into inoculant compositions of the present disclosure in any suitable amount(s)/concentration(s).

In some embodiments, the non-aqueous carrier(s) comprise(s) about 5 to about 99.9% (by weight) of the inoculant composition. For example, in some embodiments, the non-aqueous carrier(s) constitute(s) about 10, 15, 20, 25, 30, 35, 40, 45, 50, 55, 60, 65, 70, 75, 80, 85, 90, 95, 96, 97, 98, 99, 99.5% or more (by weight) of the inoculant composition. In some embodiments, the non-aqueous carrier amount/concentration is about 50 to about 99%, about 55% to about 95%, about 60% to about 95%, about 65% to about 90%, about 70 to about 90%, about 75 to about 90%, about 80 to about 90% or about 80 to about 85% (by weight) of the inoculant composition.

In some embodiments, the amount/concentration of the non-aqueous carrier(s) in the inoculant composition is effective to ensure that at least about 0.01, 0.05, 0.1, 0.5, 1, 2, 3, 4, 5, 10, 15, 20, 25, 30, 35, 40, 45, 50, 55, 60, 65% or more of the microbial spores/vegetative cells in the inoculant composition survive following desiccation (of about 0, 5, 10, 15, 20, 25, 30, 35, 40, 45, 50, 55, 60, 65, 70, 75, 80, 85, 90, 95% or more) and storage at 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the amount/concentration of the non-aqueous carrier(s) in the inoculant composition is effective to ensure that at least about 0.01, 0.05, 0.1, 0.5, 1, 2, 3, 4, 5, 10, 15, 20, 25, 30, 35, 40, 45, 50, 55, 60, 65% or more of the microbial spores/vegetative cells in the inoculant composition survive following storage at 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure comprise one or more commercial carriers used in accordance with the manufacturer's recommended amounts/concentrations.

In the interest of maximizing the teaching of the present application and without intending to be limited by any particular theory, applicants submit that the aforementioned carriers may enhance the stability and survival of microbial spores in an inoculant composition by encapsulating the microbial spores, thereby reducing their exposure to elements that would otherwise cause the spores to germinate or destabilize. In such instances, the non-aqueous carrier may be referred to as a proctectant.

In some embodiments, the non-aqueous carrier at least partially encapsulate 40, 45, 50, 55, 60, 65, 70, 75, 80, 85, 90, 95, 96, 97, 98, 99% or more of the microbial spores in the inoculant composition. For example, in some embodiments, inoculant compositions of the present disclosure comprise one or more monosaccharides, disaccharides, oligosaccharides, maltodextrins and/or malt extracts that fully or partially encapsulate at least 50, 55, 60, 65, 70, 75, 80, 85, 90 or 95% of the microbial spores in the inoculant composition.

Inoculant compositions of the present disclosure may comprise any suitable agriculturally acceptable dispersant(s), including, but not limited to, surfactants and wetting agents.

In some embodiments, inoculant compositions of the present disclosure comprise one or more anionic surfactants. For example, in some embodiments, inoculant compositions of the present disclosure comprise one or more water-soluble anionic surfactants and/or one or more water-insoluble anionic surfactants, optionally one or more anionic surfactants selected from the group consisting of alkyl carboxylates (e.g., sodium stearate), alkyl sulfates (e.g., alkyl lauryl sulfate, sodium lauryl sulfate), alkyl ether sulfates, alkyl amido ether sulfates, alkyl aryl polyether sulfates, alkyl aryl sulfates, alkyl aryl sulfonates, alkyl sulfonates, alkyl amide sulfonates, alkyl aryl sulfonates, alkyl benzene sulfonates, alkyl diphenyloxide sulfonate, alpha-olefin sulfonates, alkyl naphthalene sulfonates, paraffin sulfonates, alkyl sulfosuccinates, alkyl ether sulfosuccinates, alkylamide sulfosuccinates, alkyl sulfosuccinamates, alkyl sulfoacetates, alkyl phosphates, alkyl ether phosphates, acyl sarconsinates, acyl isethionates, N-acyl taurates, N-acyl-N-alkyltaurates, benzene sulfonates, cumene sulfonates, dioctyl sodium sulfosuccinate, ethoxylated sulfosuccinates, lignin sulfonates, linear alkylbenzene sulfonates, monoglyceride sulfates, perfluorobutanesulfonate, perfluorooctanesulfonate, phosphate ester, styrene acrylic polymers, toluene sulfonates and xylene sulfonates.

In some embodiments, inoculant compositions of the present disclosure comprise one or more cationic surfactants. For example, in some embodiments, inoculant compositions of the present disclosure comprise one or more pH-dependent amines and/or one or more quaternary ammonium cations, optionally one or more cationic surfactants selected from the group consisting of alkyltrimethylammonium salts (e.g., cetyl trimethylammonium bromide, cetyl trimethylammonium chloride), cetylpyridinium chloride, benzalkonium chloride, benzethonium chloride, 5-Bromo-5-nitro-1,3-dioxane, dimethyldioctadecylammonium chloride, cetrimonium bromide, dioctadecyldimethylammonium bromide and/or octenidine dihydrochloride.

In some embodiments, inoculant compositions of the present disclosure comprise one or more nonionic surfactants. For example, in some embodiments, inoculant compositions of the present disclosure comprise one or more water-soluble nonionic surfactants and/or one or more water-insoluble nonionic surfactants, optionally one or more nonionic surfactants selected from the group consisting of alcohol ethoxylates (e.g., TERGITOL™ 15-S surfactants, such as TERGITOL™15-S-9 (The Dow Chemical Company, Midland, Mich.)), alkanolamides, alkanolamine condensates, carboxylic acid esters, cetostearyl alcohol, cetyl alcohol, cocamide DEA, dodecyldimethylamine oxides, ethanolamides, ethoxylates of glycerol ester and glycol esters, ethylene oxide polymers, ethylene oxide-propylene oxide copolymers, glucoside alkyl ethers, glycerol alkyl ethers (e.g.), glycerol esters, glycol alkyl ethers (e.g., polyoxyethylene glycol alkyl ethers, polyoxypropylene glycol alkyl ethers), glycol alkylphenol ethers (e.g., polyoxyethylene glycol alkylphenol ethers), glycol esters, monolaurin, pentaethylene glycol monododecyl ethers, poloxamer, polyamines, polyglycerol polyricinoleate, polysorbate, polyoxyethylenated fatty acids, polyoxyethylenated mercaptans, polyoxyethylenated polyoxyproylene glycols, polyoxyethylene glycol sorbitan alkyl esters, polyethylene glycol-polypropylene glycol copolymers, polyoxyethylene glycol octylphenol ethers, polyvinyl pynolidones, sugar-based alkyl polyglycosides, sulfoanylamides, sorbitan fatty acid alcohol ethoxylates, sorbitan fatty acid ester ethoxylates, sorbitan fatty acid ester and/or tertiary acetylenic glycols.

In some embodiments, inoculant compositions of the present disclosure comprise at least one nonionic surfactant. In some embodiments, inoculant compositions of the present disclosure comprise at least one water insoluble nonionic surfactant and at least one water soluble nonionic surfactant. In some embodiments, inoculant compositions of the present disclosure comprise a combination of nonionic surfactants having hydrocarbon chains of substantially the same length.

In some embodiments, inoculant compositions of the present disclosure comprise one or more zwitterionic surfactants. For example, in some embodiments, inoculant compositions of the present disclosure comprise one or more betaines and/or one or more sultaines, optionally one or more zwitterionic surfactants selected from the group consisting of 3-[(3-cholamidopropyl)dimethylammonio]-1-propanesulfonate, cocamidopropyl betaine, cocamidopropyl hydroxysultaine, phosphatidylserine, phosphatidylethanolamine, phosphatidylcholine and/or one or more sphingomyelins.

In some embodiments, inoculant compositions of the present disclosure comprise one or more soaps and/or organosilicone surfactants. For example, in some embodiments, inoculant compositions of the present disclosure comprise one or more alkali metal salts of fatty acids.

In some embodiments, inoculant compositions of the present disclosure comprise one or more wetting agents. For example, in some embodiments, inoculant compositions of the present disclosure comprise one or more naphthalene sulfonates, optionally one or more alkyl naphthalene sulfonates (e.g., sodium alkyl naphthalene sulfonate), one or more isopropyl naphthalene sulfonates (e.g., sodium isopropyl naphthalene sulfonate) and/or one or more butyl naphthalene sulfonates (e.g., sodium n-butyl naphthalene sulfonate).

Selection of appropriate surfactants will depend on the intended application(s) and the microorganism(s) present in the inoculant composition. In general, the surfactant(s) will have low toxicity for the microorganism(s) in the inoculant composition and for the plant part(s) to which the inoculant composition is to be applied. In some embodiments, the surfactant(s) will be selected to wet and/or emulsify one or more soils.

Non-limiting examples of dispersants that may be useful in compositions of the present disclosure include Atlox™ (e.g., 4916, 4991; Croda International PLC, Edison, N.J.), BIO-SOFT® (e.g., N series, such as N1-3, N1-7, N1-5, N1-9, N23-3, N2.3-6.5, N25-3, N25-7, N25-9, N91-2.5, N91-6, N91-8; Stepan Company, Northfield, Ill.), MAKON® nonionic surfactants (e.g., DA-4, DA-6 and DA-9; Stepan Company, Northfield, Ill.), MORWET® powders (Akzo Nobel Surface Chemistry LLC, Chicago, Ill.), MULTIWET™ surfactants (e.g., MO-70R, MO-85P, MO-85P-PW-(AP); Croda International PLC, Edison, N.J.), SILWET® L-77 (Helena Chemical Company, Collierville, Tenn.), SPAN™ surfactants (e.g., 20, 40, 60, 65, 80 and 85; Croda Inc., Edison N.J.), TAMOL™ dispersants (The Dow Chemical Company, Midland, Mich.), TERGITOL™ surfactants (e.g., 15-S-9, TMN-6, TMN-100× and XD; The Dow Chemical Company, Midland, Mich.), TERSPERSE surfactants (e.g., 2001, 2020, 2100, 2105, 2158, 2700, 4894 and 4896; Hunstman Corp., The Woodlands, Tex.), TRITON™ surfactants (e.g., X-100; The Dow Chemical Company, Midland, Mich.), TWEEN® surfactants (e.g., TWEEN® 20, 21, 22, 23, 28, 40, 60, 61, 65, 80, 81 and 85; Croda International PLC, Edison, N.J.) and combinations thereof.

Dispersants may be incorporated into inoculant compositions of the present disclosure in any suitable amount(s)/concentration(s). In some embodiments, the dispersant(s) comprise(s) about 0.1 to about 25% (by weight) of the inoculant composition. For example, inoculant compositions of the present disclosure may comprise about 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25% or more (by weight) of one or more dispersants. In some embodiments, the dispersant (s) comprise(s) about 0.1, 0.2, 0.3, 0.4, 0.5, 0.6, 0.7, 0.8, 0.9 or 1 to about 1, 1.5, 2, 2.5, 3, 3.5, 4, 4.5, 5, 5.5, 6, 6.5, 7, 7.5, 8, 8.5, 9, 9.5 or 10% (by weight) of the inoculant composition.

In some embodiments, inoculant compositions of the present disclosure comprise one or more commercial wetting agents and/or one or more surfactants used in accordance with the manufacturer's recommended amounts/concentrations.

Additional examples of dispersants that may be included in inoculant compositions of the present disclosure may be found in BAIRD & ZUBLENA. 1993. SOIL FACTS: USING WETTING AGENTS (NONIONIC SURFACTANTS) ON SOIL (North Carolina Cooperative Extension Service Publication AG-439-25) (1993); BURGES, FORMULATION OF MICROBIAL BIOPESTICIDES: BENEFICIAL MICROORGANISMS, NEMATODES AND SEED TREATMENTS (Springer Science & Business Media) (2012); MCCARTY, WETTING AGENTS (Clemson University Cooperative Extension Service Publication) (2001).

Inoculant compositions of the present disclosure may comprise any suitable excipient(s), including, but not limited to, anti-freezing agents, drying agents, safeners and pH buffers.

Inoculant compositions of the present disclosure may comprise any suitable agriculturally acceptable anti-freezing agent(s), including, but not limited to, ethylene glycol, glycerin, propylene glycol and urea.

In some embodiments, inoculant compositions of the present disclosure comprise one or more commercial anti-freezing agents used in accordance with the manufacturer's recommended amounts/concentrations.

Inoculant compositions of the present disclosure may comprise any suitable agriculturally acceptable drying agent(s), including, but not limited to, drying powders. For example, in some embodiments, inoculant compositions of the present disclosure comprise calcium stearate, clay (e.g., attapulgite clay, montmorillonite clay), graphite, magnesium stearate, magnesium sulfate, powdered milk, silica (e.g., fumed silica, hydrophobically-coated silica, precipitated silica), soy lecithin and/or talc.

Non-limiting examples of drying agents that may be useful in compositions of the present disclosure include AEROSIL® hydrophobic fumed silica powders (Evonik Corporation, Parsippany, N.J.), BENTOLITE® powders (BYK-Chemie GmbH, Wesel, Germany), SIPERNAT® silica powders (Evonik Corporation, Parsippany, N.J.) and combinations thereof.

Additional examples of drying agents that may be included in inoculant compositions of the present disclosure may be found in BURGES, FORMULATION OF MICROBIAL BIOPESTICIDES: BENEFICIAL MICROORGANISMS, NEMATODES AND SEED TREATMENTS (Springer Science & Business Media) (2012).

Drying agents may be incorporated into inoculant compositions of the present disclosure in any suitable amount(s)/concentration(s). In some embodiments, the inoculant compositions of the present disclosure comprise about 0.5 to about 10 grams of drying powder per liter of inoculant composition. For example, inoculant compositions of the present disclosure may comprise about 0.5, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10 grams or more of drying powder per liter of inoculant composition. In some embodiments, the amount/concentration of drying agent(s) comprise(s) calcium stearate, attapulgite clay, montmorillonite clay, graphite, magnesium stearate, silica (e.g., fumed silica, hydrophobically-coated silica and/or precipitated silica) and/or talc.

In some embodiments, inoculant compositions of the present disclosure comprise one or more commercial drying agents used in accordance with the manufacturer's recommended amounts/concentrations.

Inoculant compositions of the present disclosure may comprise any suitable agriculturally acceptable dust suppressant(s), including, but not limited to, adhesives, glycerin, mineral oils, paraffinic oils, vegetable oils and synthetic polymers. It is to be understood that some compounds may act as both an adhesive and a dust suppressant. Indeed, the dust suppressant activity of many compounds arises from their ability to adhere dust particles to other heavier particles. For example, in some embodiments of the present disclosure, one or more oils is used to adhere microbial spores in the inoculant composition to larger particles comprising one or more maltodextrins.

Non-limiting examples of dust suppressants that may be useful in compositions of the present disclosure include ARENAPRO, BIORAIN and ROADKILL (Dustkill LLC, Columbus, Ind.), BIO-SOFT® surfactants (e.g., N series, such as N1-3, N1-7, N1-5, N1-9, N23-3, N2.3-6.5, N25-3, N25-7, N25-9, N91-2.5, N91-6, N91- 8; Stepan Company, Northfield, Ill.), DURASOIL (Soilworks, LLC, Scottsdale, Ariz.), DUSGON (Dupont (Australia) Ltd, Macquarie Park, Australia), DUSTRX (Seaco Technologies, Inc., Bakersfield, Calif.), SUN AG® oils (HollyFrontier Refining & Marketing, LLC, Plymouth Meeting, Pa.), SUNSPRAY® oils (e.g., 6N, 6E, 8N, 11N; HollyFrontier Refining & Marketing, LLC, Plymouth Meeting, Pa.), SUNSPRAY® ULTRA-FINE® oils (HollyFrontier Refining & Marketing, LLC, Plymouth Meeting, Pa.), TOMADOL® surfactants (e.g., 23-1, 23-3, 23-5, 23-6.5; Air Products and Chemicals, Inc., Allentown, Pa.) and combinations thereof.

Dust suppressants may be incorporated into inoculant compositions of the present disclosure in any suitable amount(s)/concentration(s).

In some embodiments, dust suppressants comprise about 0.1 to about 30% (by weight) of the inoculant composition. For example, inoculant compositions of the present disclosure may comprise about 0.1, 0.2, 0.3, 0.4, 0.5, 0.6, 0.7, 0.8, 0.9, 1, 1.25, 1.5, 1.75, 2, 2.25, 2.5, 2.75, 3, 3.25, 3.5, 3.75, 4, 4.25, 4.5, 4.75, 5, 6, 7, 8, 9, 10% or more (by weight) of one or more dust suppressants. In some embodiments, the dust suppressant amount/concentration is about 1 to about 2, 3, 4, 5, 6, 7, 8, 9 or 10%, about 1.5 to about 2, 3, 4, 5, 6, 7, 8, 9 or 10%, about 2 to about 3, 4, 5, 6, 7, 8, 9 or 10%, about 2.5 to about 3, 4, 5, 6, 7, 8, 9 or 10% or about 3 to about 4, 5, 6, 7, 8, 9 or 10% (by weight) of the inoculant composition.

It is to be understood that some compounds may act as both a dispersant and a dust suppressant. For example, in some embodiments, inoculant compositions of the present disclosure comprise one or more surfactants, such as BIO-SOFT® N23-3, that disperse microorganisms within the inoculant composition and suppress dusting.

As noted above, the non-aqueous carrier in inoculant compositions of the present invention may act as a proctectant. It is to be understood that inoculant compositions of the present disclosure may comprise additional protectants.

Protectants may be incorporated into inoculant compositions of the present disclosure in any suitable amount(s)/concentration(s).

In some embodiments, the protectant(s) comprise(s) about 0.1 to about 25% (by weight) of the inoculant composition. For example, inoculant compositions of the present disclosure may comprise about 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25% or more (by weight) of one or more protectants. In some embodiments, the protectant amount/concentration is about 0.1, 0.2, 0.3, 0.4, 0.5, 0.6, 0.7, 0.8, 0.9 or 1 to about 1, 1.5, 2, 2.5, 3, 3.5, 4, 4.5, 5, 5.5, 6, 6.5, 7, 7.5, 8, 8.5, 9, 9.5 or 10% (by weight) of the inoculant composition.

In some embodiments, the protectant amount/concentration is effective to ensure that at least about 0.01, 0.05, 0.1, 0.5, 1, 2, 3, 4, 5, 10, 15, 20, 25, 30, 35, 40, 45, 50, 55, 60, 65% or more of the microbial spores/vegetative cells in the inoculant composition survive following storage at 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the protectant amount/concentration is effective to ensure that at least about 0.01, 0.05, 0.1, 0.5, 1, 2, 3, 4, 5, 10, 15, 20, 25, 30, 35, 40, 45, 50, 55, 60, 65% or more of the microbial spores/vegetative cells in the inoculant composition survive following desiccation (of about 0, 5, 10, 15, 20, 25, 30, 35, 40, 45, 50, 55, 60, 65, 70, 75, 80, 85, 90, 95% or more) and storage at 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the protectant amount/concentration is effective to ensure that at least about 0.01, 0.05, 0.1, 0.5, 1, 2, 3, 4, 5, 10, 15, 20, 25, 30, 35, 40, 45, 50, 55, 60, 65% or more of the microbial spores/vegetative cells in the inoculant composition survive following cryopreservation at or below −80° C. for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure comprise one or more sugar alcohols (e.g., sorbitol).

Sugar alcohols may be incorporated into inoculant compositions of the present disclosure in any suitable amount(s)/concentration(s). In some embodiments, the sugar alcohol(s) comprise(s) about 0.005 to about 10% (by weight) of the inoculant composition. For example, inoculant compositions of the present disclosure may comprise about 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5% or more (by weight) of one or more sugar alcohols (e.g., sorbitol).

In some embodiments, inoculant compositions of the present disclosure comprise one or more peat extracts.

Peat extracts may be incorporated into inoculant compositions of the present disclosure in any suitable amount(s)/concentration(s). In some embodiments, the peat extract(s) comprise(s) about 0.1 to about 25% (by weight) of the inoculant composition. For example, inoculant compositions of the present disclosure may comprise about 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25% or more (by weight) of one or more peat extracts. In some embodiments, the peat extract amount/concentration is about 0.5 to about 10% (by weight) of the inoculant composition.

In some embodiments, inoculant compositions of the present disclosure comprise one or more peptones.

Peptones may be incorporated into inoculant compositions of the present disclosure in any suitable amount(s)/concentration(s). In some embodiments, the peptone(s) comprise(s) about 0.1 to about 25% (by weight) of the inoculant composition. For example, inoculant compositions of the present disclosure may comprise about 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25% or more (by weight) of one or more peptones. In some embodiments, the peptone amount/concentration is about 0.5 to about 10% (by weight) of the inoculant composition.

In some embodiments, inoculant compositions of the present disclosure comprise one or more skim milk extracts.

Skim milk extracts may be incorporated into inoculant compositions of the present disclosure in any suitable amount/concentration. In some embodiments, skim milk extracts comprise about 0.1 to about 25% (by weight) of the inoculant composition. For example, inoculant compositions of the present disclosure may comprise about 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25% or more (by weight) of skim milk extracts. In some embodiments, the skim milk extract amount/concentration is about 0.5 to about 10% (by weight) of the inoculant composition.

In some embodiments, inoculant compositions of the present disclosure comprise one or more hygroscopic polymers. For example, inoculant compositions of the present disclosure may comprise one or more albumins, alginates, celluloses, gums (e.g., cellulose gum, guar gum, gum arabic, gum combretum, xantham gum), methyl celluloses, nylons, pectins, polyacrylic acids, polycarbonates, polyethylene glycols (PEG), polyethylenimines (PEI), polylactides, polymethylacrylates (PMA), polyurethanes, polyvinyl alcohols (PVA), polyvinylpyrrolidones (PVP), propylene glycols, sodium carboxymethyl celluloses and/or starches.

Non-limiting examples of hygroscopic polymers that may be useful in compositions of the present disclosure include AGRIMER™ polymers (e.g., 30, AL-10 LC, AL-22, AT/ATF, VA 3E, VA 3l, VA 5E, VA 5l, VA 6, VA 6E, VA 7E, VA 7l, VEMA AN-216, VEMA AN-990, VEMA AN-1200, VEMA AN-1980, VEMA H-815MS; Ashland Specialty Ingredients, Wilmington, Del.), EASYSPERSE™ polymers (Ashland Specialty Ingredients, Wilmington, Del.); DISCO™ AG polymers (e.g., L-250, L-280, L-285, L-286, L-320, L-323, L-517, L-519, L-520, L800; Incotec Inc., Salinas, Calif.), KELZAN® polymers (Bri-Chem Supply Ltd., Calgary, Alberta, Calif.), SEEDWORX™ polymers (e.g., Bio 200; Aginnovation, LLC, Walnut Groove, Calif.), TABULOSE® gels (e.g., SC-580, SC-612, SC-613, SC-681; Blanver Farmoquimica, Boca Raton, Fla.), TICAXAN® xanthan powders (TIC Gums, White Marsh, Md.) and combinations thereof.

Additional examples of hygroscopic polymers that may be included in inoculant compositions of the present disclosure may be found in Pouci, et al. AM. J. AGRIC. BIOL. SCI. 3(1):299 (2008).

Hygroscopic polymers may be incorporated into inoculant compositions of the present disclosure in any suitable amount(s)/concentration(s). In some embodiments, the hygroscopic polymer(s) comprise(s) about 0.1 to about 25% (by weight) of the inoculant composition. In some embodiments, the hygroscopic polymer(s) comprise(s) about 0.5 to about 1, 1.5, 2, 2.5, 3, 3.5, 4, 4.5, 5, 5.5, 6, 6.5, 7, 7.5, 8, 8.5, 9, 9.5 or 10% (by weight) of the inoculant composition. For example, inoculant compositions of the present disclosure may comprise about 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25% or more (by weight) of one or more hygroscopic polymers. In some embodiments, the hygroscopic polymer amount/concentration is about 0.5 to about 10% (by weight) of the inoculant composition. In some embodiments, the hygroscopic polymer amount/concentration is about 0.5 to about 5% (by weight) of the inoculant composition.

In some embodiments, the hygroscopic polymer amount/concentration is effective to ensure that at least about 0.01, 0.05, 0.1, 0.5, 1, 2, 3, 4, 5, 10, 15, 20, 25, 30, 35, 40, 45, 50, 55, 60, 65% or more of the microbial spores in the inoculant composition survive following storage at 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the hygroscopic polymer amount/concentration is effective to ensure that at least about 0.01, 0.05, 0.1, 0.5, 1, 2, 3, 4, 5, 10, 15, 20, 25, 30, 35, 40, 45, 50, 55, 60, 65% or more of the microbial spores in the inoculant composition survive following desiccation (of about 0, 5, 10, 15, 20, 25, 30, 35, 40, 45, 50, 55, 60, 65, 70, 75, 80, 85, 90, 95% or more) and storage at 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the hygroscopic polymer amount/concentration is effective to ensure that at least about 0.01, 0.05, 0.1, 0.5, 1, 2, 3, 4, 5, 10, 15, 20, 25, 30, 35, 40, 45, 50, 55, 60, 65% or more of the microbial spores in the inoculant composition survive following cryopreservation at or below −80° C. for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure comprise one or more commercial hygroscopic polymers used in accordance with the manufacturer's recommended amounts/concentrations.

In some embodiments, inoculant compositions of the present disclosure comprise one or more oxidation control components.

Inoculant compositions of the present disclosure may comprise any suitable oxidation control component(s), including, but not limited to, antioxidants and/or oxygen scavengers. In some embodiments, the oxidation control component is/comprises ascorbic acid and/or glutathione.

In some embodiments, inoculant compositions comprise one or more antioxidants. For example, in some embodiments, inoculant compositions of the present disclosure comprise ascorbic acid, ascorbyl palmitate, ascorbyl stearate, calcium ascorbate, carotenoids, lipoic acid, phenolic compounds (e.g., flavonoids, flavones, flavonols), potassium ascorbate, sodium ascorbate, thiols (e.g., glutathione, lipoic acid, N-acetyl cysteine), tocopherols, tocotrienols, ubiquinone and/or uric acid.

Non-limiting examples of antioxidants that may be useful in compositions of the present disclosure include those that are soluble in the cell membrane (e.g., alpha tocopherol (vitamin E), ascorbyl palmitate), those that are soluble in alcohols (e.g., IRGANOX® antioxidants (BASF Schweiz AG, Basel, Switzerland)) and those that are soluble in water (e.g., ascorbic acid and isomers or ascorbic acid, sodium or potassium salts of ascorbic acid or isomers or ascorbic acid, glutathione, sodium or potassium salts of glutathione). In some embodiments, use of a membrane-soluble antioxidant necessitates the addition of one or more surfactants to adequately disperse the antioxidant within the inoculant composition.

In some embodiments, inoculant compositions of the present disclosure comprise one or more commercial antioxidants used in accordance with the manufacturer's recommended amounts/concentrations.

In some embodiments, inoculant compositions comprise one or more naturally occurring or synthetic oxygen scavengers. For example, in some embodiments, inoculant compositions of the present disclosure comprise ascorbic acid, ascorbate salts, catechol and/or sodium hydrogen carbonate.

In some embodiments, inoculant compositions of the present disclosure comprise one or more commercial oxygen scavengers used in accordance with the manufacturer's recommended amounts/concentrations.

Oxidation control components may be incorporated into inoculant compositions of the present disclosure in any suitable amount(s)/concentration(s).

In some embodiments, the oxidation control component(s) comprise(s) about 0.0001 to about 5% or more (by weight) of the composition. For example, inoculant compositions of the present disclosure may comprise about 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5% or more of one or more oxidation control components. In some embodiments, the amount/concentration of oxidation control components is about 0.005 to about 2% (by weight) of the composition. In some embodiments, the oxidation control component(s) is/are present in a concentration ranging from about $1 \times 10^{-20}$ M to about $1 \times 10^{-1}$ M. For example, one or more oxidation control components may be added at a concentration of $1 \times 10^{-20}$ M, $1 \times 10^{-19}$ M, $1 \times 10^{-18}$ M, $1 \times 10^{-17}$ M, $1 \times 10^{-16}$ M, $1 \times 10^{-15}$ M, $1 \times 10^{-14}$ M, $1 \times 10^{-13}$ M, $1 \times 10^{-12}$ M, $1 \times 10^{-11}$ M, $1 \times 10^{-10}$ M, $1 \times 10^{-9}$ M, $1 \times 10^{-8}$ M, $1 \times 10^{-7}$ M, $1 \times 10^{-6}$ M, $1 \times 10^{-5}$ M, $1 \times 10^{-4}$ M, $1 \times 10^{-3}$ M, $1 \times 10^{-2}$ M, $1 \times 10^{-1}$ M or more.

In some embodiments, the amount/concentration of oxidation control components is effective to ensure that at least about 0.01, 0.05, 0.1, 0.5, 1, 2, 3, 4, 5, 10, 15, 20, 25, 30, 35, 40, 45, 50, 55, 60, 65% or more of the microbial spores in the inoculant composition survive following storage at 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the amount/concentration of oxidation control components is effective to ensure that at least about 0.01, 0.05, 0.1, 0.5, 1, 2, 3, 4, 5, 10, 15, 20, 25, 30, 35, 40, 45, 50, 55, 60, 65% or more of the microbial spores in the inoculant composition survive following desiccation (of about 0, 5, 10, 15, 20, 25, 30, 35, 40, 45, 50, 55, 60, 65, 70, 75, 80, 85, 90, 95% or more) and storage at 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the amount/concentration of oxidation control components is effective to ensure that at least about 0.01, 0.05, 0.1, 0.5, 1, 2, 3, 4, 5, 10, 15, 20, 25, 30, 35, 40, 45, 50, 55, 60, 65% or more of the microbial spores in the inoculant composition survive following cryopreservation at or below −80° C. for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

Inoculant compositions of the present disclosure may comprise any suitable safener(s), including, but not limited to, naphthalic anhydride.

Safeners may be incorporated into inoculant compositions of the present disclosure in any suitable amount(s)/concentration(s).

In some embodiments, inoculant compositions of the present disclosure comprise one or more commercial safeners used in accordance with the manufacturer's recommended amounts/concentrations.

Inoculant compositions of the present disclosure may comprise any suitable pH buffer(s), including, but not limited to, potassium phosphate monobasic and potassium phosphate dibasic.

Inoculant compositions of the present disclosure may comprise any suitable adhesive(s), including, but not limited to, adhesive compositions comprising one or more maltodextrins and/or one or more mono-, di- or oligosaccharides. Inoculant compositions of the present disclosure may be formulated into any suitable type of composition, including, but not limited to, seed coatings, soil inoculants and foliar inoculants.

Inoculant compositions of the present disclosure may comprise any suitable anti-settling agent(s), including, but not limited to, polyvinyl acetate, polyvinyl alcohols with different degrees of hydrolysis, polyvinylpyrrolidones, polyacrylates, acrylate-, polyol- or polyester-based paint system binders which are soluble or dispersible in water, moreover copolymers of two or more monomers such as acrylic acid, methacrylic acid, itaconic acid, maleic acid, fumaric acid, maleic anhydride, vinylpyrrolidone, ethylenically unsaturated monomers such as ethylene, butadiene, isoprene, chloroprene, styrene, divinylbenzene, ot-methylstyrene or p-methylstyrene, further vinyl halides such as vinyl chloride and vinylidene chloride, additionally vinyl esters such as vinyl acetate, vinyl propionate or vinyl stearate, moreover vinyl methyl ketone or esters of acrylic acid or methacrylic acid with monohydric alcohols or polyols such as methyl acrylate, methyl methacrylate, ethyl acrylate, ethylene methacrylate, lauryl acrylate, lauryl methacrylate, decyl acrylate, N,N-dimethylamino-ethyl methacrylate, 2-hydroxyethyl methacrylate, 2-hydroxypropyl methacrylate or glycidyl methacrylate, furthermore diethyl esters or monoesters of unsaturated dicarboxylic acids, furthermore (meth)acrylamido-N-methylol methyl ether, amides or nitriles such as acrylamide, methacrylamide, N-methylol(meth)acrylamide, acrylonitrile, methacrylonitrile, and also N-substituted maleiraides and ethers such as vinyl butyl ether, vinyl isobutyl ether or vinyl phenyl ether, and combinations thereof.

Anti-settling agents may be incorporated into inoculant compositions of the present disclosure in any suitable amount(s)/concentration(s). In some embodiments, inoculant compositions of the present disclosure comprise about 0.0001 to about 10% or more (by weight) of the composition. For example, inoculant compositions of the present disclosure may comprise about 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5, 5.5, 6, 6.5, 7, 7.5, 8, 8.5, 9, 9.5, 10% or more of one or more anti-settling agents. In some embodiments, the amount/concentration of anti-settling agents is about 0.01 to about 5% (by weight) of the composition.

In some embodiments, inoculant compositions of the present disclosure comprise one or more commercial anti-settling agents used in accordance with the manufacturer's recommended amounts/concentrations.

As noted above, inoculant compositions of the present invention may comprise myriad agriculturally beneficial microbial spores. It is to understand that inoculant compositions of the present disclosure may comprise other agriculturally beneficial constituents such as biostimulants, microbial extracts, nutrients, pesticides and plant signal molecules.

Inoculant compositions of the present disclosure may comprise any suitable biostimulant(s), including, but not limited to, seaweed extracts (e.g., *Ascophyllum nodosum* extracts, such as alginate, *Ecklonia maxima* extracts, etc.), humic acids (e.g., potassium humate), fulvic acids, myo-inositol, glycine and combinations thereof.

Biostimulants may be incorporated into inoculant compositions of the present disclosure in any suitable amount(s)/concentration(s). In some embodiments, the biostimulant(s) comprise(s) about 0.01 to about 5% (by weight) of the inoculant composition. For example, inoculant compositions of the present disclosure may comprise about 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% or more (by weight) of one or more biostimulants. In some embodiments, the biostimulant(s) comprise(s) about 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1 to about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% (by weight) of the inoculant composition.

Inoculant compositions of the present disclosure may comprise any suitable microbial extract(s), including, but not limited to, bacterial extracts (e.g., extracts of media comprising one or more diazotrophs, phosphate-solubilizing microorganisms and/or biopesticides), fungal extracts and combinations thereof. In some embodiments, inoculant compositions of the present disclosure comprise one or more *Azospirillum* extracts (e.g., an extract of media comprising *A. brasilense* INTA Az-39), one or more *Bradyrhizobium* extracts (e.g., an extract of media comprising *B. elkanii* SEMIA 501, *B. elkanii* SEMIA 587, *B. elkanii* SEMIA 5019, *B. japonicum* NRRL B-50586 (also deposited as NRRL B-59565), *B. japonicum* NRRL B-50587 (also deposited as NRRL B-59566), *B. japonicum* NRRL B-50588 (also deposited as NRRL B-59567), *B. japonicum* NRRL B-50589 (also deposited as NRRL B-59568), *B. japonicum* NRRL B-50590 (also deposited as NRRL B-59569), *B. japonicum* NRRL B-50591 (also deposited as NRRL B-59570), *B. japonicum* NRRL B-50592 (also deposited as NRRL B-59571), *B. japonicum* NRRL B-50593 (also deposited as NRRL B-59572), *B. japonicum* NRRL B-50594 (also deposited as NRRL B-50493), *B. japonicum* NRRL B-50608, *B. japonicum* NRRL B-50609, *B. japonicum* NRRL B-50610, *B. japonicum* NRRL B-50611, *B. japonicum* NRRL B-50612, *B. japonicum* NRRL B-50726, *B. japonicum* NRRL B-50727, *B. japonicum* NRRL B-50728, *B. japonicum* NRRL B-50729, *B. japonicum* NRRL B-50730, *B. japonicum* SEMIA 566, *B. japonicum* SEMIA 5079, *B. japonicum* SEMIA 5080, *B. japonicum* USDA 6, *B. japonicum* USDA 110, *B. japonicum* USDA 122, *B. japonicum* USDA 123, *B. japonicum* USDA 127, *B. japonicum* USDA 129 and/or *B. japonicum* USDA 532C), one or more *Rhizobium* extracts (e.g., an extract of media comprising *R. leguminosarum* SO12A-2), one or more *Sinorhizobium* extracts (e.g., an extract of media comprising *S. fredii* CCBAU114 and/or *S. fredii* USDA 205), one or more *Penicillium* extracts (e.g., an extract of media comprising *P. bilaiae* ATCC 18309, *P. bilaiae* ATCC 20851, *P. bilaiae* ATCC 22348, *P. bilaiae* NRRL 50162, *P. bilaiae* NRRL 50169, *P. bilaiae* NRRL 50776, *P. bilaiae* NRRL 50777, *P. bilaiae* NRRL 50778, *P. bilaiae* NRRL 50777, *P. bilaiae* NRRL 50778, *P. bilaiae* NRRL 50779, *P. bilaiae* NRRL 50780, *P. bilaiae* NRRL 50781, *P. bilaiae* NRRL 50782, *P. bilaiae* NRRL 50783, *P. bilaiae* NRRL 50784, *P. bilaiae* NRRL 50785, *P. bilaiae* NRRL 50786, *P. bilaiae* NRRL 50787, *P. bilaiae* NRRL 50788, *P. bilaiae* RS7B-SD1, *P. brevicompactum* AgRF18, *P. canescens* ATCC 10419, *P. expansum* ATCC 24692, *P. expansum* YT02, *P. fellatanum* ATCC 48694, *P. gaestrivorus* NRRL 50170, *P. glabrum* DAOM 239074, *P. glabrum* CBS 229.28, *P. janthinellum* ATCC 10455, *P. lanosocoeruleum* ATCC 48919, *P. radicum* ATCC 201836, *P. radicum* FRR 4717, *P. radicum* FRR 4719, *P. radicum* N93/47267 and/or *P. raistrickii* ATCC 10490), one or more *Pseudomonas* extracts (e.g., an extract of media comprising *P. jessenii* PS06), one or more acaricidal, insecticidal and/or nematicidal extracts (e.g., an extract of media comprising *Bacillus firmus* 1-1582, *Bacillus mycoides* AQ726, NRRL B-21664; *Beauveria bassiana* ATCC-74040, *Beauveria bassiana* ATCC-74250, *Burkholderia* sp. A396 sp. nov. rinojensis, NRRL B-50319, *Chromobacterium subtsugae* NRRL B-30655, *Chromobacterium vaccinii* NRRL B-50880, *Flavobacterium* H492, NRRL B-50584, *Metarhizium anisopliae* F52 (also known as *Metarhizium anisopliae* strain 52, *Metarhizium anisopliae* strain 7, *Metarhizium anisopliae* strain 43 and *Metarhizium anisopliae* BIO-1020, TAE-001; deposited as DSM 3884, DSM 3885, ATCC 90448, SD 170 and ARSEF 7711) and/or *Paecilomyces fumosoroseus* FE991), and/or one or more fungicidal extracts (e.g., an extract of media comprising *Ampelomyces quisqualis* AQ 100 (Intrachem Bio GmbH & Co. KG, Germany), *Aspergillus flavus* AFLA-GUARD® (Syngenta Crop Protection, Inc., CH), *Aureobasidium pullulans* BOTECTOR® (bio-ferm GmbH, Germany), *Bacillus pumilus* AQ717 (NRRL B-21662), *Bacillus pumilus* NRRL B-30087, *Bacillus* AQ175 (ATCC 55608), *Bacillus* AQ177 (ATCC 55609), *Bacillus subtilis* AQ713 (NRRL B-21661), *Bacillus subtilis* AQ743 (NRRL B-21665), *Bacillus amyloliquefaciens* FZB24, *Bacillus amyloliquefaciens* NRRL B-50349, *Bacillus amyloliquefaciens* TJ1000 (also known as 1BE, isolate ATCC BAA-390), *Bacillus thuringiensis* AQ52 (NRRL B-21619), *Candida oleophila* 1-82 (e.g., ASPIRE® from Ecogen Inc., USA), *Candida saitoana* BIO-CURE® (in mixture with lysozyme; BASF, USA) and BIOCOAT® (AiystaLife Science, Ltd., Cary, N.C.), *Clonostachys rosea* f *catenulata* (also referred to as *Gliocladium catenulatum*) J1446 (PRESTOP®, Verdera, Finland), *Coniothyrium minitans* CONTANS® (Prophyta, Germany), *Cryphonectria parasitica* (CNICM, France), *Cryptococcus albidus* YIELD PLUS® (Anchor Bio-Technologies, South Africa), *Fusarium oxysporum* BIOFOX® (from S.I.A.P.A., Italy) and FUSACLEAN® (Natural Plant Protection, France), *Metschnikowia fructicola* SHEMER® (Agrogreen, Israel), *Microdochium dimerum* ANTIBOT® (Agrauxine, France), *Muscodor albus* NRRL 30547, *Muscodor roseus* NRRL 30548, *Phlebiopsis gigantea* ROTSOP® (Verdera, Finland), *Pseudozyma flocculosa* SPORODEX® (Plant Products Co. Ltd., Canada), *Pythium oligandrum* DV74 (POLYVERSUM®, Remeslo SSRO, Biopreparaty, Czech Rep.), *Reynoufria sachlinensis* (e.g., REGALIA® from Marrone BioInnovations, USA), *Streptomyces* NRRL B-30145, *Streptomyces* M1064, *Sfreptomyces galbus* NRRL 30232, *Streptomyces lydicus* WYEC 108 (ATCC 55445), *Streptomyces violaceusniger* YCED 9 (ATCC 55660; DE-THATCH-9®, DECOMP-9® and THATCH CONTROL®, Idaho Research Foundation, USA), *Streptomyces* WYE 53 (ATCC 55750; DE-THATCH-9®, DECOMP-90 and THATCH CONTROL®, Idaho Research Foundation, USA), *Talaromyces flavus* V117b (PROTUS®, Prophyta, Germany), *Trichoderma asperellum* SKT-1 (ECO-HOPE®, Kumiai Chemical Industry Co., Ltd., Japan), *Trichoderma atroviride* LC52 (SENTINEL®, Agrimm Technologies Ltd, NZ), *Trichoderma harzianum* T-22 (PLANTSHIELD®, der *Firma* BioWorks Inc., USA), *Trichoderma harzianum* TH-35 (ROOT PRO®, from Mycontrol Ltd., Israel), *Trichoderma harzianum* T-39 (TRICHODEX®, Mycontrol Ltd., Israel; *TRICHODERMA* 2000®, Makhteshim Ltd., Israel), *Trichoderma harzianum* ICC012 and *Trichoderma viride* TRICHOPEL (Agrimm Technologies Ltd, NZ), *Trichoderma harzianum* ICC012 and *Trichoderma viride* ICC080 (REMEDIER® WP, Isagro Ricerca, Italy), *Trichoderma polysporum* and *Trichoderma harzianum* (BINAB®, BINAB Bio-Innovation AB, Sweden), *Trichoderma stromaticum* TRICOVAB® (C.E-.P.L.A.C., Brazil), *Trichoderma virens* GL-21 (SOIL-GARD®, Certis LLC, USA), *Trichoderma virens* G1-3, ATCC 57678, *Trichoderma virens* G1-21 (Thermo Trilogy Corporation, Wasco, Calif.), *Trichoderma virens* G1-3 and *Bacillus amyloliquefaciens* FZB2, *Trichoderma virens* G1-3 and *Bacillus amyloliquefaciens* NRRL B-50349, *Trichoderma virens* G1-3 and *Bacillus amyloliquefaciens* TJ1000, *Trichoderma virens* G1-21 and *Bacillus amyloliquefaciens* FZB24, *Trichoderma virens* G1-21 and *Bacillus amyloliquefaciens* NRRL B-50349, *Trichoderma virens* G1-21 and *Bacillus amyloliquefaciens* TJ1000, *Trichoderma viride* TRIECO® (Ecosense Labs. (India) Pvt. Ltd., Indien, BIO-CURE® F from T. Stanes & Co. Ltd., Indien), *Trichoderma viride* TV1 (Agribiotec srl, Italy), *Trichoderma viride* ICC080, and/or *Ulocladium oudemansii* HRU3 (BOTRY-ZEN®, Botry-Zen Ltd, NZ)).

Microbial extracts may be incorporated into inoculant compositions of the present disclosure in any suitable amount(s)/concentration(s). In some embodiments, the microbial extract(s) comprise(s) about 0.01 to about 5% (by weight) of the inoculant composition. For example, inoculant compositions of the present disclosure may comprise about 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% or more (by weight) of one or more microbial extracts. In some embodiments, the microbial extract(s) comprise(s) about 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1 to about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% (by weight) of the inoculant composition.

Inoculant compositions of the present disclosure may comprise any suitable nutrient(s), including, but not limited to, organic acids (e.g., acetic acid, citric acid, lactic acid, malic acid, taurine, etc.), macrominerals (e.g., phosphorous, calcium, magnesium, potassium, sodium, iron, etc.), trace minerals (e.g., boron, cobalt, chloride, chromium, copper, fluoride, iodine, iron, manganese, molybdenum, selenium, zinc, etc.), vitamins, (e.g., vitamin A, vitamin B complex (i.e., vitamin $B_1$, vitamin $B_2$, vitamin $B_3$, vitamin $B_5$, vitamin $B_6$, vitamin $B_7$, vitamin $B_8$, vitamin $B_9$, vitamin $B_{12}$, choline) vitamin C, vitamin D, vitamin E, vitamin K, carotenoids ($\alpha$-carotene, $\beta$-carotene, cryptoxanthin, lutein, lycopene, zeaxanthin, etc.) and combinations thereof. In some embodiments, inoculant compositions of the present disclosure comprise phosphorous, boron, chlorine, copper, iron, manganese, molybdenum and/or zinc.

Inoculant compositions of the present disclosure may comprise any suitable pesticide(s), including, but not limited to, fungicides, herbicides, insecticides, and nematicides. In some embodiments, inoculant compositions of the present disclosure comprise one or more biopesticides (e.g., one or more biofungicides, bioinsecticides and/or bionematicides).

Inoculant compositions of the present disclosure may comprise any suitable insecticide(s), including, but not limited to, biological insecticides and chemical insecticides. Insecticides may be selected so as to provide effective control against a broad spectrum of insects, including, but not limited to, insects from the orders Coleoptera, Dermaptera, Diptera, Hemiptera, Homoptera, Hymenoptera, Lepidoptera, Orthoptera and Thysanoptera. For example, inoculant compositions of the present disclosure may comprise one or more insecticides toxic to insects from the families Acrididae, Aleytodidae, Anobiidae, Anthomyiidae, Aphididae, Bostrichidae, Bruchidae, Cecidomyiidae, Cerambycidae, Cercopidae, Chiysomelidae, Cicadellidae, Coccinellidae, Cryllotalpidae, Cucujidae, Curculionidae, Dermestidae, Elateridae, Gelechiidae, Lygaeidae, Meloidae, Membracidae, Miridae, Noctuidae, Pentatomidae, Pyralidae, Scarabaeidae, Silvanidae, Spingidae, Tenebrionidae and/or Thripidae.

In some embodiments, inoculant compositions of the present disclosure comprise an insecticide (or combination of insecticides) that is toxic to one or more species of *Acalymma*, *Acanthaoscelides* (e.g., *A. obtectus*), *Anasa* (e.g., *A. tristis*), *Anastrepha* (e.g., *A. ludens*), *Anoplophora* (e.g., *A. glabripennis*), *Anthonomus* (e.g., *A. eugenii*), *Acyrthosiphon* (e.g., *A. pisum*), *Bactrocera* (e.g. *B. dosalis*), *Bemisia* (e.g., *B. argentifolii*, *B. tabaci*), *Brevicoryne* (e.g., *B. brassicae*), *Bruchidius* (e.g., *B. afrolineatus*), *Bruchus* (e.g., *B. atomarius*, *B. dentipes*, *B. lentis*, *B. pisorum* and/or *B. rufipes*), *Callosobruchus* (e.g., *C. chinensis*, *C. maculatus*, *C. rhodesianus*, *C. subinnotatus*, *C. theobromae*), *Caryedon* (e.g., *C. serratus*), *Cassadinae*, *Ceratitis* (e.g., *C. capitata*), *Chrysomelinae*, *Circulifer* (e.g., *C. tenellus*), *Criocerinae*, *Cryptocephalinae*, *Cryptolestes* (e.g., *C. ferrugineus*, *C. pusillis*, *C. pussilloides*), *Cylas* (e.g., *C. formicarius*), *Delia* (e.g., *D. antiqua*), *Diabrotica*, *Diaphania* (e.g., *D. nitidalis*), *Diaphorina* (e.g., *D. citri*), *Donaciinae*, *Ephestia* (e.g, *E. cautella*, *E. elutella*, *E., keuhniella*), *Epilachna* (e.g., *E. varivesfris*), *Epiphyas* (e.g., *E. postvittana*), *Eumolpinae*, *Galerucinae*, *Helicoverpa* (e.g., *H. zea*), *Heteroligus* (e.g., *H. meles*), *Iobesia* (e.g., *I. bofrana*), *Lamprosomatinae*, *Lasioderma* (e.g., *L. serricorne*), *Leptinotarsa* (e.g., *L. decemlineata*), *Leptoglossus*, *Liriomyza* (e.g., *L. trifolii*), *Manducca*, *Melittia* (e.g., *M. cucurbitae*), *Myzus* (e.g., *M. persicae*), *Nezara* (e.g., *N. viridula*), *Orzaephilus* (e.g., *O. merator*, *O. surinamensis*), *Ostrinia* (e.g., *O. nubilalis*), *Phthorimaea* (e.g., *P. operculella*), *Pieris* (e.g., *P. rapae*), *Plodia* (e.g., *P. interpunctella*), *Plutella* (e.g., *P. xylostella*), *Popillia* (e.g., *P. japonica*), *Prostephanus* (e.g., *P. truncates*), *Psila*, *Rhizopertha* (e.g., *R. dominica*), *Rhopalosiphum* (e.g., *R. maidis*), *Sagrinae*, *Solenopsis* (e.g., *S. Invicta*), *Spilopyrinae*, *Sitophilus* (e.g., *S. granaries*, *S. oryzae* and/or *S. zeamais*), *Sitofroga* (e.g., *S. cerealella*), *Spodoptera* (e.g., *S. frugiperda*), *Stegobium* (e.g., *S. paniceum*), *Synetinae*, *Tenebrio* (e.g., *T. malens* and/or *T. molitor*), *Thrips* (e.g., *T. tabaci*), *Trialeurodes* (e.g., *T. vaporariorum*), *Tribolium*

(e.g., *T. castaneum* and/or *T. confusum*), *Trichoplusia* (e.g., *T. ni*), *Trogoderma* (e.g., *T. granarium*) and *Trogossitidae* (e.g., *T. mauritanicus*).

Additional species of insects that may be targeted by inoculant compositions of the present disclosure may be found in CAPINERA, HANDBOOK OF VEGETABLE PESTS (2001) and Steffey and Gray, *Managing Insect Pests*, in ILLINOIS AGRONOMY HANDBOOK (2008).

Inoculant compositions of the present disclosure may comprise any suitable nematicide(s) including, but not limited to, biological nematicides and chemical nematicides. Nematicides may be selected so as to provide effective control against a broad spectrum of nematodes, including, but not limited to, phytoparasitic nematodes from the classes Chromadorea and Enoplea.

In some embodiments, inoculant compositions of the present disclosure comprise a nematicide (or combination of nematicides) that is toxic to one or more strains of *Anguina, Aphelenchoides, Belonolaimus, Bursaphelenchus, Ditylenchus, Globodera, Helicotylenchus, Heterodera, Hirschmanniella, Meloidogyne, Naccobus, Pratylenchus, Radopholus, Rotylenshulus, Trichodorus, Tylenchulus* and/or *Xiphinema*.

Additional examples of nematodes that may be targeted by inoculant compositions of the present disclosure may be found in CAPINERA, HANDBOOK OF VEGETABLE PESTS (2001) and Niblack, *Nematodes*, in ILLINOIS AGRONOMY HANDBOOK (2008).

As discussed above, inoculant compositions of the present disclosure may comprise one or more biological insecticides and/or nematicides (i.e., one or more microorganisms the presence and/or output of which is toxic to an acarid, insect and/or nematode).

In some embodiments, inoculant compositions of the present disclosure comprise one or more chemical insecticides and/or nematicides. For example, in some embodiments, inoculant compositions of the present disclosure comprise one or more carbamates, diamides, macrocyclic lactones, neonicotinoids, organophosphates, phenylpyrazoles, pyrethrins, spinosyns, synthetic pyrethroids, tetronic acids and/or tetramic acids.

Non-limiting examples of chemical insecticides and nematicides that may be useful in inoculant compositions of the present disclosure include acrinathrin, alpha-cypermethrin, betacyfluthrin, cyhalothrin, cypermethrin, deltamethrin, csfenvalcrate, etofenprox, fenpropathrin, fenvalerate, flucythrinate, fosthiazate, lambda-cyhalothrin, gamma-cyhalothrin, permethrin, tau-fluvalinate, transfluthrin, zeta-cypermethrin, cyfluthri, bifenthrin, tefluthrin, eflusilanat, fubfenprox, pyrethrin, resmethrin, imidacloprid, acetamiprid, thiamethoxam, nitenpyram, thiacloprid, dinotefuran, clothianidin, imidaclothiz, chlorfluazuron, diflubenzuron, lufenuron, teflubenzuron, triflumuron, novaluron, flufenoxuron, hexaflumuron, bistrifluoron, noviflumuron, buprofezin, cyromazine, methoxyfenozide, tebufenozide, halofenozide, chromafenozide, endosulfan, fipronil, ethiprole, pyrafluprole, pyriprole, flubendiamide, chlorantraniliprole (e.g., *Rynaxypyr*), cyazypyr, emamectin, emamectin benzoate, abamectin, ivermectin, milbemectin, lepimectin, tebufenpyrad, fenpyroximate, pyridaben, fenazaquin, pyrimidifen, tolfenpyrad, dicofol, cyenopyrafen, cyflumetofen, acequinocyl, fluacrypyrin, bifenazate, diafenthiuron, etoxazole, clofentezine, spinosad, triarathen, tetradifon, propargite, hexythiazox, bromopropylate, chinomethionat, amitraz, pyrifluquinazon, pymetrozine, flonicamid, pyriproxyfen, diofenolan, chlorfenapyr, metaflumizone, indoxacarb, chlorpyrifos, spirodiclofen, spiromesifen, spirotetramat, pyridalyl, spinctoram, acephate, triazophos, profenofos, oxamyl, spinetoram, fenamiphos, fenamipclothiahos, 4-{[(6-chloropyrid-3-yl)methyl](2,2-difluoroethyl)amino}furan-2(5H)-one, cadusaphos, carbaryl, carbofuran, ethoprophos, thiodicarb, aldicarb, aldoxycarb, metamidophos, methiocarb, sulfoxaflor, cyantraniliprole and tioxazafen and combinations thereof. In some embodiments, inoculant compositions of the present disclosure comprise abamectin, aldicarb, aldoxycarb, bifenthrin, carbofuran, chlorantraniliporle, chlothianidin, cyfluthrin, cyhalothrin, cypermethrin, cyantraniliprole, deltamethrin, dinotefuran, emamectin, ethiprole, fenamiphos, fipronil, flubendiamide, fosthiazate, imidacloprid, ivermectin, lambda-cyhalothrin, milbemectin, nitenpyram, oxamyl, permethrin, spinetoram, spinosad, spirodichlofen, spirotetramat, tefluthrin, thiacloprid, thiamethoxam and/or thiodicarb. In some embodiments, inoculant compositions of the present disclosure comprise an insecticide selected from the group consisting of clothianidin, thiamethoxam, imidacloprid, cyantraniliprole, chlorantraniliprole, fluopyram and tioxazafen.

Additional examples of insecticides and nematicides that may be included in inoculant compositions of the present disclosure may be found in Steffey and Gray, *Managing Insect Pests*, in ILLINOIS AGRONOMY HANDBOOK (2008) and Niblack, *Nematodes*, in ILLINOIS AGRONOMY HANDBOOK (2008).

In some embodiments, inoculant compositions of the present disclosure comprise one or more commercial insecticides and nematicides used in accordance with the manufacturer's recommended amounts/concentrations.

Inoculant compositions of the present disclosure may comprise any suitable fungicide(s), including, but not limited to, biological fungicides and chemical fungicides. Fungicides may be selected so as to provide effective control against a broad spectrum of phytopathogenic fungi (and fungus-like organisms), including, but not limited to, soil-borne fungi from the classes Ascomycetes, Basidiomycetes, Chytridiomycetes, Deuteromycetes (syn. Fungi imperfecti), Peronosporomycetes (syn. Oomycetes), Plasmodiophoromycetes and Zygomycetes.

In some embodiments, inoculant compositions of the present disclosure comprise a fungicide (or combination of fungicides) that is toxic to one or more strains of *Albugo* (e.g., *A. candida*), *Alternaria* (e.g. *A. alternata*), *Aspergillus* (e.g., *A. candidus, A. clavatus, A. flavus, A. fumigatus, A. parasiticus, A. resfrictus, A. sojae, A. solani*), *Blumeria* (e.g., *B. graminis*), *Botrytis* (e.g., *B. cinerea*), *Cladosporum* (e.g., *C. cladosporioides*), *Colletotrichum* (e.g., *C. acutatum, C. boninense, C. capsici, C. caudatum, C. coccodes, C. crassipes, C. dematium, C. desfructivum, C. fragariae, C. gloeosporioides, C. graminicola, C. kehawee, C. lindemuthianum, C. musae, C. orbiculare, C. spinaceae, C. sublineolum, C. trifolii, C. truncatum*), *Fusarium* (e.g., *F. graminearum, F. moniliforme, F. oxysporum, F. roseum, F. tricinctum*), *Helminthosporium, Magnaporthe* (e.g., *M. grisea, M. oryzae*), *Melamspora* (e.g., *M. lini*), *Mycosphaerella* (e.g., *M. graminicola*), *Nematospora, Penicillium* (e.g., *P. rugulosum, P. verrucosum*), *Phakopsora* (e.g., *P. pachyrhizi*), *Phomopsis, Phytiphtoria* (e.g., *P. infestans*), *Puccinia* (e.g., *P. graminis, P. striiformis, P. tritici, P. friticina*), *Pucivinia* (e.g., *P. graministice*), *Pythium, Pytophthora, Rhizoctonia* (e.g., *R. solani*), *Scopulariopsis, Selerotinia, Thielaviopsis* and/or *Ustilago* (e.g., *U. maydis*).

Additional examples of fungi that may be targeted by inoculant compositions of the present disclosure may be found in Bradley, *Managing Diseases*, in ILLINOIS AGRONOMY HANDBOOK (2008).

As discussed above, inoculant compositions of the present disclosure may comprise one or more biological fungicides (i.e., one or more microorganisms the presence and/or output of which is toxic to a fungus).

In some embodiments, inoculant compositions of the present disclosure comprise one or more chemical fungicides. For example, in some embodiments, inoculant compositions of the present disclosure comprise one or more aromatic hydrocarbons, benzimidazoles, benzthiadiazole, carboxamides, carboxylic acid amides, morpholines, phenylamides, phosphonates, quinone outside inhibitors (e.g. strobilurins), thiazolidines, thiophanates, thiophene carboxamides and/or triazoles.

Non-limiting examples of chemical fungicides that may be useful in inoculant compositions of the present disclosure include strobilurins, such as azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl)-phenyl)-2-methoxyimino-N-methyl-acetamide; carboxamides, such as carboxanilides (e.g., benalaxyl, benalaxyl-M, benodanil, bixafen, boscalid, carboxin, fenfuram, fenhexamid, flutolanil, fluxapyroxad, furametpyr, isopyrazam, isotianil, kiralaxyl, mepronil, metalaxyl, metalaxyl-M (mefenoxam), ofurace, oxadixyl, oxycarboxin, penflufen, penthiopyrad, sedaxane, tecloftalam, thifluzamide, tiadinil, 2-amino-4-methyl-thiazole-5-carboxanilide, N-(4'-trifluoromethylthiobiphenyl-2-yl)-3-difluoromethyl-1-methy 1H-pyra-zole-4-carboxamide, N-(2-(1,3,3-trimethylbutyl)-phenyl)-1,3-dimethyl-5-fluoro-1H-pyrazole-4-carboxamide), carboxylic morpholides (e.g., dimethomorph, flumorph, pyrimorph), benzoic acid amides (e.g., flumetover, fluopicolide, fluopyram, zoxamide), carpropamid, dicyclomet, mandiproamid, oxytetracyclin, silthiofam and N-(6-methoxy-pyridin-3-yl) cyclopropanecarboxylic acid amide; azoles, such as triazoles (e.g., azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole) and imidazoles (e.g., cyazofamid, imazalil, pefurazoate, prochloraz, triflumizol); heterocyclic compounds, such as pyridines (e.g., fluazinam, pyrifenox (cf.D1b), 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine), pyrimidines (e.g., bupirimate, cyprodinil, diflumetorim, fenarimol, ferimzone, mepanipyrim, nitrapyrin, nuarimol, pyrimethanil), piperazines (e.g., triforine), pirroles (e.g., fenpiclonil, fludioxonil), morpholines (e.g., aldimorph, dodemorph, dodemorph-acetate, fenpropimorph, tridemorph), piperidines (e.g., fenpropidin); dicarboximides (e.g., fluoroimid, iprodione, procymidone, vinclozolin), non-aromatic 5-membered heterocycles (e.g., famoxadone, fenamidone, flutianil, octhilinone, probenazole, 5-amino-2-isopropyl-3-oxo-4-ortho-tolyl-2,3-dihydro-pyrazole-1-carbothioic acid S-allyl ester), acibenzolar-S-methyl, ametoctradin, amisulbrom, anilazin, blasticidin-S, captafol, captan, chinomethionat, dazomet, debacarb, diclomezine, difenzoquat, difenzoquat-methylsulfate, fenoxanil, Folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole and 5-chloro-7-(4-methyl)piperidin-1-yl)-6-(2,4,6-trifluorophenyl)-[1,2,4]triazolo-[1,5-a]pyrimidine; benzimidazoles, such as carbendazim; and other active substances, such as guanidines (e.g., guanidine, dodine, dodine free base, guazatine, guazatine-acetate, iminoctadine), iminoctadine-triacetate and iminoctadine-tris(albesilate); antibiotics (e.g., kasugamycin, kasugamycin hydrochloride-hydrate, streptomycin, polyoxine and validamycin A), nitrophenyl derivates (e.g., binapacryl, dicloran, dinobuton, dinocap, nitrothal-isopropyl, tecnazen). organometal compounds (e.g., fentin salts, such as fentin-acetate, fentin chloride, fentin hydroxide); sulfur-containing heterocyclyl compounds (e.g., dithianon, isoprothiolane), organophosphorus compounds (e.g., edifenphos, fosetyl, fosetyl-aluminum, iprobenfos, phosphorus acid and its salts, pyrazophos, tolclofos-methyl), organochlorine compounds (e.g., chlorothalonil, dichlofluanid, dichlorophen, flusulfamide, hexachlorobenzene, pencycuron, pentachlorphenole and its salts, phthalide, quintozene, thiophanate-methyl, thiophanate, tolylfluanid, N-(4-chloro-2-nitro-phenyl)-N-ethyl-4-methyl-benzenesulfonamide) and inorganic active substances (e.g., Bordeaux mixture, copper acetate, copper hydroxide, copper oxychloride, basic copper sulfate, sulfur) and combinations thereof. In some embodiments, inoculant compositions of the present disclosure comprise acibenzolar-S-methyl, azoxystrobin, benalaxyl, bixafen, boscalid, carbendazim, cyproconazole, dimethomorph, epoxiconazole, fludioxonil, fluopyram, fluoxastrobin, flutianil, flutolanil, fluxapyroxad, fosetyl-A1, ipconazole, isopyrazam, kresoxim-methyl, mefenoxam, metalaxyl, metconazole, myclobutanil, orysastrobin, penflufen, penthiopyrad, picoxystrobin, propiconazole, prothioconazole, pyraclostrobin, sedaxane, silthiofam, tebuconazole, thiabendazole, thifluzamide, thiophanate, tolclofos-methyl, trifloxystrobin and triticonazole. In some embodiments, inoculant compositions of the present disclosure comprise azoxystrobin, pyraclostrobin, fluoxastrobin, trifloxystrobin, ipconazole, prothioconazole, sedaxane, fludioxonil, metalaxyl, mefenoxam, thiabendazole, fluxapyroxad and/or fluopyram.

Additional examples of fungicides that may be included in inoculant compositions of the present disclosure may be found in Bradley, *Managing Diseases*, in *ILLINOIS AGRONOMY HANDBOOK* (2008).

In some embodiments, inoculant compositions of the present disclosure comprise one or more commercial fungicides used in accordance with the manufacturer's recommended amounts/concentrations.

Inoculant compositions of the present disclosure may comprise any suitable herbicide(s), including, but not limited to, biological herbicides and chemical herbicides. Herbicides may be selected so as to provide effective control against a broad spectrum of plants, including, but not limited to, plants from the families Asteraceae, Caryophyllaceae, Poaceae and Polygonaceae.

In some embodiments, inoculant compositions of the present disclosure comprise an herbicide (or combination of herbicides) that is toxic to one or more strains of *Echinochloa* (e.g., *E. brevipedicellata, E. callopus, E. chacoensis, E. colona, E. crus-galli, E. crus-pavonis, E. elliptica, E. esculenta, E. frumentacea, E. glabrescens, E. haploclada, E. helodes, E. hokiformis, E. inundata, E. jaliscana, E. Jubata, E. kimberleyensis, E. lacunaria, E. macrandra, E. muricata, E. obtusiflora, E. oplismenoides, E. orzyoides, E. paludigena, E. picta, E. pithopus, E. polystachya, E. praestans, E. pyramidalis, E. rotundiflora, E. stagnina, E. telmatophila, E. turneriana, E. ugandensis, E. walteri*), *Fallopia* (e.g., *F. baldschuanica, F. japonica, F. sachalinensis*), *Stellaria* (e.g., S. media) and/or Taraxacum (e.g., T. albidum, T. aphrogenes, T. brevicorniculatum, T. californicum, T. centrasiatum, T. ceratophorum, T. erythrospermum, T. farinosum, T. holmboei, T. japonicum, T. kok-saghyz, T. laevigatum T. officinale, T. platycarpum).

Additional species of plants that may be targeted by inoculant compositions of the present disclosure may be found in Hager, Weed Management, in ILLINOIS AGRONOMY HANDBOOK (2008) and LOUX ET AL., WEED CONTROL GUIDE FOR OHIO, INDIANA AND ILLINOIS (2015).

As discussed above, inoculant compositions of the present disclosure may comprise one or more biological herbicides (i.e., one or more microorganisms the presence and/or output of which is toxic to a plant).

In some embodiments, inoculant compositions of the present disclosure comprise one or more chemical herbicides. For example, in some embodiments, inoculant compositions of the present disclosure comprise one or more acetyl CoA carboxylase (ACCase) inhibitors, acetolactate synthase (ALS) inhibitors, acetohydroxy acid synthase (AHAS) inhibitors, photosystem II inhibitors, photosystem I inhibitors, protoporphyrinogen oxidase (PPO or Protox) inhibitors, carotenoid biosynthesis inhibitors, enolpyruvyl shikimate-3-phosphate (EPSP) synthase inhibitor, glutamine synthetase inhibitor, dihydropteroate synthetase inhibitor, mitosis inhibitors, 4-hydroxyphenyl-pyruvate-dioxygenase (4-HPPD) inhibitors, synthetic auxins, auxin herbicide salts, auxin transport inhibitors, nucleic acid inhibitors and/or one or more salts, esters, racemic mixtures and/or resolved isomers thereof. Non-limiting examples of chemical herbicides that may be useful in inoculant compositions of the present disclosure include 2,4-dichlorophenoxyacetic acid (2,4-D), 2,4,5-trichlorophenoxyacetic acid (2,4,5-T), ametryn, amicarbazone, aminocyclopyrachlor, acetochlor, acifluorfen, alachlor, atrazine, azafenidin, bentazon, benzofenap, bifenox, bromacil, bromoxynil, butachlor, butafenacil, butroxydim, carfentrazone-ethyl, chlorimuron, chlorotoluro, clethodim, clodinafop, clomazone, cyanazine, cycloxydim, cyhalofop, desmedipham, desmetryn, dicamba, diclofop, dimefuron, diuron, dithiopyr, fenoxaprop, fluazifop, fluazifop-P, fluometuron, flufenpyr-ethyl, flumiclorac-pentyl, flumioxazin, fluoroglycofen, fluthiacet-methyl, fomesafe, fomesafen, glyphosate, glufosinate, haloxyfop, hexazinone, imazamox, imazaquin, imazethapyr, ioxynil, isoproturon, isoxaflutole, lactofen, linuron, mecoprop, mecoprop-P, mesotrione, metamitron, metazochlor, methibenzuron, metolachlor (and S-metolachlor), metoxuron, metribuzin, monolinuron, oxadiargyl, oxadiazon, oxyfluorfen, phenmedipham, pretilachlor, profoxydim, prometon, prometry, propachlor, propanil, propaquizafop, propisochlor, pyraflufen-ethyl, pyrazon, pyrazolynate, pyrazoxyfen, pyridate, quizalofop, quizalofop-P (e.g., quizalofop-ethyl, quizalofop-P-ethyl, clodinafop-propargyl, cyhalofop-butyl, diclofop-methyl, fenoxaprop-P-ethyl, fluazifop-P-butyl, haloxyfop-methyl, haloxyfop-R-methyl), saflufenacil, sethoxydim, siduron, simazine, simetryn, sulcotrione, sulfentrazone, tebuthiuron, tembotrione, tepraloxydim, terbacil, terbumeton, terbuthylazine, thaxtomin (e.g., the thaxtomins described in U.S. Pat. No. 7,989,393), thenylchlor, tralkoxydim, triclopyr, trietazine, tropramezone, salts and esters thereof; racemic mixtures and resolved isomers thereof and combinations thereof. In some embodiments, inoculant compositions of the present disclosure comprise acetochlor, clethodim, dicamba, flumioxazin, fomesafen, glyphosate, glufosinate, mesotrione, quizalofop, saflufenacil, sulcotrione, ethyl 2-((3-(2-chloro-4-fluoro-5-(3-methyl-2,6-dioxo-4-(trifluoromethyl)-2,3-dihydropyrimidin-1(6H)-ypphenoxy)pyridin-2-yl)oxy)acetate and/or 2,4-D. In some embodiments, inoculant compositions of the present disclosure comprise glyphosate, glufosinate, dicamba, 2,4-D, acetochlor, metolachlor, pyroxasulfone, flumioxazin, fomesafen, lactofen, metribuzin, mesotrione, and/or ethyl 2-((3-(2-chloro-4-fluoro-5-(3-methyl-2,6-dioxo-4-(trifluoromethyl)-2,3-dihydropyrimidin-1 (6H)-yl)phenoxy)pyridin-2-yl)oxy)acetate.

Additional examples of herbicides that may be included in inoculant compositions of the present disclosure may be found in Hager, Weed Management, in ILLINOIS AGRONOMY HANDBOOK (2008) and LOUX ET AL., WEED CONTROL GUIDE FOR OHIO, INDIANA AND ILLINOIS (2015).

In some embodiments, inoculant compositions of the present disclosure comprise one or more commercial herbicides used in accordance with the manufacturer's recommended amounts/concentrations.

Inoculant compositions of the present disclosure may comprise any suitable plant signal molecule(s), including, but not limited to, lipo-chitooligosaccharides (LCOs), chitooligosaccharides (COs), chitinous compounds, flavonoids, jasmonic acid or derivatives thereof, linoleic acid or derivatives thereof, linolenic acid or derivatives thereof and karrikins.

Inoculant compositions of the present disclosure may comprise any suitable LCO(s).

LCOs, sometimes referred to as symbiotic nodulation (Nod) signals or Nod factors, consist of an oligosaccharide backbone of β-1,4-linked N-acetyl-D-glucosamine ("GlcNAc") residues with an N-linked fatty acyl chain condensed at the non-reducing end. LCOs differ in the number of GlcNAc residues in the backbone, in the length and degree of saturation of the fatty acyl chain and in the substitutions of reducing and non-reducing sugar residues. See, e.g., Denarie, et al., ANN. REV. BIOCHEM. 65:503 (1996); Hamel, et al., PLANTA 232:787 (2010); Prome, et al., PURE & APDL. CHEM. 70(1):55 (1998).

In some embodiments, inoculant compositions of the present disclosure comprise one or more LCOs represented by formula I:

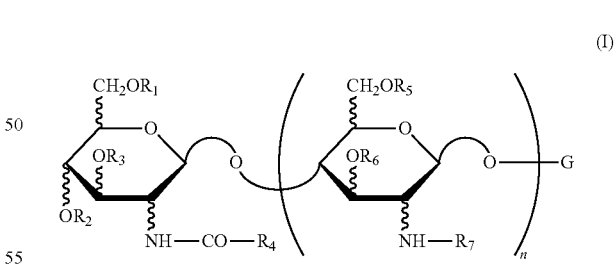

(I)

in which G is a hexosamine which can be substituted, for example, by an acetyl group on the nitrogen, a sulfate group, an acetyl group and/or an ether group on an oxygen; $R_1$, $R_2$, $R_3$, $R_5$, $R_6$ and $R_7$, which may be identical or different, represent H, $CH_3CO-$, $C_x H_y CO-$ where x is an integer between 0 and 17 and y is an integer between 1 and 35, or any other acyl group such as, for example, a carbamoyl; $R_4$ represents a saturated or mono-, di- or tri-unsaturated aliphatic chain containing at least 12 carbon atoms; and n is an integer between 1 and 4.

In some embodiments, inoculant compositions of the present disclosure comprise one or more LCOs represented by formula II:

(II)

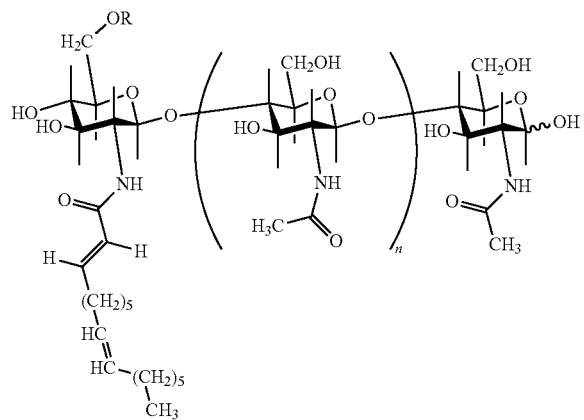

in which R represents H or CH$_3$CO— and n is equal to 2 or 3. See, e.g., U.S. Pat. No. 5,549,718. A number of *Bradyrhizobium japonicum*-derived LCOs have also been described, including BjNod-V (C$_{18:1}$), BjNod-V (A$_C$, C$_{18:1}$), BjNod-V (C$_{16:1}$) and BjNod-V (A$_C$, C$_{16:0}$) (with "V" indicating the presence of five N-acetylglucosamines, "Ac" an acetylation, the number following the "C" indicating the number of carbons in the fatty acid side chain and the number following the ":" indicating the number of double bonds). See, e.g., U.S. Pat. Nos. 5,175,149 and 5,321,011. Additional LCOs obtained from bacterial strains include NodRM, NodRM-1, NodRM-3. When acetylated (the R═CH$_3$CO—), they become AcNodRM-1 and AcNodRM-3, respectively (U.S. Pat. No. 5,545,718).

In some embodiments, inoculant compositions of the present disclosure comprise one or more LCOs represented by formula III:

(III)

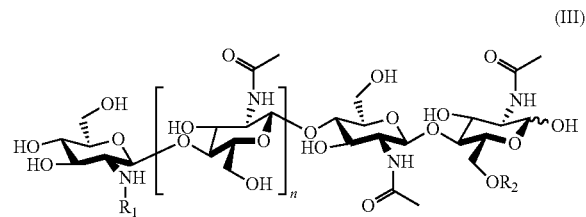

in which n=1 or 2; R$_1$ represents C16, C16:0, C16:1, C16:2, C18:0, C18:1Δ9Z or C18:1Δ11Z; and R$_2$ represents hydrogen or SO$_3$H.

LCOs included in compositions and methods of the present disclosure may be obtained from any suitable source.

In some embodiments, the LCO is obtained (i.e., isolated and/or purified) from a bacterial strain. For example, in some embodiments, inoculant compositions of the present disclosure comprise one or more LCOs obtained from a of *Azorhizobium*, *Bradyrhizobium* (e.g., *B. japonicum*), *Mesorhizobium*, *Rhizobium* (e.g., *R. leguminosarum*), or *Sinorhizobium* (e.g., *S. meliloti*).

In some embodiments, the LCO is obtained (i.e., isolated and/or purified) from a mycorrhizal fungus. For example, in some embodiments, inoculant compositions of the present disclosure comprise one or more LCOs obtained from a strain of Glomerocycota (e.g., *Glomus intraradicus*). See, e.g., WO 2010/049751 (in which the LCOs are referred to as "Myc factors").

In some embodiments, the LCO is synthetic. For example, in some embodiments, inoculant compositions of the present disclosure comprise one or more of the synthetic LCOs described in WO 2005/063784, WO 2007/117500 and/or WO 2008/071674. In some embodiments, the synthetic LCO contains one or more modifications or substitutions, such as those described in Spaink, CRIT. REV. PLANT SCI. 54:257 (2000) and D'Haeze, supra. LCOs and precursors for the construction of LCOs (e.g., COs, which are themselves useful as plant signal molecules) may be synthesized by genetically engineered organisms. See, e.g., Samain et al., CARBOHYDRATE RES. 302:35 (1997); Cottaz, et al., METH. ENG. 7(4):311 (2005); and Samain, et al., J. BIOTECHNOL. 72:33 (1999) (e.g., FIG. 1 therein, which shows structures of COs that can be made recombinantly in *E. coli* harboring different combinations of genes nodBCHL).

Further examples of LCOs (and derivatives thereof) that may be useful in compositions and methods of the present disclosure are provided below as formula IV:

(IV)

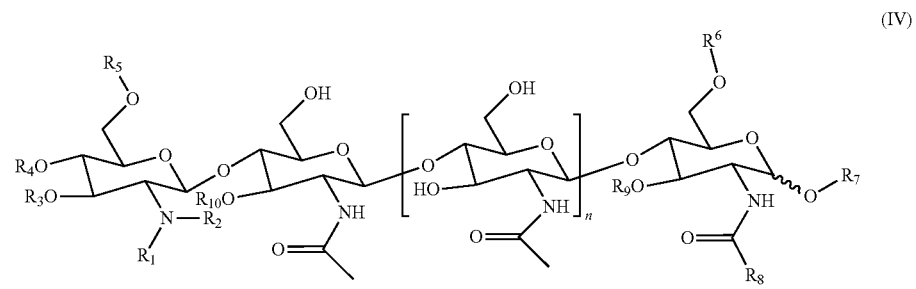

in which $R_1$ represents C14:0, 3OH—C14:0, iso-C15:0, C16:0, 3-OH—C16:0, iso-C15:0, C16:1, C16:2, C16:3, iso-C17:0, iso-C17:1, C18:0, 3OH—C18:0, C18:0/3-OH, C18:1, OH—C18:1, C18:2, C18:3, C18:4, C19:1 carbamoyl, C20:0, C20:1, 3-OH—C20:1, C20:1/3-OH, C20:2, C20:3, C22:1 and C18-26(ω-1)-OH (which according to D'Haeze, et al., Glycobiology 12:79R-105R (2002), includes C18, C20, C22, C24 and C26 hydroxylated species and C16:1Δ9, C16:2 (Δ7,9) and C16:3 (Δ2,4,9)); $R_2$ represents hydrogen or methyl; $R_3$ represents hydrogen, acetyl or carbamoyl; $R_4$ represents hydrogen, acetyl or carbamoyl; $R_5$ represents hydrogen, acetyl or carbamoyl; $R_6$ represents hydrogen, arabinosyl, fucosyl, acetyl, $SO_3H$, sulfate ester, 3-0-S-2-0-MeFuc, 2-0-MeFuc and 4-0-AcFuc; $R_7$ represents hydrogen, mannosyl or glycerol; $R_8$ represents hydrogen, methyl, or —$CH_2OH$; $R_9$ represents hydrogen, arabinosyl, or fucosyl; $R_{10}$ represents hydrogen, acetyl or fucosyl; and n represents 0, 1, 2 or 3. Naturally occurring LCOs embraced by this structure are described in D'Haeze, et al., supra.

Further examples of LCOs (and derivatives thereof) that may be useful in compositions and methods of the present disclosure are provided below as structures V-XXXIII:

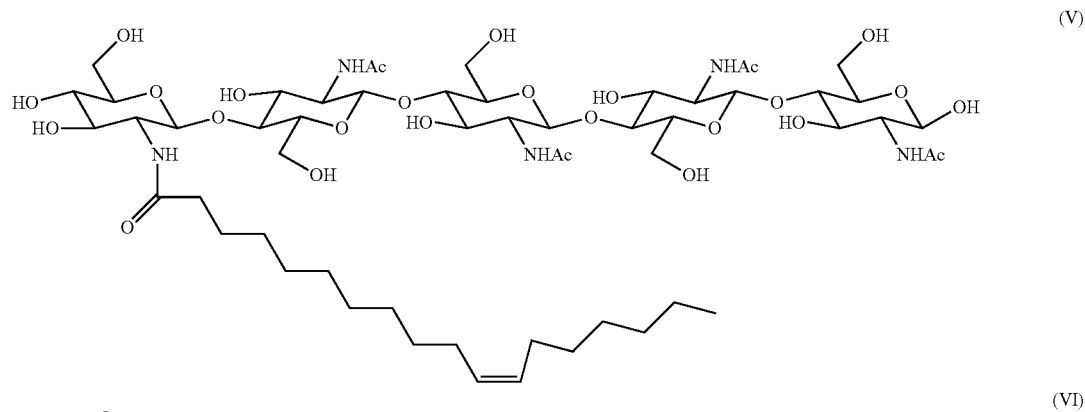

(V)

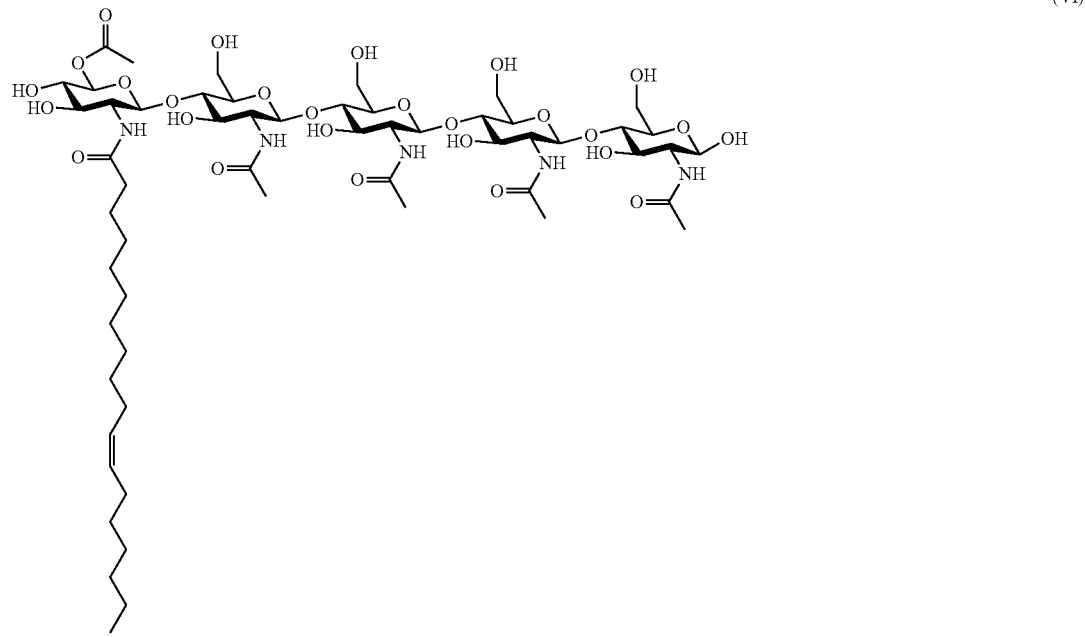

(VI)

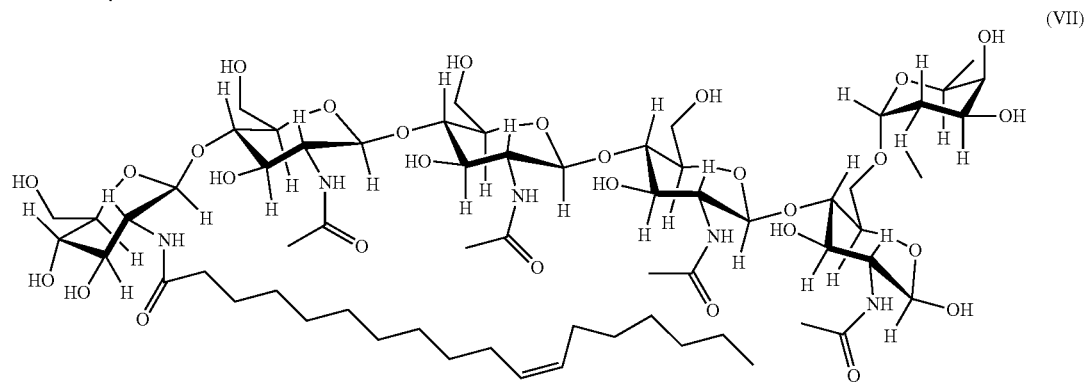

(VII)

-continued
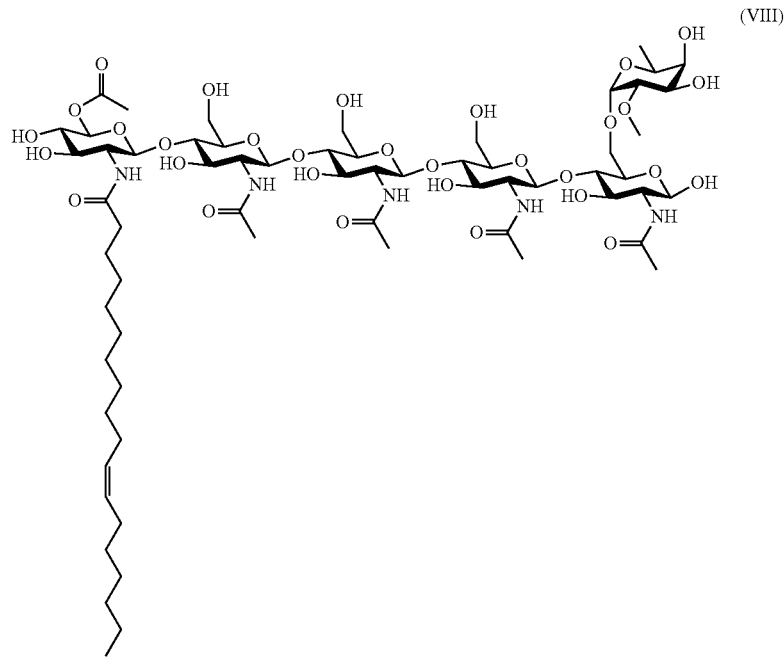
(VIII)
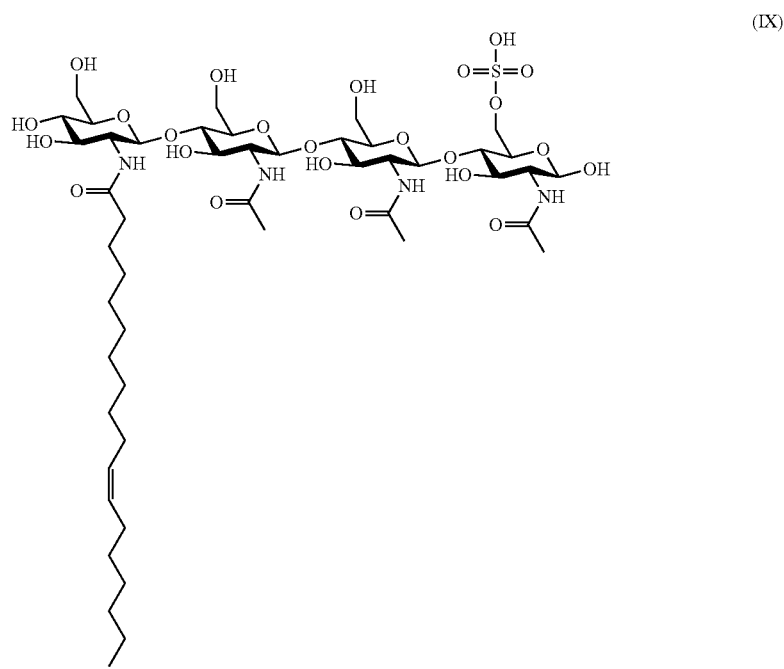
(IX)

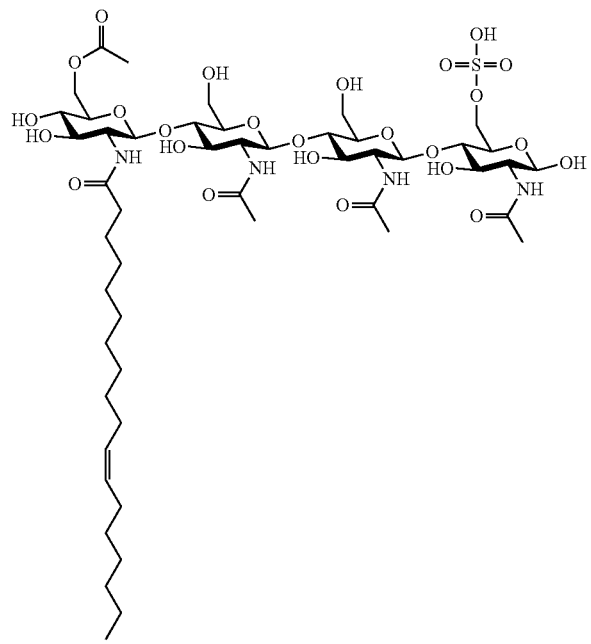
(X)
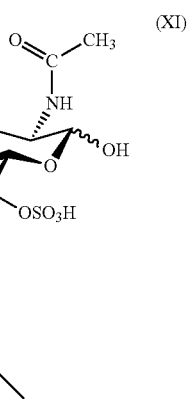
(XI)
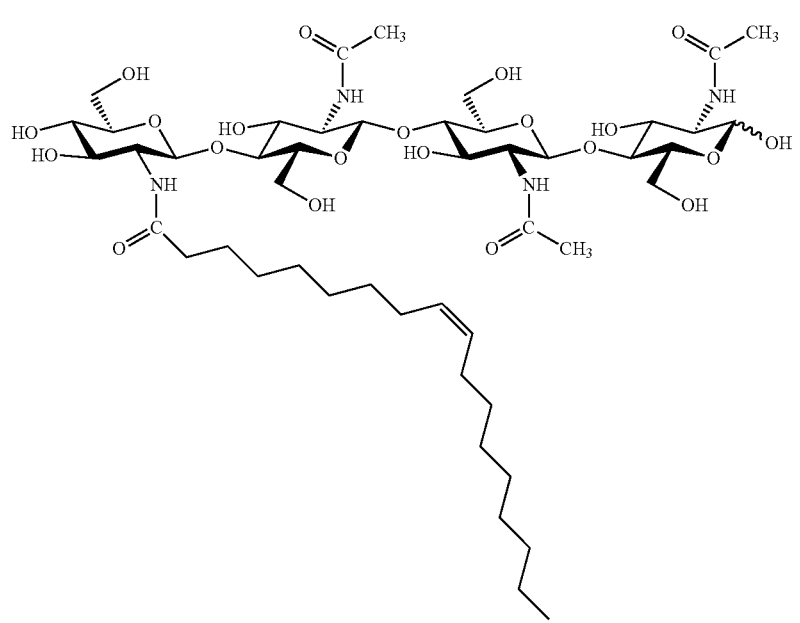
(XII)

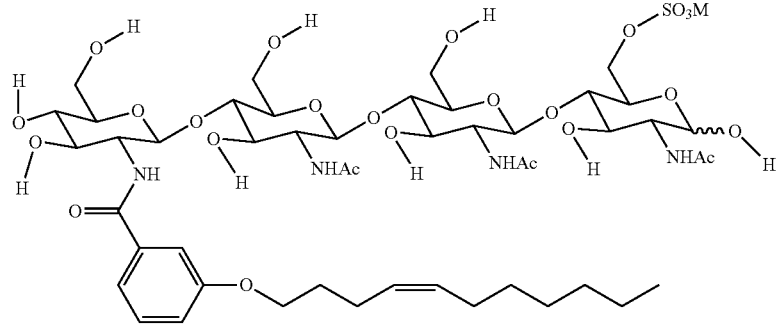
(XIII)
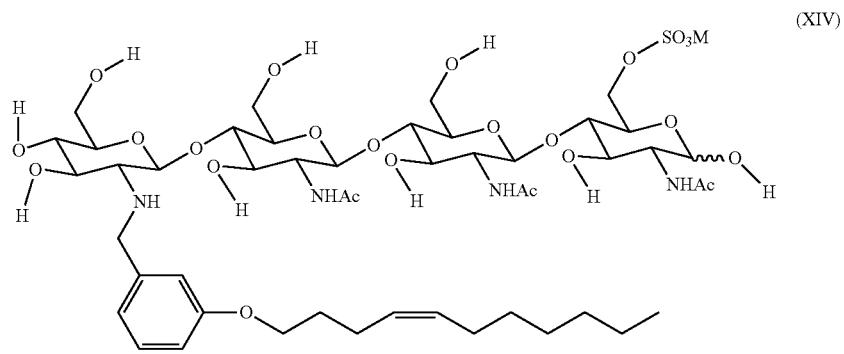
(XIV)
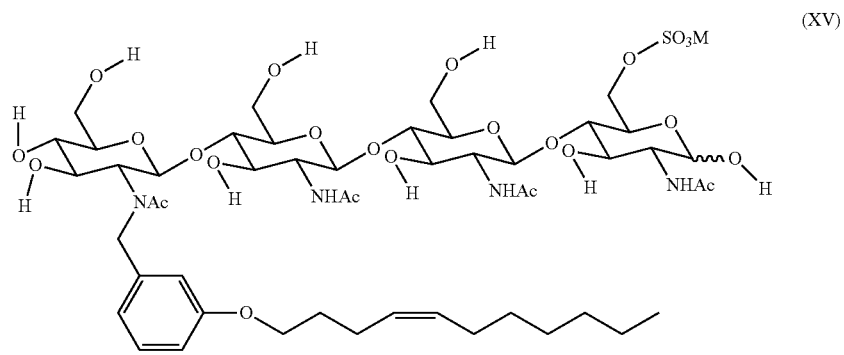
(XV)
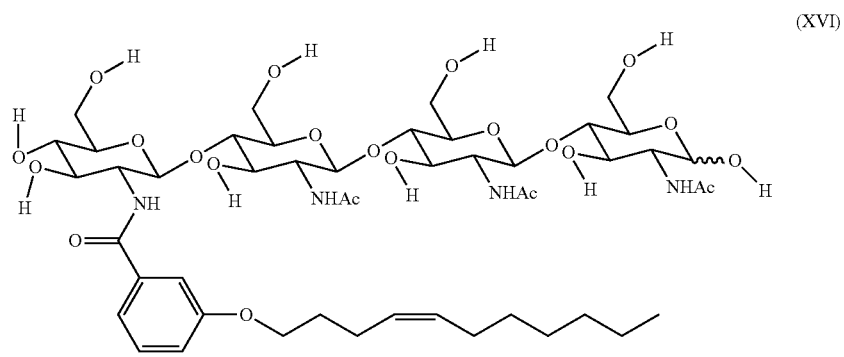
(XVI)

-continued
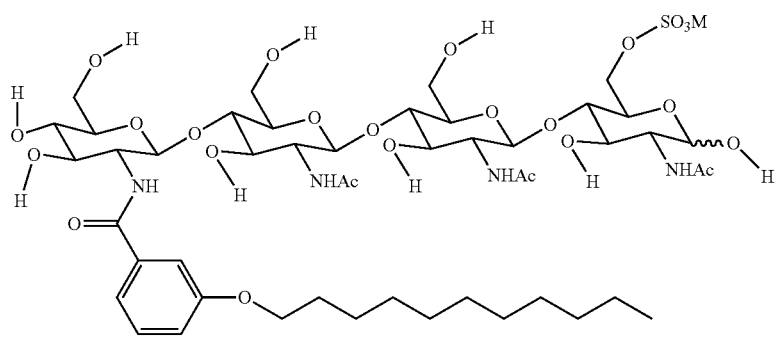
(XVII)
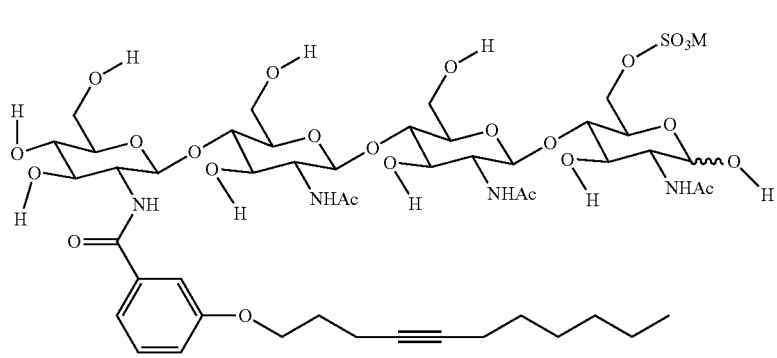
(XVIII)
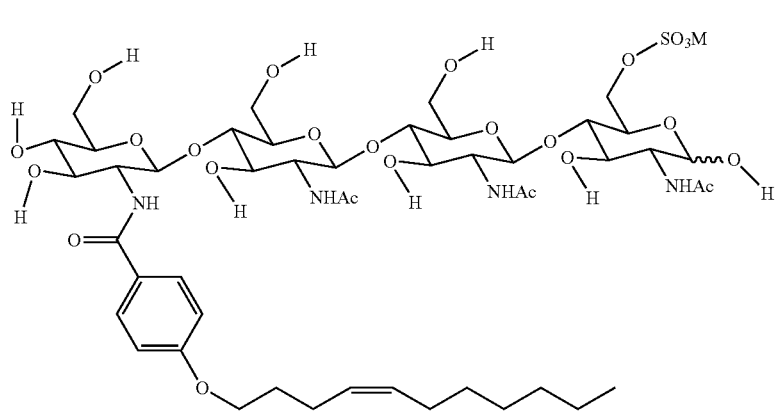
(XIX)
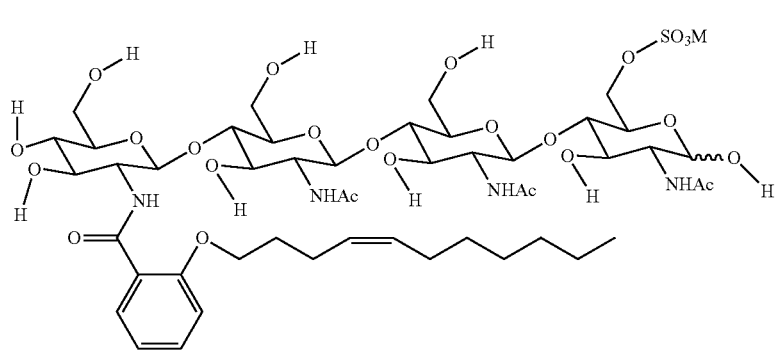
(XX)

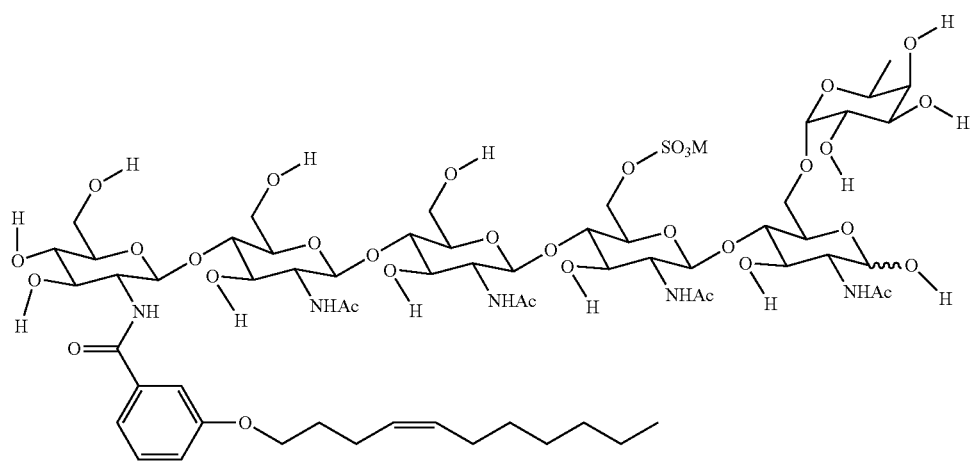
(XXI)
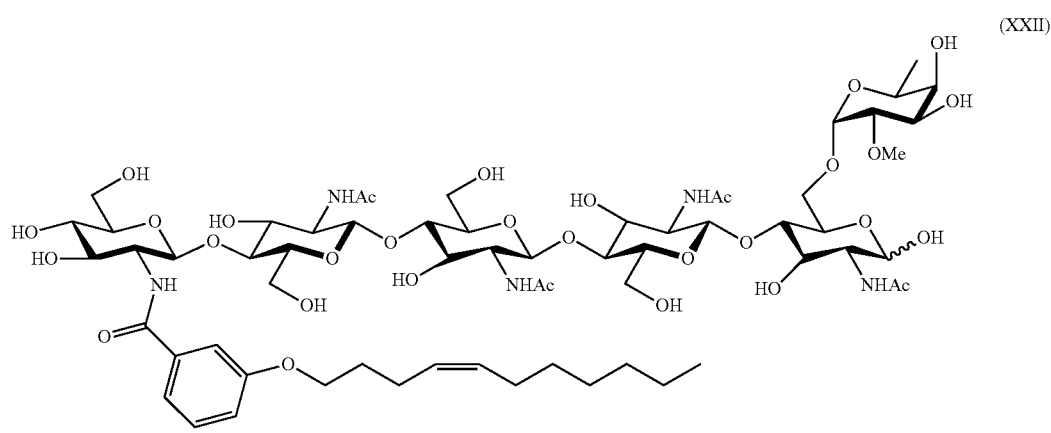
(XXII)
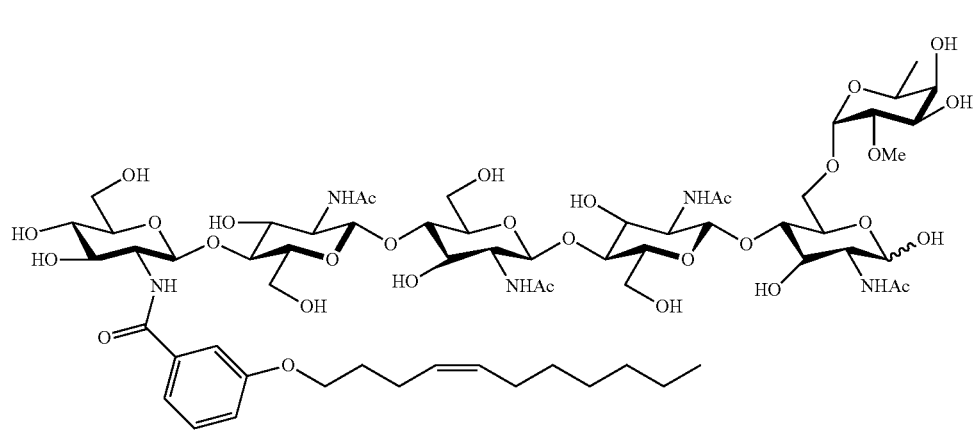
(XXIII)
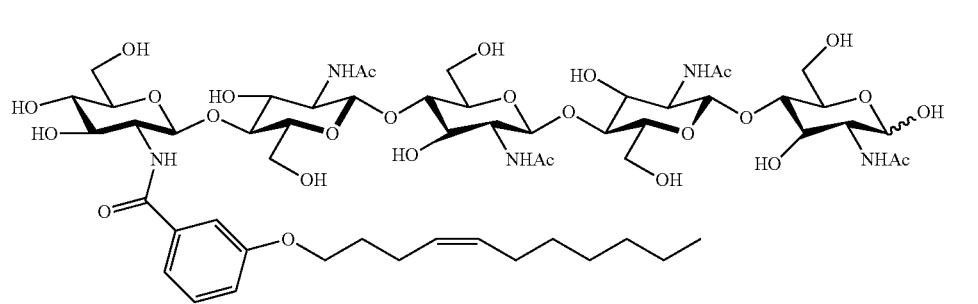
(XXIV)

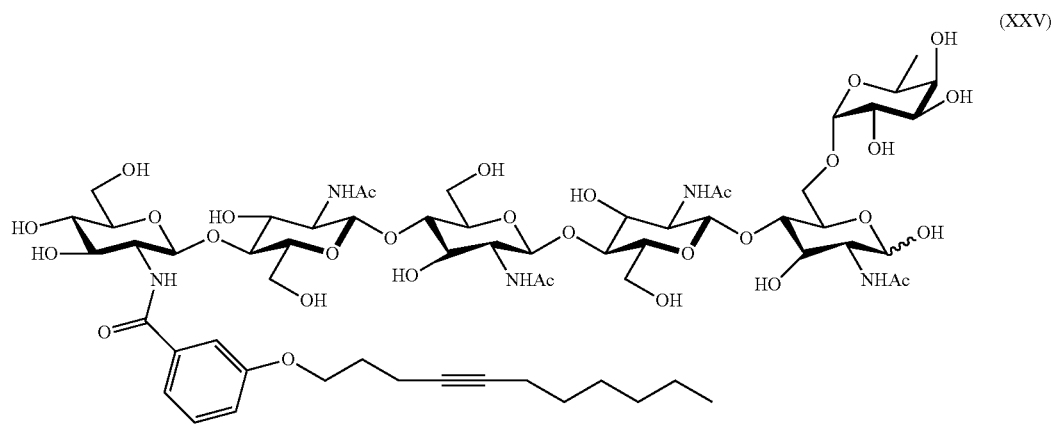
(XXV)
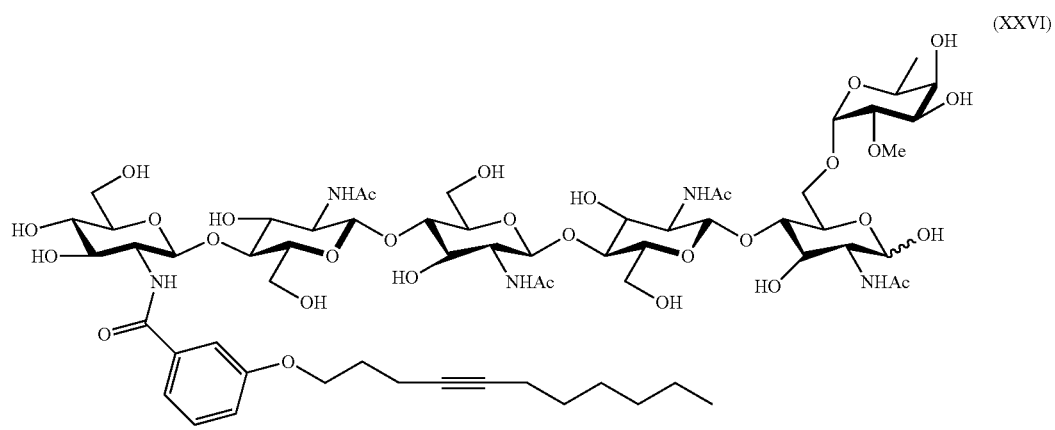
(XXVI)
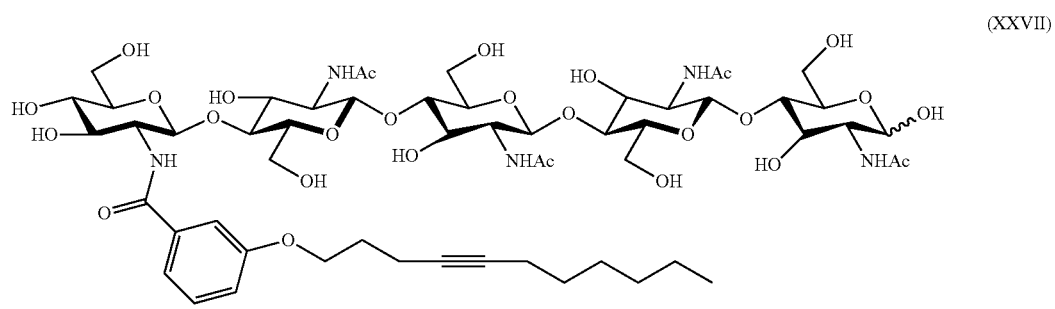
(XXVII)
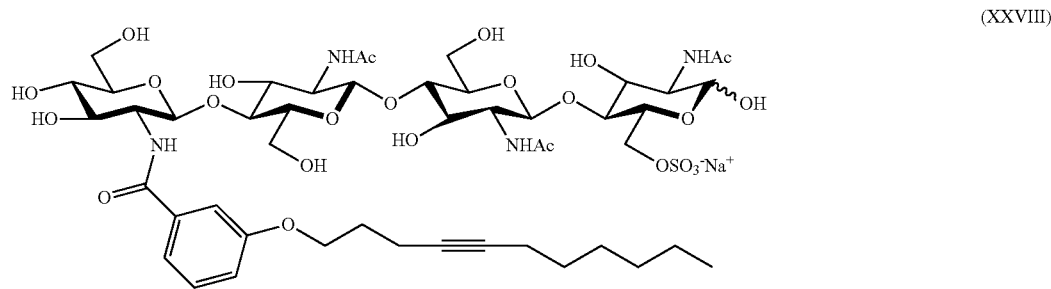
(XXVIII)

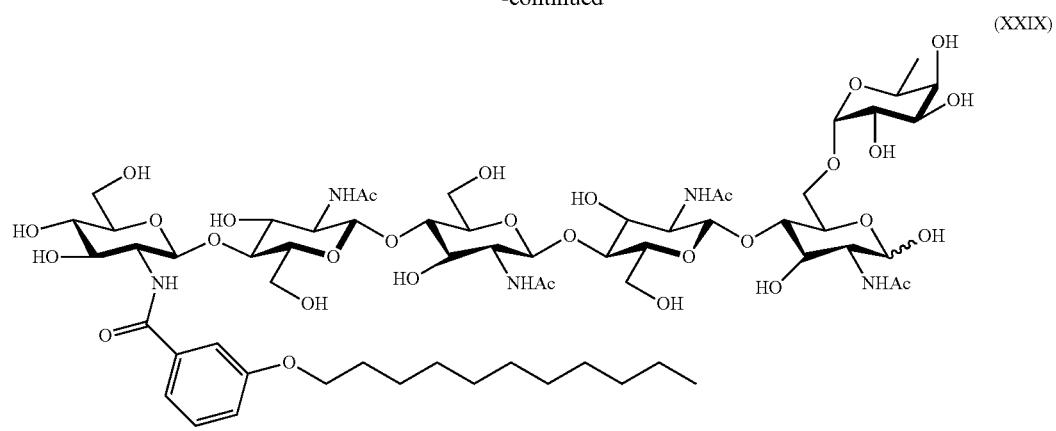
(XXIX)
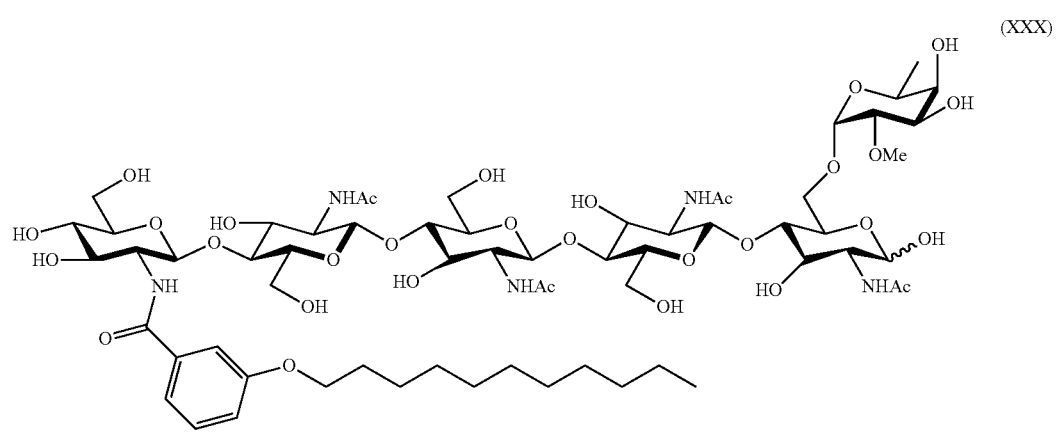
(XXX)
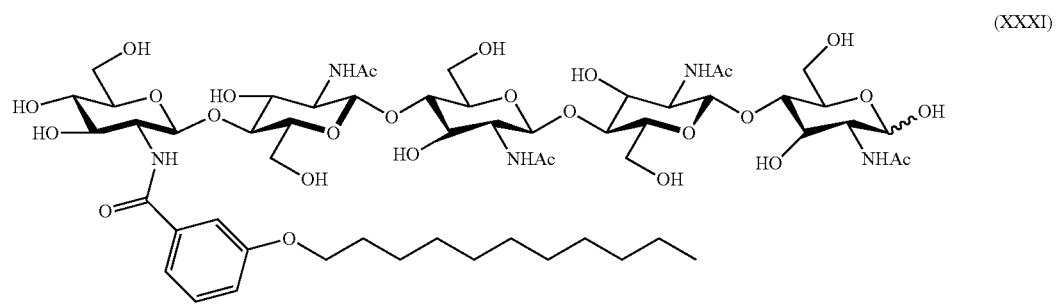
(XXXI)

-continued (XXXII)

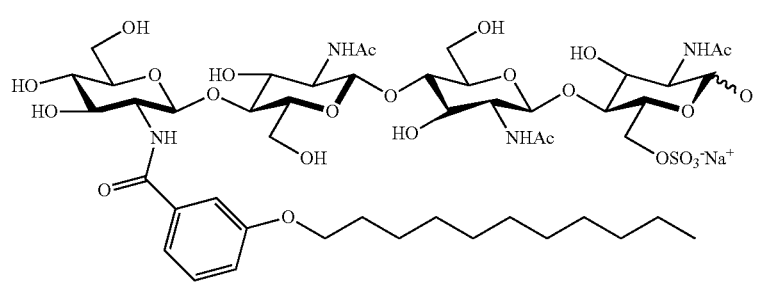

(XXXIII)

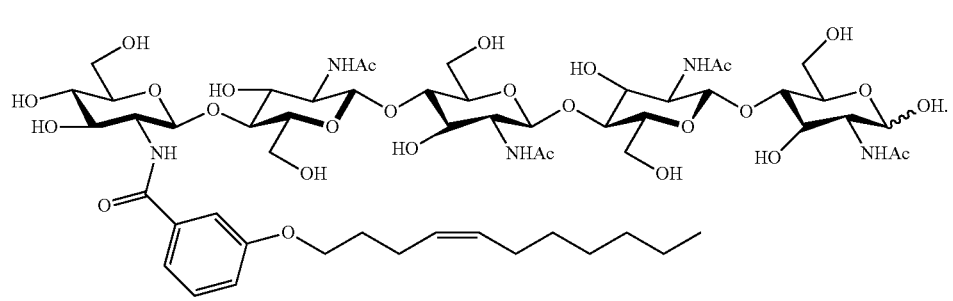

It is to be understood that compositions and methods of the present disclosure may comprise analogues, derivatives, hydrates, isomers, salts and/or solvates of LCOs.

Thus, in some embodiments, inoculant compositions of the present disclosure comprise one, two, three, four, five, six, seven, eight, nine, ten, or more LCOs represented by one or more of formulas I—IV and/or structures V-XXXIII and/or one, two, three, four, five, six, seven, eight, nine, ten, or more analogues, derivatives, hydrates, isomers, salts and/or solvates of LCOs represented by one or more of formulas I—IV and/or structures V-XXXIII.

LCOs may be incorporated into inoculant compositions of the present disclosure in any suitable amount(s)/concentration(s).

In some embodiments, the inoculant compositions of the present disclosure comprise about $1\times10^{-20}$ M to about $1\times10^{-1}$ M LCO. For example, inoculant compositions of the present disclosure may comprise about $1\times10^{-20}$ M, $1\times10^{-19}$ M, $1\times10^{-18}$ M, $1\times10^{-17}$ M, $1\times10^{-16}$ M, $1\times10^{-15}$ M, $1\times10^{-14}$ M, $1\times10^{-13}$ M, $1\times10^{-12}$ M, $1\times10^{-11}$ M, $1\times10^{-10}$ M, $1\times10^{-9}$ M, $1\times10^{-8}$ M, $1\times10^{-7}$ M, $1\times10^{-6}$ M, $1\times10^{-5}$ M, $1\times10^{-4}$ M, $1\times10^{-3}$ M, $1\times10^{-2}$ M, $1\times10^{-1}$ M of one or more LCOs. In some embodiments, the LCO concentration is $1\times10^{-14}$ M to $1\times10^{-5}$ M, $1\times10^{-12}$ M to $1\times10^{-6}$ M, or $1\times10^{-10}$ M to $1\times10^{-7}$ M. In some embodiments, the LCO concentration is $1\times10^{-14}$ M to $1\times10^{-5}$ M, $1\times10^{-12}$ M to $1\times10^{-6}$ M, or $1\times10^{-10}$ M to $1\times10^{-7}$ M.

Inoculant compositions of the present disclosure may comprise any suitable CO(s).

COs, sometimes referred to as N-acetylchitooligosaccharides, are also composed of GlcNAc residues but have side chain decorations that make them different from chitin molecules [$(C_8H_{13}NO_5)_n$, CAS No. 1398-61-4] and chitosan molecules [$(C_5H_{11}NO_4)_n$, CAS No. 9012-76-4]. See, e.g., D'Haeze et al., GLYCOBIOL. 12(6):79R (2002); Demont-Caulet et al., PLANT PHYSIOL. 120(1):83 (1999); Hanel et al., PLANTA 232:787 (2010); Muller et al., PLANT PHYSIOL.124:733 (2000); Robina et al., TETRAHEDRON 58:521-530 (2002); Rouge et al., *Docking of Chitin Oligomers and Nod Factors on Lectin Domains of the LysM-RLK Receptors in the Medicago-Rhizobium Symbiosis*, in THE MOLECULAR IMMUNOLOGY OF COMPLEX CARBOHYDRATES-3 (Springer Science, 2011); Van der Holst et al., CURR. OPIN. STRUC. BIOL. 11:608 (2001); and Wan et al., PLANT CELL 21:1053 (2009); PCT/F100/00803 (2000). COs differ from LCOs in that they lack the pendant fatty acid chain that is characteristic of LCOs.

In some embodiments, inoculant compositions of the present disclosure comprise one or more COs represented by formula XXXIV:

(XXXIV)

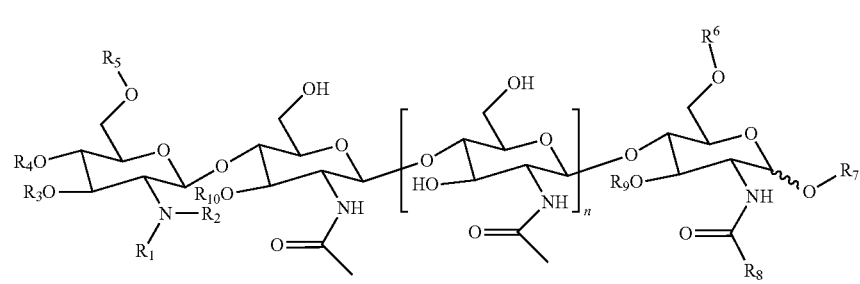

in which $R_1$ represents hydrogen or methyl; $R_2$ represents hydrogen or methyl; $R_3$ represents hydrogen, acetyl or carbamoyl; $R_4$ represents hydrogen, acetyl or carbamoyl; $R_5$ represents hydrogen, acetyl or carbamoyl; $R_6$ represents hydrogen, arabinosyl, fucosyl, acetyl, sulfate ester, 3-0-S-2-0-MeFuc, 2-0-MeFuc and 4-0-AcFuc; $R_7$ represents hydrogen, mannosyl or glycerol; $R_8$ represents hydrogen, methyl, or —$CH_2OH$; $R_9$ represents hydrogen, arabinosyl, or fucosyl; $R_{10}$ represents hydrogen, acetyl or fucosyl; and n represents 0, 1, 2 or 3.

COs included in compositions and methods of the present disclosure may be obtained from any suitable source.

In some embodiments, the CO is derived from an LCO. For example, in some embodiments, inoculant compositions of the present disclosure comprise one or more COs derived from an LCO obtained (i.e., isolated and/or purified) from a strain of *Azorhizobium, Bradyrhizobium* (e.g., *B. japonicum*), *Mesorhizobium, Rhizobium* (e.g., *R. leguminosarum*), *Sinorhizobium* (e.g., *S. meliloti*), or mycorhizzal fungus (e.g., *Glomus infraradicus*). In some embodiments, the CO is derived from an LCO represented by one or more of formulas I-IV and/or structures V-XXXIII. Thus, in some embodiments, inoculant compositions of the present disclosure may comprise one or more COs represented by one or more of formulas I-IV and/or structures V-XXXIII except that the pendant fatty acid is replaced with a hydrogen or methyl group.

In some embodiments, the CO is synthetic. Methods for the preparation of recombinant COs are known in the art. See, e.g., Cottaz et al., METH. ENG. 7(4):311 (2005); Samain et al., CARBOHYDRATE RES. 302:35 (1997.); and Samain et al., J. BIOTECHNOL. 72:33 (1999).

Examples of COs (and derivatives thereof) that may be useful in compositions and methods of the present disclosure are provided below as formula XXXV:

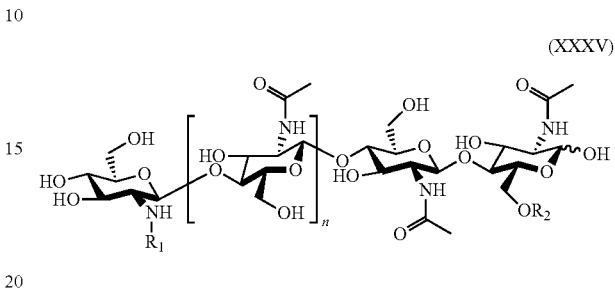

(XXXV)

in which n=1 or 2; $R_1$ represents hydrogen or methyl; and $R_2$ represents hydrogen or $SO_3H$.

Further examples of COs (and derivatives thereof) that may be useful in compositions and methods of the present disclosure are provided below as structures XXXVI-XXXIX:

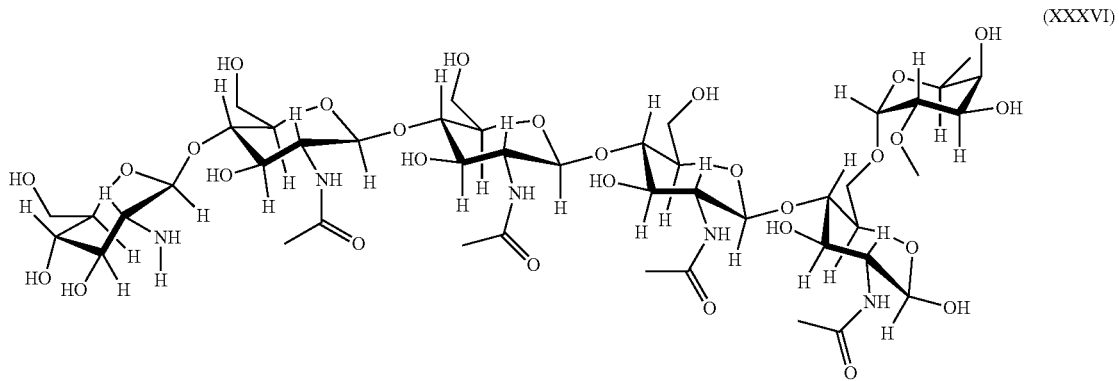

(XXXVI)

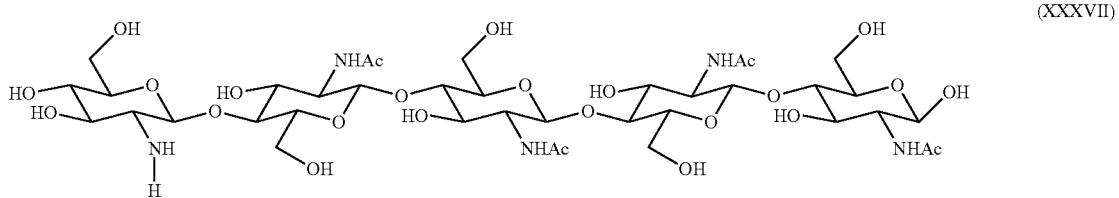

(XXXVII)

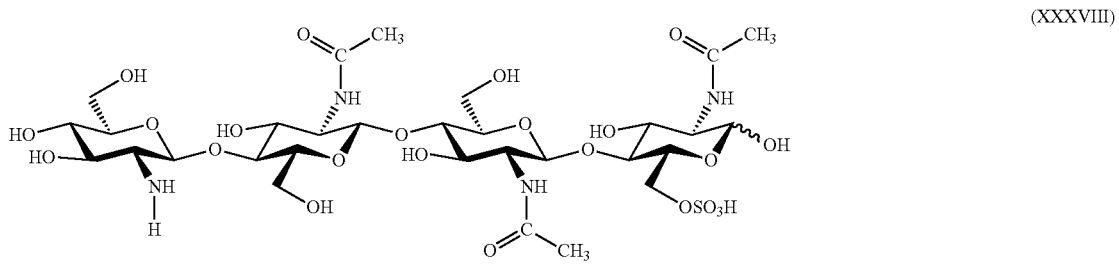

(XXXVIII)

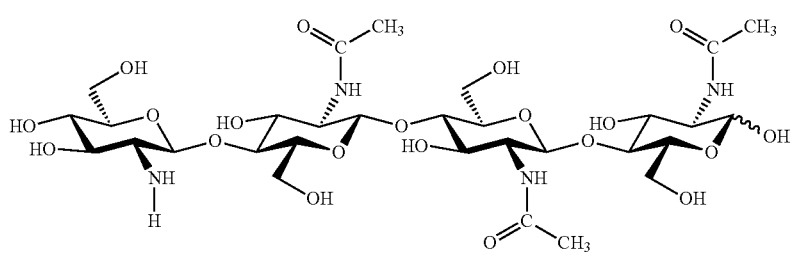
(XXXIX)

COs (and derivatives thereof) may be utilized in various forms of purity and may be used alone or in the form of a culture of CO-producing bacteria or fungi. In some embodiments, the CO(s) included in inoculant compositions of the present disclosure is/are at least 70%, 75%, 80%, 85%, 90%, 91%, 92%, 93%, 94%, 95%, 96%, 97%, 98%, 99%, 99.5% or more pure.

It is to be understood that compositions and methods of the present disclosure may comprise hydrates, isomers, salts and/or solvates of COs.

Thus, in some embodiments, inoculant compositions of the present disclosure comprise one, two, three, four, five, six, seven, eight, nine, ten, or more COs represented by one or more of formulas XXXIV-XXXV and/or structures XXXVI-XXXIX and/or one, two, three, four, five, six, seven, eight, nine, ten, or more analogues, derivatives, hydrates, isomers, salts and/or solvates of COs represented by one or more of formulas XXXIV-XXXV and/or structures XXXVI-XXXIX.

COs may be incorporated into inoculant compositions of the present disclosure in any suitable amount(s)/concentration(s). In some embodiments, the inoculant compositions of the present disclosure comprise about $1\times10^{-20}$ M to about $1\times10^{-1}$ M CO. For example, inoculant compositions of the present disclosure may comprise about 1×M, $1\times10^{-19}$ M, $1\times10^{-18}$ M, $1\times10^{-17}$M, $1\times10^{-16}$ M, $1\times10^{-15}$ M, $1\times10^{-14}$ M, $1\times10^{-13}$ M, $1\times10^{-12}$M, $1\times10^{-11}$M, $1\times10^{-10}$ M, $1\times10^{-9}$M, $1\times10^{-8}$M, $1\times10^{-7}$M, $1\times10^{-6}$M, $1\times10^{-5}$M, $1\times10^{-4}$M, $1\times10^{-3}$ M, $1\times10^{-2}$ M, $1\times10^{-1}$M of one or more COs. In some embodiments, the CO concentration is $1\times10^{-14}$ M to $1\times10^{-5}$ M, $1\times10^{-12}$ M to $1\times10^{-6}$ M, or $1\times10^{-10}$ M to $1\times10^{-7}$ M. In some embodiments, the CO concentration is $1\times10^{-14}$ M to $1\times10^{-5}$ M, $1\times10^{-12}$ M to $1\times10^{-6}$ M, or $1\times10^{-10}$ M to $1\times10^{-7}$ M.

Inoculant compositions of the present disclosure may comprise any suitable chitinous compound(s), including, but not limited to, chitin (IUPAC: N-[5-[[3-acetylamino-4,5-dihydroxy-6-(hydroxymethyl)oxan-2yl]methoxymethyl]-2-[[5-acetylamino-4,6-dihydroxy-2-(hydroxymethyl)oxan-3-yl]methoxymethyl]-4-hydroxy-6-(hydroxymethyl)oxan-3-ys]ethanamide), chitosan (IUPAC: 5-amino-6-[5-amino-6-[5-amino-4,6-dihydroxy-2(hydroxymethyl)oxan-3-yl]oxy-4-hydroxy-2-(hydroxymethyl)oxan-3-yl]oxy-2 (hydroxymethypoxane-3,4-diol) and isomers, salts and solvates thereof.

Chitins and chitosans, which are major components of the cell walls of fungi and the exoskeletons of insects and crustaceans, are composed of GlcNAc residues.

Chitins and chitosans may be obtained commercially or prepared from insects, crustacean shells, or fungal cell walls. Methods for the preparation of chitin and chitosan are known in the art. See, e.g., U.S. Pat. No. 4,536,207 (preparation from crustacean shells) and U.S. Pat. No. 5,965,545 (preparation from crab shells and hydrolysis of commercial chitosan); Pochanavanich, et al., LETT. APPL. MICROBIOL. 35:17 (2002) (preparation from fungal cell walls).

Deacetylated chitins and chitosans may be obtained that range from less than 35% to greater than 90% deacetylation and cover a broad spectrum of molecular weights, e.g., low molecular weight chitosan oligomers of less than 15 kD and chitin oligomers of 0.5 to 2 kD; "practical grade" chitosan with a molecular weight of about 15 kD; and high molecular weight chitosan of up to 70 kD. Chitin and chitosan compositions formulated for seed treatment are commercially available. Commercial products include, for example, ELEXA® (Plant Defense Boosters, Inc.) and BEYOND™ (Agrihouse, Inc.).

Inoculant compositions of the present disclosure may comprise any suitable flavonoid(s), including, but not limited to, anthocyanidins, anthoxanthins, chalcones, coumarins, flavanones, flavanonols, flavans and isoflavonoids, as well as analogues, derivatives, hydrates, isomers, polymers, salts and solvates thereof.

Flavonoids are phenolic compounds having the general structure of two aromatic rings connected by a three-carbon bridge. Classes of flavonoids include are known in the art. See, e.g., Jain et al., J. PLANT BIOCHEM. & BIOTECHNOL. 11:1 (2002); Shaw et al., ENVIRON. MICROBIOL. 11:1867 (2006). Flavonoid compounds are commercially available, e.g., from Novozymes BioAg, Saskatoon, Canada; Natland International Corp., Research Triangle Park, N.C.; MP Biomedicals, Irvine, Calif.; LC Laboratories, Woburn Mass. Flavonoid compounds may be isolated from plants or seeds, e.g., as described in U.S. Pat. Nos. 5,702,752; 5,990,291; and 6,146,668. Flavonoid compounds may also be produced by genetically engineered organisms, such as yeast, as described in Ralston et al., PLANT PHYSIOL. 137:1375 (2005).

In some embodiments, inoculant compositions of the present disclosure comprise one or more anthocyanidins. For example, in some embodiments, inoculant compositions of the present disclosure comprise cyanidin, delphinidin, malvidin, pelargonidin, peonidin and/or petunidin.

In some embodiments, inoculant compositions of the present disclosure comprise one or more anthoxanthins. For example, in some embodiments, inoculant compositions of the present disclosure comprise one or more flavones (e.g., apigenin, baicalein, chrysin, 7,8-dihydroxyflavone, diosmin, flavoxate, 6-hydroxyflavone, luteolin, scutellarein, tangeritin and/or wogonin) and/or flavonols (e.g., amurensin, astragalin, azaleatin, azalein, fisetin, furanoflavonols galangin, gossypetin, 3-hydroxyflavone, hyperoside, icariin, isoquercetin, kaempferide, kaempferitrin, kaempferol, isorhamnetin, morin, myricetin, myricitrin, natsudaidain, pachypodol, pyranoflavonols quercetin, quericitin, rhanmazin, rhamnetin, robinin, rutin, spiraeoside, troxerutin and/or zanthorhamnin).

In some embodiments, inoculant compositions of the present disclosure comprise one or more flavanones. For example, in some embodiments, inoculant compositions of the present disclosure comprise butin, eriodictyol, hesperetin, hesperidin, homoeriodictyol, isosakuranetin, naringenin, naringin, pinocembrin, poncirin, sakuranetin, sakuranin and/or sterubin.

In some embodiments, inoculant compositions of the present disclosure comprise one or more flavanonols. For example, in some embodiments, inoculant compositions of the present disclosure comprise dihydrokaempferol and/or taxifolin.

In some embodiments, inoculant compositions of the present disclosure comprise one or more flavans. For example, in some embodiments, inoculant compositions of the present disclosure comprise one or more flavan-3-ols (e.g., catechin (C), catechin 3-gallate (Cg), epicatechins (EC), epigallocatechin (EGC) epicatechin 3-gallate (ECg), epigallcatechin 3-gallate (EGCg), epiafzelechin, fisetinidol, gallocatechin (GC), gallcatechin 3-gallate (GCg), guibourtinidin, mesquitol, robinetinidol, theaflavin-3-gallate, theaflavin-3'-gallate, theflavin-3,3'-digallate, thearubigin), flavan-4-ols (e.g., apiforol and/or luteoforol) and/or flavan-3,4-diols (e.g., leucocyanidin, leucodelphinidin, leucofisetinidin, leucomalvidin, luecopelargonidin, leucopeonidin, leucorobinetinidin, melacacidin and/or teracacidin) and/or dimers, trimers, oligomers and/or polymers thereof (e.g., one or more proanthocyanidins).

In some embodiments, inoculant compositions of the present disclosure comprise one or more isoflavonoids. For example, in some embodiments, inoculant compositions of the present disclosure comprise one or more isoflavones (e.g, biochanin A, daidzein, formononetin, genistein and/or glycitein), isoflavanes (e.g., equol, ionchocarpane and/or laxifloorane), isoflavandiols, isoflavenes (e.g., glabrene, haginin D and/or 2-methoxyjudaicin), coumestans (e.g., coumestrol, plicadin and/or wedelolactone), pterocarpans and/or roetonoids.

Inoculant compositions of the present disclosure may comprise any suitable flavonoid derivative, including, but not limited to, neoflavonoids (e.g, calophyllolide, coutareagenin, dalbergichromene, dalbergin, nivetin) and pterocarpans (e.g., bitucarpin A, bitucarpin B, erybraedin A, erybraedin B, eiythrabyssin II, erthyrabissin-1, erycristagallin, glycinol, glyceollidins, glyceollins, glycyrrhizol, maackiain, medicarpin, morisianine, orientanol, phaseolin, pisatin, striatine, trifolirhizin).

Flavonoids and derivatives thereof may be incorporated into inoculant compositions of the present disclosure in any suitable form, including, but not limited to, polymorphic and crystalline forms.

Flavonoids may be incorporated into inoculant compositions of the present disclosure in any suitable amount(s)/concentration(s). Inoculant compositions of the present disclosure may comprise any suitable non-flavonoid node-gene inducer(s), including, but not limited to, jasmonic acid ([1R-[1α,2β(Z)]]-3-oxo-2-(pentenyl)cyclopentaneacetic acid; JA), linoleic acid ((Z,Z)-9,12-Octadecadienoic acid) and linolenic acid ((Z,Z,Z)-9,12,15-octadecatrienoic acid), as well as analogues, derivatives, hydrates, isomers, polymers, salts and solvates thereof.

Jasmonic acid and its methyl ester, methyl jasmonate (MeJA), collectively known as jasmonates, are octadecanoid-based compounds that occur naturally in some plants (e.g., wheat), fungi (e.g., *Botryodiplodia theobromae, Gibberella fujikuroi*), yeast (e.g., *Saccharomyces cerevisiae*) and bacteria (e.g., *Escherichia coli*). Linoleic acid and linolenic acid may be produced in the course of the biosynthesis of jasmonic acid. Jasmonates, linoleic acid and linolenic acid (and their derivatives) are reported to be inducers of nod gene expression or LCO production by rhizobacteria. See, e.g., Mabood, et al. PLANT PHYSIOL. BIOCHEM. 44(11):759 (2006); Mabood et al., AGR. J. 98(2):289 (2006); Mabood, et al., FIELD CROPS RES.95(2-3):412 (2006); Mabood & Smith, *Linoleic and linolenic acid induce the expression of nod genes in Bradyrhizobium japonicum USDA* 3, PLANT BIOL. (2001).

Useful derivatives of jasmonic acid, linoleic acid, linolenic acid that may be useful in compositions of the present disclosure include esters, amides, glycosides and salts. Representative esters are compounds in which the carboxyl group of linoleic acid, linolenic acid, or jasmonic acid has been replaced with a —COR group, where R is an —OR$^1$ group, in which R$^1$ is: an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Representative amides are compounds in which the carboxyl group of linoleic acid, linolenic acid, or jasmonic acid has been replaced with a —COR group, where R is an NR$^2$R$^3$ group, in which R$^2$ and R$^3$ are independently: hydrogen; an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Esters may be prepared by known methods, such as acid-catalyzed nucleophilic addition, wherein the carboxylic acid is reacted with an alcohol in the presence of a catalytic amount of a mineral acid. Amides may also be prepared by known methods, such as by reacting the carboxylic acid with the appropriate amine in the presence of a coupling agent such as dicyclohexyl carbodiimide (DCC), under neutral conditions. Suitable salts of linoleic acid, linolenic acid and jasmonic acid include e.g., base addition salts. The bases that may be used as reagents to prepare metabolically acceptable base salts of these compounds include those derived from cations such as alkali metal cations (e.g., potassium and sodium) and alkaline earth metal cations (e.g., calcium and magnesium). These salts may be readily prepared by mixing together a solution of linoleic acid, linolenic acid, or jasmonic acid with a solution of the base. The salts may be precipitated from solution and be collected by filtration or may be recovered by other means such as by evaporation of the solvent.

Non-flavonoid node-gene inducers may be incorporated into inoculant compositions of the present disclosure in any suitable amount(s)/concentration(s).

Inoculant compositions of the present disclosure may comprise karrakin(s), including, but not limited to, 2H-furo[2,3-c]pyran-2-ones, as well as analogues, derivatives, hydrates, isomers, polymers, salts and solvates thereof. In some embodiments, the inoculant composition comprises one or more karrakins represented by formula XXXX:

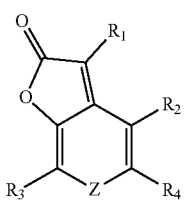

(XXXX)

in which Z is O, S or NR$_5$; R$_1$, R$_2$, R$_3$ and R$_4$ are each independently H, alkyl, alkenyl, alkynyl, phenyl, benzyl, hydroxy, hydroxyalkyl, alkoxy, phenyloxy, benzyloxy, CN, COR$_6$, COOR=, halogen, NR$_6$R$_7$, or NO$_2$; and R$_5$, R$_6$ and R$_7$ are each independently H, alkyl or alkenyl, or a biologically acceptable salt thereof.

Examples of biologically acceptable salts of karrakins may include acid addition salts formed with biologically acceptable acids, examples of which include hydrochloride, hydrobromide, sulphate or bisulphate, phosphate or hydrogen phosphate, acetate, benzoate, succinate, fumarate, maleate, lactate, citrate, tartrate, gluconate; methanesulphonate, benzenesulphonate and p-toluenesulphonic acid. Additional biologically acceptable metal salts may include alkali metal salts, with bases, examples of which include the sodium and potassium salts. Examples of compounds embraced by formula XXXX and which may be suitable for use in the present disclosure include 3-methyl-2H-furo[2,3-c]pyran-2-one (where R$_1$=CH$_3$, R$_2$, R$_3$, R$_4$=H), 2H-furo[2,3-c]pyran-2-one (where R$_1$, R$_2$, R$_3$, R4=H), 7-methyl-2H-furo[2,3-c]pyran-2-one (where R$_1$, R$_2$, R$_4$=H, R$_3$=CH$_3$), 5-methyl-2H-furo[2,3-c]pyran-2-one (where R$_1$, R$_2$, R$_3$=H, R$_4$=CH$_3$), 3,7-dimethyl-2H-furo[2,3-c]pyran-2-one (where R$_1$, R$_3$=CH$_3$, R$_2$, R$_4$=H), 3,5-dimethyl-2H-furo[2,3-c]pyran-2-one (where R$_1$, R$_4$=CH$_3$, R$_2$, R$_3$=H), 3,5,7-trimethyl-2H-furo[2,3-c]pyran-2-one (where R$_1$, R$_3$, R$_4$=CH$_3$, R$_2$=H), 5-methoxymethyl-3-methyl-2H-furo[2,3-c]pyran-2-one (where R$_1$=CH$_3$, R$_2$, R$_3$=H, R$_4$=CH$_2$OCH$_3$), 4-bromo-3,7-dimethyl-2H-furo[2,3-c]pyran-2-one (where R$_1$, R$_3$=CH$_3$, R$_2$=Br, R$_4$=H), 3-methylfuro[2,3-c]pyridin-2(3H)-one (where Z=NH, R$_1$=CH$_3$, R$_2$, R$_3$, R$_4$=H) and 3,6-dimethylfuro[2,3-c]pyridin-2(6H)-one (where Z=N—CH$_3$, R$_1$=CH$_3$, R$_2$, R$_3$, R$_4$=H). See, e.g., U.S. Pat. No. 7,576,213; Halford, *Smoke Signals*, in CHEM. ENG. NEWS (Apr. 12, 2010) (reporting that karrikins or butenolides contained in smoke act as growth stimulants and spur seed germination after a forest fire and can invigorate seeds such as corn, tomatoes, lettuce and onions that had been stored).

Karrakins may be incorporated into inoculant compositions of the present disclosure in any suitable amount(s)/concentration(s).

Inoculant compositions of the present disclosure may comprise gluconolactone and/or one or more analogues, derivatives, hydrates, isomers, polymers, salts and/or solvates thereof.

Gluconolactone may be incorporated into inoculant compositions of the present disclosure in any suitable amount(s)/concentration(s).

In some embodiments, inoculant compositions of the present disclosure are formulated as non-aqueous formulations in which at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the microbial spores therein survive when the inoculant composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure are formulated such that at least about 5, 6, 7, 8, 9, 10, 11, 12, 13, 14, 15, 16, 17, 18, 19, 20, 25, 30, 35, 40, 45, 50, 55, 60, 65, 70% or more of the microorganisms therein survive when the inoculant composition is coated on a seed and stored at 20, 21, 22, 23, 24, 25, 26, 27, 28, 29 and/or 30° C. and 50, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure are formulated as non-aqueous formulations in which at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ cfu/gram or more of the microbial spores therein survive when the inoculant composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure are formulated as non-aqueous formulations in which at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ cfu/ml or more of the microbial spores therein survive when the inoculant composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure are formulated such that at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ cfu/seed or more of the microorganisms therein survive when the inoculant composition is coated on a seed and stored at 20, 21, 22, 23, 24, 25, 26, 27, 28, 29 and/or 30° C. and 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure are formulated as amorphous solids.

In some embodiments, inoculant compositions of the present disclosure are formulated aswettable powders.

In some embodiments, inoculant compositions of the present disclosure are formulated as granuales.

In some embodiments, inoculant compositions of the present disclosure comprise no water.

In some embodiments, inoculant compositions of the present disclosure comprise a trace amount of water.

In some embodiments, inoculant compositions of the present disclosure comprise less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5% water by weight, based upon the total weight of the composition.

In some embodiments, inoculant compositions of the present disclosure have a pH of about 4.5 to about 9.5. In some embodiments, inoculant compositions of the present disclosure have a pH of about 6 to about 7.5. In some embodiments, inoculant compositions of the present disclosure have a pH of about 5, 5.5, 6, 6.5, 7, 7.5, 8 or 8.5.

As noted above, inoculant compositions of the present disclosure may comprise agriculturally beneficial constituents, such as biostimulants, microbial extracts, nutrients, pesticides and plant signal molecules. It is to be understood that agriculturally beneficial constituents may also be used in conjunction with inoculant compositions of the present disclosure. Thus, the present disclosure extends to systems and methods of using inoculant compositions of the present disclosure in conjunction with compositions comprising one or more agriculturally beneficial constituents (e.g., a second composition comprising one or more LCOs and/or COs, a third composition comprising one or more fungicides, herbicides, insectides and/or netamicides, etc.).

Inoculant compositions of the present disclosure may be formulated for the treatment of any suitable plant type, including, but not limited to, row crops and vegetables. In some embodiments, inoculant compositions of the present disclosure are formulated for the treatment of one or more plants selected from Amaranthaceae (e.g., chard, spinach, sugar beet, *quinoa*), Asteraceae (e.g., artichoke, asters, chamomile, chicory, chrysanthemums, dahlias, daisies, *echinacea*, goldenrod, guayule, lettuce, marigolds, safflower, sunflowers, zinnias), Brassicaceae (e.g., arugula, broccoli, bok choy, Brussels sprouts, cabbage, cauliflower, canola, collard greens, daikon, garden cress, horseradish, kale, mustard, radish, rapeseed, rutabaga, turnip, wasabi, watercress, *Arabidopsis thaliana*), Cucurbitaceae (e.g., cantaloupe, cucumber, honeydew, melon, pumpkin, squash (e.g., acorn squash, butternut squash, summer squash), watermelon, zucchini), Fabaceae (e.g., alfalfa, beans, carob, clover, guar, lentils, mesquite, peas, peanuts, soybeans, tamarind, traganth, vetch), Malvaceae (e.g., cacao, cotton, durian, hibiscus, kenaf, kola, okra), Poaceae (e.g., bamboo, barley, corn, fonio, lawn grass (e.g., Bahia grass, Bermudagrass, bluegrass, Buffalograss, Centipede grass, Fescue, or Zoysia), millet, oats, ornamental grasses, rice, lye, sorghum, sugar cane, triticale, wheat), Polygonaceae (e.g., buckwheat), Rosaceae (e.g., almonds, apples, apricots, blackberry, blueberry, cherries, peaches, plums, quinces, raspberries, roses, strawberries), Solanaceae (e.g., bell peppers, chili peppers, eggplant, *petunia*, potato, tobacco, tomato) and Vitaceae (e.g., grape). In some embodiments, inoculant compositions of the present disclosure are formulated for the treatment of one or more fungicide-, herbicide-, insecticide- and/or nematicide-resistant plants (e.g., one or more plants resistant to acetolactate synthase inhibitors.

Non-limiting examples of plants that may be treated with inoculant compositions of the present disclosure include plants sold by Monsanto Company (St. Louis, Mo.) under the BOLLGARD DROUGHTGARD®, GENUITY®, RIB COMPLETE®, ROUNDUP READY®, ROUNDUP READY 2 YIELD®, ROUNDUP READY 2 EXTEND™, SMARTSTAX®, VT DOUBLE PRO®, VT TRIPLE PRO®, YIELDGARD®, YIELDGARD VT ROOTWORM/RR2®, YIELDGARD VT TRIPLE® and/or XTENDFLEX™ tradenames.

The present disclosure extends to plants that have been treated with inoculant compositions of the present disclosure, plant parts harvested from plants that have been treated with inoculant compositions of the present disclosure, processed products derived from plants that have been treated with inoculant compositions of the present disclosure and crops comprising a plurality of plants that have been treated with inoculant compositions of the present disclosure.

The present disclosure also provides coated plant propagation materials comprising, consisting essentially of, or consisting of a plant propagation material and a coating that covers at least a portion of the outer surface of the plant propagation material, said coating comprising, consisting essentially of, or consisting of an inoculant composition of the present disclosure.

The coating may comprise one, two, three, four, five or more layers. In some embodiments, the coating comprises an inner layer that contains one or more microorganisms and one or more outer layers free or substantially free of microorganisms.

In some embodiments, the inner layer of the coating is an inoculant composition of the present disclosure and the outer layer is equivalent to an inoculant composition of the present disclosure but it lacks one or more microorganisms. For example, coated plant propagation materials of the present disclosure may comprise a seed that is coated with an inner layer that comprises microbial spores (e.g., spores of one or more strains of *Bacillus*, one or more strains of *Gliocladium*, one or more strains of *Glomus*, one or more strains of *Metarhizium*, one or more strains of *Penicillium* and/or one or more strains of *Trichoderma*), one or more protectants and one or more dispersants in a non-aqueous carrier and an outer layer that comprises the same carrier but is free of microbial spores.

In some embodiments, the coating comprises, consists essentially of, or consists of an inoculant composition of the present disclosure and a drying powder. For example, coated plant propagation materials of the present disclosure may comprise a seed that is coated with an inoculant composition comprising microbial spores (e.g., spores of one or more strains of *Bacillus*, one or more strains of *Gliocladium*, one or more strains of *Glomus*, one or more strains of *Metarhizium*, one or more strains of *Penicillium* and/or one or more strains of *Trichoderma*), one or more protectants and one or more dispersants in a non-aqueous carrier and is then covered with a drying powder (e.g., a drying power that comprises calcium stearate, one or more clays, graphite, magnesium stearate, magnesium sulfate, powdered milk, silica, soy lecithin and/or talc).

Inoculant compositions of the present disclosure may be coated on plant propagation material in any suitable amount(s)/concentration(s).

In some embodiments, the inoculant composition is applied in an amount ranging from about 0.5 to about 10 milliliters of inoculant composition per kilogram of plant propagation material. For example, in some embodiments, about 0.5, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10 milliliters or more of inoculant composition is applied per kilogram of seed. In some embodiments, an inoculant composition comprising one or more maltodextrins (e.g., one or more maltodextrins having a DEV of about 15 to about 20) and one or more microbial spores (e.g., spores of one or more strains of *Bacillus*, one or more strains of *Gliocladium*, one or more strains of *Glomus*, one or more strains of *Metarhizium*, one or more strains of *Penicillium* and/or one or more strains of *Trichoderma*) is applied at a rate of about 2, 2.25, 2.5, 2.75, 3, 3.25, 3.5, 3.75, or 4 milliliters per kilogram of seed.

Drying powders may be applied in any suitable amount(s)/concentration(s).

In some embodiments, the drying powder is applied in an amount ranging from about 0.5 to about 10 grams of drying powder per kilogram of plant propagation material. For example, in some embodiments, about 0.5, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10 grams or more of drying powder (e.g., drying powder comprising magnesium stearate, magnesium sulfate, powdered milk, silica, soy lecithin and/or talc) is applied per kilogram of seed. In some embodiments, a drying powder comprising calcium stearate, attapulgite clay, montmorillonite clay, graphite, magnesium stearate, silica (e.g., fumed silica, hydrophobically-coated silica and/or precipitated silica) and/or talc is applied to seeds coated with an inoculant composition comprising one or more maltodextrins (e.g., one or more maltodextrins having a DEV of about 15 to about 20) and one or more microbial spores (e.g., spores of one or more strains of *Bacillus*, one or more strains of *Gliocladium*, one or more strains of *Glomus*, one or more strains of *Metarhizium*, one or more strains of *Penicillium* and/or one or more strains of *Trichoderma*) at a rate of about 1, 1.25, 1.5, 1.75, 2, 2.25, 2.5, 2.75, or 3 grams per kilogram of seed.

In some embodiments, the coating covers about 50, 55, 60, 65, 70, 75, 80, 85, 90, 95, 96, 97, 98, 99, 99.5% or more of the outer surface of the plant propagation material.

In some embodiments, the average thickness of the coating is at least 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5 μm or more. In some embodiments, the average thickness of the coating is about 1.5 to about 3.0 μm.

In some embodiments, the coating comprises one or more effect pigments. Effect pigments, which are sometimes also referred to in the art as "pearl pigments," are a class of materials that provide reflectivity, shine, and/or a pearlescent effect when applied as a coating. In some instances, the effect pigment is in the form of a powder comprising a substrate material and a metal oxide coating. For example, the effect pigment may comprise a substrate material including but not limited to talc, silicate materials (e.g., mica), clay minerals, calcium carbonate, kaolin, phlogopite, alumina, and similar substances. In some instances, the substrate material comprises a hydrophilic material. The substrate material may be coated with a semi-transparent layer of a metal oxide, including but not limited to titanium dioxide, iron oxide, chromium oxide, or zirconium oxide. Alternatively, in some instances, the effect pigment comprises metal powder or metal flakes. The metal powder or metal flakes may comprise a metal including, but not limited to aluminum, copper, silver, or bronze. In some instances, the effect pigment comprises a silicate based substrate. Non-limiting examples of particulate silicates that can be incorporated into the dry powder coating include mica coated with titanium dioxide (e.g., SUNMICA FINE WHITE 2800102, which is commercially available from Sun Chemical Corp.). Other non-limiting examples of commercially available effect pigments that can be incorporated into the dry powder include MAGNA PEARL, LUMINA and MEARLIN pigments from BASF Corporation; PHIBRO PEARL from PhibroChem; and IRIDESIUM 120 from Aakash Chemicals. In some instances, the dry powder has a mean particle size of from about 1 to about 25 microns.

Inoculant compositions of the present disclosure may be used to coat any suitable plant propagation materials, including, but not limited to, cuttings (e.g., leaves, stems), rhizomes, seeds and tubers. In some embodiments, the plant propagation material is a seed.

Inoculant compositions of the present disclosure may be used to coat plant propagation materials of any suitable plant type, including, but not limited to, row crops and vegetables. In some embodiments, inoculant compositions of the present disclosure are coated on propagation material derived from one or more plants selected from Amaranthaceae (e.g., chard, spinach, sugar beet, *quinoa*), Asteraceae (e.g., artichoke, asters, chamomile, chicory, chrysanthemums, dahlias, daisies, *echinacea*, goldenrod, guayule, lettuce, marigolds, safflower, sunflowers, zinnias), Brassicaceae (e.g., arugula, broccoli, bok choy, Brussels sprouts, cabbage, cauliflower, canola, collard greens, daikon, garden cress, horseradish, kale, mustard, radish, rapeseed, rutabaga, turnip, wasabi, watercress, Arab idopsis *thaliana*), Cucurbitaceae (e.g., cantaloupe, cucumber, honeydew, melon, pumpkin, squash (e.g., acorn squash, butternut squash, summer squash), watermelon, zucchini), Fabaceae (e.g., alfalfa, beans, carob, clover, guar, lentils, mesquite, peas, peanuts, soybeans, tamarind, tragacanth, vetch), Malvaceae (e.g., cacao, cotton, durian, hibiscus, kenaf, kola, okra), Poaceae (e.g., bamboo, barley, corn, fonio, lawn grass (e.g., Bahia grass, Bermudagrass, bluegrass, Buffalograss, Centipede grass, Fescue, or Zoysia), millet, oats, ornamental grasses, rice, lye, sorghum, sugar cane, triticale, wheat), Polygonaceae (e.g., buckwheat), Rosaceae (e.g., almonds, apples, apricots, blackberry, blueberry, cherries, peaches, plums, quinces, raspberries, roses, strawberries), Solanaceae (e.g., bell peppers, chili peppers, eggplant, *petunia*, potato, tobacco, tomato) and Vitaceae (e.g., grape).

Non-limiting examples of plant propagation materials that may be coated with inoculant compositions of the present disclosure include seeds sold by Monsanto Company (St. Louis, Mo.) under the BOLLGARD DROUGHTGARD®, GENUITY®, RIB COMPLETE®, ROUNDUP READY®, ROUNDUP READY 2 YIELD®, ROUNDUP READY 2 EXTEND™, SMARTSTAX®, VT DOUBLE PRO®, VT TRIPLE PRO®, YIELDGARD®, YIELDGARD VT ROOTWORM/RR2®, YIELDGARD VT TRIPLE® and/or XTENDFLEX™ tradenames.

The present disclosure extends to plants that grow from coated plant propagation materials of the present disclosure, plant parts harvested from plants that grow from coated plant propagation materials of the present disclosure, processed products derived from plants that grow from coated plant propagation materials of the present disclosure and crops comprising a plurality of plants that grow from coated plant propagation materials of the present disclosure.

The present disclosure also provides kits comprising, consisting essentially of, or consisting of a coated plant propagation material of the present disclosure and a container housing the coated plant propagation material. In some embodiments, the kit further comprises one or more oxygen scavengers, such as activated carbon, ascorbic acid, iron powder, mixtures of ferrous carbonate and metal halide catalysts, sodium chloride and/or sodium hydrogen carbonate.

The container may comprise any suitable material(s), including, but not limited to, materials that reduce the amount of light, moisture and/or oxygen that contact the coated plant propagation material when the container is sealed.

In some embodiments, the container comprises, consists essentially of, or consists of a material having light permeability of less than about 1, 2, 3, 4, 5, 6, 7, 8, 9, 10, 15, 20, 25, 30, 35, 40, 45, 50, 55, 60, 65, 70 or 75%.

In some embodiments, the container reduces the amount of ambient light that reaches said coated plant propagation material by about 5, 10, 15, 20, 25, 30, 35, 40, 45, 50, 55, 60, 65, 70, 75, 80, 85, 90, 95 or 100% when sealed.

In some embodiments, the container reduces the amount of ambient moisture that reaches said plant propagation material by about 5, 10, 15, 20, 25, 30, 35, 40, 45, 50, 55, 60, 65, 70, 75, 80, 85, 90, 95 or 100% when sealed.

In some embodiments, the container comprises, consists essentially of, or consists of a material having an oxygen transmission rate of less than about 5, 10, 15, 20, 25, 30, 35, 40, 45, 50, 60, 70, 80, 90, 100, 125, 150, 175, 200, 225, 250, 275, 300, 325, 350, 375, 400, 425, 450, 475, or 500 $cm^3/m^2 \cdot day$ (as measured in accordance with ASTM D3985).

In some embodiments, the container reduces the amount of ambient oxygen that reaches said plant propagation material by about 5, 10, 15, 20, 25, 30, 35, 40, 45, 50, 55, 60, 65, 70, 75, 80, 85, 90, 95 or 100% when sealed.

In some embodiments, kits of the present disclosure comprise 1, 2, 3, 4, 5 or more additional containers. The additional containers may comprise any suitable component(s) or composition(s), including, but not limited to, agriculturally beneficial microorganisms, biostimulants, drying agents, nutrients, oxidation control components and pesticides. Examples of agriculturally beneficial microorganisms, biostimulants, drying agents, nutrients, oxidation control components and pesticides that may be included in the additional containers are described above.

The present disclosure also provides animal feed compositions comprising, consisting essentially of, or consisting of a food component and a microbial component, said microbial component comprising, consisting essentially of, or consisting of an inoculant composition of the present disclosure.

Animal feed compositions of the present disclosure may comprise any suitable food component, including, but not limited to, fodder (e.g., grains, hay, legumes, silage and/or straw) and forage (e.g., grass).

Animal feed compositions of the present disclosure may be fed to any suitable animal, including, but not limited to, farm animals, zoo animals, laboratory animals and/or companion animals. In some embodiments, the animal feed composition is formulated to meet the dietary needs of birds (e.g., chickens, ducks, quails and/or turkeys), bovids (e.g., antelopes, bison, cattle, gazelles, goats, impala, oxen, sheep and/or wildebeests), canines, cervids (e.g., caribou, deer, elk and/or moose), equines (e.g., donkeys, horses and/or zebras), felines, fish, pigs, rabbits, rodents (e.g., guinea pigs, hamsters, mice and/or rats) and the like.

The present disclosure also provides methods comprising, consisting essentially of, or consisting of applying an inoculant composition of the present disclosure to a plant or plant part.

Inoculant compositions of the present disclosure may be applied in any suitable manner, including, but not limited to, on-seed application, in-furrow application, soil application and foliar application.

In some embodiments, inoculant compositions of the present disclosure are applied to plant propagation materials (e.g., seeds) at least 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more prior to planting.

In some embodiments, inoculant compositions of the present disclosure are applied to plant propagation materials (e.g., seeds) at the time of planting.

Plant propagation materials may be treated using any suitable method(s), including, but not limited to, coating, dripping, spraying and soaking Batch systems, in which predetermined batch sizes of material and inoculant composition are delivered into a mixer, may be employed. Continuous treatment systems, which are calibrated to apply inoculant composition at a predefined rate in proportion to a continuous flow of material, may also be employed.

In some embodiments, plant propagation materials are soaked for at least 0.1, 0.2, 0.3, 0.4, 0.5, 0.6, 0.7, 0.8, 0.9, 1, 1.25, 1.5, 1.75, 2, 3, 4, 5, 6, 9, 12, 15, 18, 21, 24, 36, 48 hours or more in an inoculant composition of the present disclosure.

In some embodiments, plant propagation materials (e.g., seeds) are coated by applying an inoculant composition of the present disclosure to the inside wall of a round container, adding the seeds, then rotating the container such that the seeds come into contact with the composition, a process known in the art as "container coating".

In some embodiments, an inoculant composition of the present disclosure is freeze-spray- or spray-freeze-dried and then applied to plant propagation material. For examples, in some embodiments, an inoculant composition comprising one or more maltodextrins (e.g., one or more maltodextrins having a DEV of about 15 to about 20), one or more microbial spores (e.g., spores of one or more strains of *Bacillus*, one or more strains of *Gliocladium*, one or more strains of *Glomus*, one or more strains of *Metarhizium*, one or more strains of *Penicillium* and/or one or more strains of *Trichoderma*) and one or more disaccharides (e.g., maltose) is freeze-spray- or spray-freeze-dried, mixed with a drying powder (e.g., a drying powder comprising calcium stearate, attapulgite clay, montmorillonite clay, graphite, magnesium stearate, silica (e.g., fumed silica, hydrophobically-coated silica and/or precipitated silica) and/or talc), then coated on seed that was been pre-treated with one or more adhesives (e.g., an adhesive composition comprising one or more maltodextrins, one or more mono-, di- or oligosaccharides, one or more peptones, etc.), one or more pesticides and/or one or more plant signal molecules (e.g., one or more LCOs).

The present disclosure also provides methods comprising, consisting essentially of, or consisting of planting a coated seed of the present disclosure.

The present disclosure also provides methods of enhancing the survival and/or stability of microbial spores in a composition, said methods comprising, consisting essentially of, or consisting of adding an effective amount of one or more protectants to said composition.

Protectants may be used to improve any suitable microbial stability characteristic(s) of the microbial spores in a composition, including, but not limited to, the ability of the microbial spores in a composition to enhance plant yield after being coated on a seed and stored for a defined period of time prior to planting the seed. For example, the addition of one or more protectants to a composition enhances the ability of the microbial spores therein to propagate and increase yield after being coated on a plant propagation material (e.g., seed) and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the addition of one or more protectants to a composition improves the stability of one or more microbial spores therein by at least about 0.1, 0.5, 1, 2, 3, 4, 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to microbial spores in a control composition (e.g., a control composition that is identical to the inoculant composition of the present disclosure except that it lacks one or more of the components found in the inoculant composition and/or contains one or more components not found in the inoculant composition of the present disclosure). For example, the addition of one or more protectants to a composition may improve one or more microbial stability characteristics of one or more microbial spores therein by at least about 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition that is identical to the inoculant composition except that lacks one or more of the protectants found in the inoculant composition and/or comprises a reduced amount of one or more of the protectants found in the inoculant composition.

In some embodiments, the addition of one or more protectants to a composition improves the stability of one or more microbial spores therein by at least about 0.1, 0.5, 1, 2, 3, 4, 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition (e.g., a control composition that is identical to the inoculant composition of the present disclosure except that it lacks one or more of the components found in the inoculant composition and/or contains one or more components not found in the inoculant composition of the present disclosure). For example, the addition of one or more protectants to a composition may improve the survival rate of one or more of the microbial spores contained therein by at least about 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition that is identical to the inoculant composition except that lacks one or more of the protectants found in the inoculant composition and/or comprises a reduced amount of one or more of the protectants found in the inoculant composition.

In some embodiments, the addition of one or more protectants to a composition improves the survival of one or more of the microbial spores in an inoculant composition to the extent that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the microbial spores survive when the inoculant composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more. In some embodiments, the addition of one or more protectants to a composition improves the survival of one or more of the microbial spores in an inoculant composition to the extent that at least about 5, 6, 7, 8, 9, 10, 11, 12, 13, 14, 15, 16, 17, 18, 19, 20, 25, 30, 35, 40, 45, 50, 55, 60, 65, 70% or more of the microbial spores survive when the inoculant composition is coated on a seed, dried and stored at 20, 21, 22, 23, 24, 25, 26, 27, 28, 29 and/or 30° C. and 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the addition of one or more protectants to a composition improves the survival of one or more of the microbial spores in an inoculant composition to the extent that at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ cfu/seed or more of the microbial spores survive when the inoculant composition is coated on a seed and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more. In some embodiments, the addition of one or more protectants to a composition improves the survival of one or more of the microbial spores in an inoculant composition to the extent that at least $1\times10^1$, $1\times10^2$, $1\times10^3$, $1\times10^4$, $1\times10^5$, $1\times10^6$, $1\times10^7$ cfu/seed or more of the microbial spores survive when the inoculant composition is coated on a seed and stored at 20, 21, 22, 23, 24, 25, 26, 27, 28, 29 and/or 30° C. and 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the addition of one or more maltodextrins to a composition improves both the survival rate and one, two, three, four, five, six, seven, eight, nine, ten or more microbial stability characteristics of the microbial spore(s) contained therein.

Any suitable protectant(s) may be added to the composition, including, but not limited to maltodextrins and oxidation control components.

In some embodiments, one or more maltodextrins is added to the inoculant composition.

Any suitable maltodextrin(s) may be added to the composition, including, but not limited to, maltodextrins having a dextrose equivalent value (DEV) of about 3, 4, 5, 6, 7, 8, 9, 10, 11, 12, 13, 14, 15, 16, 17, 18, 19, 20, 21, 22, 23, 24, or 25. In some embodiments, one or more maltodextrins having a DEV of about 5 to about 6, 7, 8, 9, 10, 11, 12, 14, 15, 16, 17, 18, 19, 20, 21, 22, 23, 24, or 25, about 10 to about 11, 12, 14, 15, 16, 17, 18, 19, 20, 21, 22, 23, 24, or 25, or about 15 to about 16, 17, 18, 19, 20, 21, 22, 23, 24, or 25 is added to the composition. In some embodiments, a combination of maltodextrins having a DEV of about 5 to about 6, 7, 8, 9, 10, 11, 12, 14, 15, 16, 17, 18, 19, 20, 21, 22, 23, 24, or 25, about 10 to about 11, 12, 14, 15, 16, 17, 18, 19, 20, 21, 22, 23, 24, or 25, or about 15 to about 16, 17, 18, 19, 20, 21, 22, 23, 24, or 25 is added to the composition. In some embodiments, one or more maltodextrins having a DEV of about 10 to about 25 (e.g., one or more maltodextrins having a DEV of about 15 to about 20) is added to the composition. In some embodiments, a combination of maltodextrins having a DEV of about 10 to about 25 (e.g., a combination of maltodextrins having a DEV of about 15 to about 20) is added to the composition.

Non-limiting examples of maltodextrins that may be useful in methods of the present disclosure include MALTRIN® M150 (DEV=15; molecular weight=1200; Grain Processing Corporation, Muscatine, Iowa), MALTRIN® M200 (DEV=20; molecular weight=900; Grain Processing Corporation, Muscatine, Iowa), MALTRIN® M250 (DEV=25; molecular weight=720; Grain Processing Corporation, Muscatine, Iowa); MALTRIN QD® M580 (DEV=16.5-19.9; Grain Processing Corporation, Muscatine, Iowa); MALTRIN QD® M585 (DEV=15.0-19.9; Grain Processing Corporation, Muscatine, Iowa); MALTRIN QD® M600 (DEV=20.0-23.0; Grain Processing Corporation, Muscatine, Iowa); GLOBE® Plus 15 DE (Ingredion Inc., Westchester, Ill.) and combinations thereof. In some embodiments, the maltodextrin (or combination of maltodextrins) has a DEV of 15 to 20.

Maltodextrins may be added to the composition in any suitable form. In some embodiments, the maltodextrin(s) added to the composition is/are at least 70, 75, 80, 85, 90, 91, 92, 93, 94, 95, 96, 97, 98, 99, 99.5% or more pure.

The absolute value of the amount/concentration/dosage of maltodextrins that is sufficient to cause the desired effect may be affected by factors such as the type, size and volume of material to which the composition will be applied, the stability of the microbial spores in the composition, the identity and amounts/concentrations of other components in the inoculant composition (e.g., monosaccharides, disaccharides, sugar alcohols) and the storage conditions (e.g., temperature, relative humidity, duration). Those skilled in the art will understand how to select an effective amount/concentration/dosage using routine dose-response experiments.

In some embodiments, the maltodextrin(s) is/are added to the composition until they comprise about 5 to about 95% or more (by weight) of the composition. For example, one or more maltodextrins may be added until the composition comprises about 5, 10, 15, 20, 25, 30, 35, 40, 45, 50, 55, 60, 65, 70, 75, 80, 85, 90, 95% or more of one or more maltodextrins (each and/or collectively) having a DEV value of about 15 to about 20. In some embodiments, the maltodextrin amount/concentration is about 1 to about 65%, about 10% to about 30%, about 20% to about 40%, about 20% to about 50%, or about 30 to about 60% (by weight) of the composition.

In some embodiments, the maltodextrin(s) is/are added to the composition in an amount/concentration sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the microbial spores therein survive when the inoculant composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more. In some embodiments, the maltodextrin(s) is/are added to the composition in an amount/concentration sufficient to ensure that at least about 20, 25, 30, 35, 40, 45, 50, 55, 60, 65, 70% or more of the microbial spores therein survive when the inoculant composition is coated on a seed, dried and stored at 20, 21, 22, 23, 24, 25, 26, 27, 28, 29 and/or 30° C. and 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the maltodextrin(s) is/are added to the composition in an amount/concentration sufficient to ensure that at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ cfu/seed or more of the microbial spores therein survive when the inoculant composition is coated on a seed and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more. In some embodiments, the maltodextrin(s) is/are added to the composition in an amount/concentration sufficient to ensure that at least $1\times10^1$, $1\times10^2$, $1\times10^3$, $1\times10^4$, $1\times10^5$, $1\times10^6$, $1\times10^7$ cfu/seed or more of the microbial spores therein survive when the inoculant composition is coated on a seed and stored at 20, 21, 22, 23, 24, 25, 26, 27, 28, 29 and/or 30° C. and 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, one or more oxidation control components is added to the inoculant composition.

Any suitable oxidation control component(s) may be added to the composition, including, but not limited to, antioxidants and/or oxygen scavengers. In some embodiments, ascorbic acid, ascorbyl palmitate, ascorbyl stearate, calcium ascorbate, carotenoids, glutathione, lipoic acid, phenolic compounds (e.g., flavonoids, flavones, flavonols), potassium ascorbate, sodium ascorbate, sodium hydrogen carbonate, thiols (e.g., glutathione, lipoic acid, N-acetyl cysteine), tocopherols, tocotrienols, ubiquinone and/or uric acid is added to the composition. In some embodiments, ascorbic acid is added to the composition.

The absolute value of the amount/concentration/dosage of oxidation control components that is sufficient to cause the desired effect may be affected by factors such as the type, size and volume of material to which the composition will be applied, the stability of the microbial spores in the composition and the storage conditions (e.g., temperature, relative humidity, duration). Those skilled in the art will understand how to select an effective amount/concentration/dosage using routine dose-response experiments.

In some embodiments, the oxidation control component(s) is/are added to the composition in an amount/concentration ranging from about 0.0001 to about 5% or more (by weight) of the composition. For example, one or more oxidation control components may be added until it/they comprise(s) about 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5% or more of the composition.

In some embodiments, the oxidation control component(s) is/are added to the composition at a concentration ranging from about $1\times10^{-20}$ M to about $1\times10^{-1}$ M. For example, one or more oxidation control components may be added until the composition comprises about $1\times10^{-20}$ M, $1\times10^{-19}$ M, $1\times10^{-18}$M, $1\times10^{-17}$M, $1\times10^{-16}$M, $1\times10^{-15}$ $1\times10^{-14}$ M, $1\times10^{-13}$ M, $1\times10^{-12}$ M, $1\times10^{-11}$ M, $1\times10^{-10}$ M, $1\times10^{-9}$ M, $1\times10^{-8}$ M, $1\times10^{-7}$ M, $1\times10^{-6}$ M, $1\times10^{-5}$M, $1\times10^{-4}$M, $1\times10^{-3}$M, $1\times10^{-2}$ M, $1\times10^{-1}$M of one or more oxidation control components.

In some embodiments, the oxidation control component (s) is/are added to the composition in an amount/concentration sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the microbial spores therein survive when the inoculant composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more. In some embodiments, the oxidation control component (s) is/are added to the composition in an amount/concentration sufficient to ensure that at least about 5, 6, 7, 8, 9, 10, 11, 12, 13, 14, 15, 16, 17, 18, 19, 20, 25, 30, 35, 40, 45, 50, 55, 60, 65, 70% or more of the microbial spores therein survive when the inoculant composition is coated on a seed, dried and stored at 20, 21, 22, 23, 24, 25, 26, 27, 28, 29 and/or 30° C. and 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the oxidation control component (s) is/are added to the composition in an amount/concentration sufficient to ensure that at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ cfu/seed or more of the microbial spores therein survive when the inoculant composition is coated on a seed and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more. In some embodiments, the oxidation control component (s) is/are added to the composition in an amount/concentration sufficient to ensure that at least $1\times10^1$, $1\times10^2$, $1\times10^3$, $1\times10^4$, $1\times10^5$, $1\times10^6$, $1\times10^7$ cfu/seed or more of the microbial spores therein survive when the inoculant composition is coated on a seed and stored at 20, 21, 22, 23, 24, 25, 26, 27, 28, 29 and/or 30° C. and 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, one or more hygroscopic polymers is added to the inoculant composition. For example, in some embodiments, albumin, alginate, cellulose, gums (e.g., cellulose gum, guar gum, gum arabic, gum combretum, xantham gum), methyl cellulose, nylons, pectin, polyacrylic acid, polycarbonates, polyethylene glycol (PEG), polyethylenimine (PEI), polylactides, polymethylacrylate (PMA), polyurethanes, polyvinyl alcohol (PVA), polyvinylpyrrolidone (PVP), propylene glycol, sodium carboxymethyl cellulose and/or starch is added to the inoculant composition.

Non-limiting examples of hygroscopic polymers that may be useful in methods of the present disclosure include AGRIMER™ polymers (e.g., 30, AL-10 LC, AL-22, AT/ATF, VA 3E, VA 3 1, VA 5E, VA 5l, VA 6, VA 6E, VA 7E, VA 7l, VEMA AN-216, VEMA AN-990, VEMA AN-1200, VEMA AN-1980, VEMA H-815MS; Ashland Specialty Ingredients, Wilmington, Del.), EASYSPERSE™ polymers (Ashland Specialty Ingredients, Wilmington, Del.); DISCO™ AG polymers (e.g., L-250, L-280, L-285, L-286, L-320, L-323, L-517, L-519, L-520, L800; Incotec Inc., Salinas, Calif.), KELZAN® polymers (Bri-Chem Supply Ltd., Calgary, Alberta, Calif.), SEEDWORX™ polymers (e.g., Bio 200; Aginnovation, LLC, Walnut Groove, Calif.), TABULOSE® gels (e.g., SC-580, SC-612, SC-613, SC-681; Blanver Farmoquimica, Boca Raton, Fla.), TICAXAN® xanthan powders (TIC Gums, White Marsh, Md.) and combinations thereof.

Additional examples of hygroscopic polymers that may be added to inoculant compositions of the present disclosure may be found in Pouci, et al. AM. J. AGRIC. BIOL. SCI. 3(1):299 (2008).

The absolute value of the amount/concentration/dosage of maltodextrins that is sufficient to cause the desired effect may be affected by factors such as the type, size and volume of material to which the compositon will be applied, the stability of the microbial spores in the composition, the identity and amounts/concentrations of other components in the inoculant composition (e.g., monosaccharides, disaccharides, sugar alcohols) and the storage conditions (e.g., temperature, relative humidity, duration). Those skilled in the art will understand how to select an effective amount/concentration/dosage using routine dose-response experiments.

Hygroscopic polymers may be add to the inoculant composition in any suitable amount(s)/concentration(s). In some embodiments, the hygroscopic polymer(s) is/are added of the composition until it/they comprise(s) about 0.1 to about 25% (by weight) of the inoculant composition. For example, inoculant compositions of the present disclosure may comprise about 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25% or more (by weight) of one or more hygroscopic polymers. In some embodiments, the hygroscopic polymer amount/concentration is about 0.1, 0.2, 0.3, 0.4, 0.5, 0.6, 0.7, 0.8, 0.9 or 1 to about 1, 1.5, 2, 2.5, 3, 3.5, 4, 4.5, 5, 5.5, 6, 6.5, 7, 7.5, 8, 8.5, 9, 9.5 or 10% (by weight) of the inoculant composition.

In some embodiments, the hygroscopic polymer(s) is/are added to the composition in an amount/concentration sufficient to ensure that at least about 0.01, 0.05, 0.1, 0.5, 1, 2, 3, 4, 5, 10, 15, 20, 25, 30, 35, 40, 45, 50, 55, 60, 65% or more of the microbial spores in the inoculant composition survive following desiccation (of about 0, 5, 10, 15, 20, 25, 30, 35, 40, 45, 50, 55, 60, 65, 70, 75, 80, 85, 90, 95% or more) and storage at 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the hygroscopic polymer(s) is/are added to the composition in an amount/concentration sufficient to ensure that at least about 0.01, 0.05, 0.1, 0.5, 1, 2, 3, 4, 5, 10, 15, 20, 25, 30, 35, 40, 45, 50, 55, 60, 65% or more of the microbial spores in the inoculant composition survive following storage at 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the hygroscopic polymer (s) is/are added to the composition in an amount/concentration sufficient to ensure that at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ cfu/seed or more of the microbial spores therein survive when the inoculant composition is coated on a seed and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more. In some embodiments, the hygroscopic polymer (s) is/are added to the composition in an amount/concentration sufficient to ensure that at least $1\times10^1$, $1\times10^2$, $1\times10^3$, $1\times10^4$, $1\times10^5$, $1\times10^6$, $1\times10^7$ cfu/seed or more of the microbial spores therein survive when the inoculant composition is coated on a seed and stored at 20, 21, 22, 23, 24, 25, 26, 27, 28, 29 and/or 30° C. and 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

The present disclosure also provides systems and methods of using inoculant compositions of the present disclosure in conjunction with additional compositions comprising one or more agriculturally beneficial constituents. The additional composition(s) may comprise any suitable agriculturally beneficial constituent(s), including, but not limited to, the agriculturally beneficial constituents described above.

In some embodiments, inoculant compositions of the present disclosure are used in conjunction with one or more on-seed compositions, one or more in-furrow compositions, one or more soil-applied compositions and/or one or more foliar-applied compositions.

In some embodiments, inoculant compositions of the present disclosure are used as part of an integrated disease and/or pest management system.

Particular embodiments of the present disclosure are described in the following numbered paragraphs:

1. An inoculant composition, comprising, consisting essentially of, or consisting of:
   microbial spores; and
   a non-aqueous carrier.

2. The inoculant composition of any one of the preceding paragraphs, wherein said microbial spores comprise about 0.1% to about 30% (by weight) of said inoculant composition, optionally about 5 to about 15% (by weight) of said composition, optionally about 1, 2, 3, 4, 5, 6, 7, 8, 9, 10, 11, 12, 13, 14, 15, 16, 17, 18, 19, 20, 21, 22, 23, 24 or 25% (by weight) of said inoculant composition.

3. The inoculant composition of any one of the preceding paragraphs, wherein said microbial spores are present in said inoculant composition in a concentration ranging from about $1\times10^1$ to about $1\times10^{20}$ colony-forming units per gram and/or milliliter of said inoculant composition, optionally $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ or more colony-forming units per gram and/or milliliter of said inoculant composition.

4. The inoculant composition of any one of the preceding paragraphs, wherein said microbial spores comprise, consist essentially of, or consist of spores of one or more diazotrophic microorganisms.

5. The inoculant composition of any one of the preceding paragraphs, wherein said microbial spores comprise, consist essentially of, or consist of spores of one or more strains of *Bacillus*, optionally one or more strains of *Bacillus circulans, Bacillus licheniformis, Bacillus macerans, Bacillus megatarium, Bacillus polymyxa* and/or *Bacillus pumilus*.

6. The inoculant composition of any one of the preceding paragraphs, wherein said microbial spores comprise, consist essentially of, or consist of spores of one or more phosphate-solubilizing microorganisms.

7. The inoculant composition of any one of the preceding paragraphs, wherein said microbial spores comprise, consist essentially of, or consist of spores of one or more strains of *Penicillium*, optionally one or more strains of *P. bilaiae* and/or *P. gaesfrivorus*.

8. The inoculant composition of any one of the preceding paragraphs, wherein said microbial spores comprise, consist essentially of, or consist of spores of one or more strains of *Trichoderma*, optionally one or more strains of *T. asperellum, T. afroviride, T. fertile, T. gamsii, T. hamatum, T. harzianum, T. reesi, T. virens* and/or *T. viridae*.

9. The inoculant composition of any one of the preceding paragraphs, wherein said microbial spores comprise, consist essentially of, or consist of spores of one or more mycorrhizal fungi.

10. The inoculant composition of any one of the preceding paragraphs, wherein said microbial spores comprise, consist essentially of, or consist of spores of one or more strains of *Gliocladium*, optionally one or more strains of *Gliocladium virens*, one or more strains of *Glomus*, optionally one or more strains of *Glomus intraradices*, and/or one or more strains of *Metarhizium*, optionally, one or more strains of *Metarhizium anisopliae*.

11. The inoculant composition of any one of the preceding paragraphs, wherein said microbial spores comprise, consist essentially of, or consist of spores of one or more strains of *Bacillus*, optionally *Bacillus amyloliquefaciens* D747, *Bacillus amyloliquefaciens* NRRL B-50349, *Bacillus amyloliquefaciens* TJ1000, *Bacillus amyloliquefaciens* FZB24, *Bacillus amyloliquefaciens* FZB42, *Bacillus amyloliquefaciens* IN937a, *Bacillus amyloliquefaciens* IT-45, *Bacillus amyloliquefaciens* TJ1000, *Bacillus amyloliquefaciens* MBI600, *Bacillus amyloliquefaciens* BS27 (deposited as NRRL B-5015), *Bacillus amyloliquefaciens* BS2084 (deposited as NRRL B-50013), *Bacillus amyloliquefaciens* 15AP4 (deposited as ATCC PTA-6507), *Bacillus amyloliquefaciens* 3AP4 (deposited as ATCC PTA-6506), *Bacillus amyloliquefaciens* LSSA01 (deposited as NRRL B-50104), *Bacillus amyloliquefaciens* ABP278 (deposited as NRRL B-50634), *Bacillus amyloliquefaciens* 1013 (deposited as NRRL B-50509), *Bacillus amyloliquefaciens* 918 (deposited as NRRL B-50508), *Bacillus amyloliquefaciens* 22CP1 (deposited as ATCC PTA-6508) and *Bacillus amyloliquefaciens* BS18 (deposited as NRRL B-50633), *Bacillus cereus* 1-1562, *Bacillus firmus* 1-1582, *Bacillus licheniformis* BA842 (deposited as NRRL B-50516), *Bacillus licheniformis* BL21 (deposited as NRRL B-50134), *Bacillus mycoides* NRRL B-21664, *Bacillus pumilus* NRRL B-21662, *Bacillus pumilus* NRRL B-30087, *Bacillus pumilus* ATCC 55608, *Bacillus pumilus* ATCC 55609, *Bacillus pumilus* GB34, *Bacillus pumilus* KFP9F, *Bacillus pumilus* QST 2808, *Bacillus subtilis* ATCC 55078, *Bacillus subtilis* ATCC 55079, *Bacillus subtilis* MBI 600, *Bacillus subtilis* NRRL B-21661, *Bacillus subtilis* NRRL B-21665, *Bacillus subtilis* CX-9060, *Bacillus subtilis* GB03, *Bacillus subtilis* GB07, *Bacillus subtilis* QST-713, *Bacillus subtilis* FZB24, *Bacillus subtilis* D747, *Bacillus subtilis* 3BP5 (deposited as NRRL B-50510), *Bacillus thuringiensis* ATCC 13367, *Bacillus thuringiensis* GC-91, *Bacillus thuringiensis* NRRL B-21619, *Bacillus thuringiensis* ABTS-1857, *Bacillus thuringiensis* SAN 401 I, *Bacillus thuringiensis* ABG-6305, *Bacillus thuringiensis* ABG-6346, *Bacillus thuringiensis* AM65-52, *Bacillus thuringiensis* SA-12, *Bacillus thuringiensis* SB4, *Bacillus thuringiensis* ABTS-351, *Bacillus thuringiensis* HD-1, *Bacillus thuringiensis* EG 2348, *Bacillus thuringiensis* EG 7826, *Bacillus thuringiensis* EG 7841, *Bacillus thuringiensis* DSM 2803, *Bacillus thuringiensis* NB-125 and/or *Bacillus thuringiensis* NB-176.

12. The inoculant composition of any one of the preceding paragraphs, wherein said microbial spores comprise, consist essentially of, or consist of spores of one or more strains of *Gliocladium*, optionally *Gliocladium virens* ATCC 52045 and/or *Gliocladium virens* GL-21, one or more strains of *Glomus*, optionally *Glomus intraradices* RTI-801, one or more strains of *Metarhizium*, optionally *Metarhizium anisopliae* F52, *Penicillium*, optionally *Penicillium bilaiae* ATCC 18309, *Penicillium bilaiae* ATCC 20851, *Penicillium bilaiae* ATCC 22348, *Penicillium bilaiae* NRRL 50162, *Penicillium bilaiae* NRRL 50169, *Penicillium bilaiae* NRRL 50776, *Penicillium bilaiae* NRRL 50777, *Penicillium bilaiae* NRRL 50778, *Penicillium bilaiae* NRRL 50777, *Penicillium bilaiae* NRRL 50778, *Penicillium bilaiae* NRRL 50779, *Penicillium bilaiae* NRRL 50780, *Penicillium bilaiae* NRRL 50781, *Penicillium bilaiae* NRRL 50782, *Penicillium bilaiae* NRRL 50783, *Penicillium bilaiae* NRRL 50784, *Penicillium bilaiae* NRRL 50785, *Penicillium bilaiae* NRRL 50786, *Penicillium bilaiae* NRRL 50787, *Penicillium bilaiae* NRRL 50788, *Penicillium bilaiae* RS7B-SD1, *Penicillium brevicompactum* AgRF18, *Penicillium canescens* ATCC 10419, *Penicillium expansum* ATCC 24692, *Penicillium expansum* YT02, *Penicillium* fellatanum ATCC 48694, *Penicillium* gaestrivorus NRRL 50170, *Penicillium glabrum* DAOM 239074, *Penicillium glabrum* CBS 229.28, *Penicillium janthinellum* ATCC 10455, *Penicillium lanosocoeruleum* ATCC 48919, *Penicillium radicum* ATCC 201836, *Penicillium radicum* FRR 4717, *Penicillium radicum* FRR 4719, *Penicillium radicum* N93/47267 and/or *Penicillium raistrickii* ATCC 10490, and/or one or more strains of *Trichoderma*, optionally *Trichoderma asperellum* SKT-1, *Trichoderma asperellum* ICC 012, *Trichoderma atroviride* LC52, *Trichoderma atroviride* CNCM 1-1237, *Trichoderma fertile* JM41R, *Trichoderma gamsii* ICC 080, *Trichoderma hamatum* ATCC 52198, *Trichoderma harzianum* ATCC 52445, *Trichoderma harzianum* KRL-AG2, *Trichoderma harzianum* T-22, *Trichoderma harzianum* TH-35, *Trichoderma harzianum* T-39, *Trichoderma harzianum* ICC012, *Trichoderma reesi* ATCC 28217, *Trichoderma virens* ATCC 57678, *Trichoderma virens* G1-3, *Trichoderma virens* GL-21, *Trichoderma virens* G-41, *Trichoderma viridae* ATCC 52440, *Trichoderma viridae* ICC080 and/or *Trichoderma viridae* TV1.

13. The inoculant composition of any one of the preceding paragraphs, wherein said microbial spores comprise, consist essentially of, or consist of spores of one or more strains having a genomic sequence that is at least 75, 80, 85, 90, 95, 96, 97, 98, 99% or more identical to any of the strains recited in paragraph 12 on the basis of 16S rDNA sequence identity.

14. The inoculant composition of any one of the preceding paragraphs, wherein said microbial spores comprise, consist essentially of, or consist of spores of one or more strains having a genomic sequence that is at least 75, 80, 85, 90, 95, 96, 97, 98, 99% or more identical to any of the strains recited in paragraph 13 on the basis of 16S rDNA, internal transcribed spacer (ITS) and/or cytochrome c oxidase (CO1) sequence identity.

15. The inoculant composition of any one of the preceding paragraphs, wherein said microbial spores comprises, consists essentially of, or consist of spores of one or more biopesticides, optionally one or more biofungicides, one or more bioinsecticides and/or one or more bionematicides.

16. The inoculant composition of any one of the preceding paragraphs, wherein said non-aqueous carrier comprises about 70 to about 99% (by weight) of said inoculant composition, optionally about 75 to about 95% (by weight) of said composition, optionally about 80, 80.5, 81, 81.5, 82, 82.5, 83, 83.5, 84, 84.5, 85, 85.5, 86, 86.5, 87, 87.5, 88, 88.5, 89, 89.5 or 90% (by weight) of said inoculant composition.

17. The inoculant composition of any one of the preceding paragraphs, wherein said non-aqueous carrier comprises, consists essentially of or consists of a solid non-aqueous carrier.

18. The inoculant composition of any one of the preceding paragraphs, wherein said non-aqueous carrier comprises less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5% water by weight, based upon the total weight of the composition.

19. The inoculant composition of any one of the preceding paragraphs, wherein said non-aqueous carrier comprises no water.

20. The inoculant composition of any one of the preceding paragraphs, wherein said non-aqueous carrier comprise, consist essentially of or consists of a seed- and/or soil-compatible carrier.

21. The inoculant composition of any one of the preceding paragraphs, wherein said non-aqueous carrier comprises, consists essentially of, or consists of one or more maltodextrins having a dextrose equivalent value of about 3, 4, 5, 6, 7, 8, 9, 10, 11, 12, 13, 14, 15, 16, 17, 18, 19, 20, 21 22, 23, 24 or 25.

22. The inoculant composition of paragraph 1, wherein said non-aqueous carrier comprises, consists essentially of, or consists of one or more maltodextrins having a dextrose equivalent value of about 10 to about 25, optionally about 15 to about 20.

23. The inoculant composition of any one of paragraphs 21-22, wherein said one or more maltodextrins comprise about 5 to about 95% (by weight), optionally about 50 to about 95%, about 55% to about 90%, about 60% to about 85%, about 65% to about 80%, or about 70 to about 80% (by weight), of said inoculant composition.

24. The inoculant composition of any one of paragraphs 21-23, wherein said one or more maltodextrins is present in an amount sufficient to ensure that at least about 0.1, 0.5, 1, 2, 3, 4, 5, 10, 15, 20, 25, 30, 35, 40, 45, 50, 55, 60, 65, 70, 75, 80, 85, 90, 95% or more of said one or more microbial spores remain viable when said inoculant composition is desiccated by about 5, 10, 15, 20, 25, 30, 35, 40, 45, 50, 55, 60, 65, 70, 75, 80, 85, 90, 95% or more.

25. The inoculant composition of any one of paragraphs 21-24, wherein said one or more maltodextrins is present in an amount sufficient to ensure that at least about 0.1, 0.5, 1, 2, 3, 4, 5, 10, 15, 20, 25, 30, 35, 40, 45, 50, 55, 60, 65, 70, 75, 80, 85, 90, 95% or more of said one or more microbial spores remain viable when said inoculant composition is desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 or 30° C. and 5, 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

26. The inoculant composition of any one of paragraphs 21-25, wherein said one or more maltodextrins is present in an amount sufficient to ensure that at least about 0.1, 0.5, 1, 2, 3, 4, 5, 10, 15, 20, 25, 30, 35, 40, 45, 50, 55, 60, 65, 70, 75, 80, 85, 90, 95% or more of said one or more microbial spores remain viable when said inoculant composition is coated on a plant propagation material and desiccated by about 5, 10, 15, 20, 25, 30, 35, 40, 45, 50, 55, 60, 65, 70, 75, 80, 85, 90, 95% or more.

27. The inoculant composition of any one of paragraphs 21-26, wherein said one or more maltodextrins is present in an amount sufficient to ensure that at least about 0.1, 0.5, 1, 2, 3, 4, 5, 10, 15, 20, 25, 30, 35, 40, 45, 50, 55, 60, 65, 70, 75, 80, 85, 90, 95% or more of said one or more microbial spores remain viable when said inoculant composition is coated on a plant propagation material, desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 or 30° C. and 5, 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

28. The inoculant composition of any one of paragraphs 21-27, wherein said one or more maltodextrins is present in an amount sufficient to ensure that at least about 0.1, 0.5, 1, 2, 3, 4, 5, 10, 15, 20, 25, 30, 35, 40, 45, 50, 55, 60, 65, 70, 75, 80, 85, 90, 95% or more of said one or more microbial spores remain viable when said inoculant composition is stored at 4, 5, 6, 7, 8, 9, 10, 11, 12, 13, 14, 15, 16, 17, 18, 19, 20, 21, 22, 23, 24, 25, 26, 27, 28, 29 or 30° C. and 5, 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

29. The inoculant composition of any one of paragraphs 21-28, wherein said one or more maltodextrins is present in an amount sufficient to ensure that at least about 0.1, 0.5, 1, 2, 3, 4, 5, 10, 15, 20, 25, 30, 35, 40, 45, 50, 55, 60, 65, 70, 75, 80, 85, 90, 95% or more of said one or more microbial spores remain viable when said inoculant composition is coated on a plant propagation material.

30. The inoculant composition of any one of paragraphs 21-29, wherein said one or more maltodextrins is present in an amount sufficient to ensure that at least about 0.1, 0.5, 1, 2, 3, 4, 5, 10, 15, 20, 25, 30, 35, 40, 45, 50, 55, 60, 65, 70, 75, 80, 85, 90, 95% or more of said one or more microbial spores remain viable when said inoculant composition is coated on a plant propagation material and stored at 4, 5, 6, 7, 8, 9, 10, 11, 12, 13, 14, 15, 16, 17, 18, 19, 20, 21, 22, 23, 24, 25, 26, 27, 28, 29 or 30° C. and 5, 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

31. The inoculant composition of any one of paragraphs 21-30, wherein said one or more maltodextrins is present in an amount sufficient to ensure that at least about $1\times10^1$ to about $1\times10^{15}$ colony-forming units, optionally at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ or more colony-forming units, of said one or more microbial spores per gram and/or milliliter of said inoculant composition remain viable when said inoculant composition is desiccated by about 5, 10, 15, 20, 25, 30, 35, 40, 45, 50, 55, 60, 65, 70, 75, 80, 85, 90, 95% or more.

32. The inoculant composition of any one of paragraphs 21-31, wherein said one or more maltodextrins is present in an amount sufficient to ensure that at least about $1\times10^1$ to about $1\times10^{15}$ colony-forming units, optionally at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ or more colony-forming units, of said one or more microbial spores per gram and/or milliliter of said inoculant composition remain viable when said inoculant composition is desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 or 30° C. and 5, 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

33. The inoculant composition of any one of paragraphs 21-32, wherein said one or more maltodextrins is present in an amount sufficient to ensure that at least about $1\times10^1$ to about $1\times10^{15}$ colony-forming units, optionally at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ or more colony-forming units, of said one or more microbial spores per seed remain viable when said inoculant composition is coated on a seed and desiccated by about 5, 10, 15, 20, 25, 30, 35, 40, 45, 50, 55, 60, 65, 70, 75, 80, 85, 90, 95% or more.

34. The inoculant composition of any one of paragraphs 21-33, wherein said one or more maltodextrins is present in an amount sufficient to ensure that at least about $1\times10^1$ to about $1\times10^{15}$ colony-forming units, optionally at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ or more colony-forming units, of said one or more microbial spores per seed remain viable when said inoculant composition is coated on a seed, desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

35. The inoculant composition of any one of paragraphs 21-34, wherein said one or more maltodextrins is present in an amount sufficient to ensure that at least about $1\times10^1$ to about $1\times10^{15}$ colony-forming units, optionally at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ or more colony-forming units, of said one or more microbial spores per gram and/or milliliter of said inoculant composition remain viable when said inoculant composition is stored at 4, 5, 6, 7, 8, 9, 10, 11, 12, 13, 14, 15, 16, 17, 18, 19, 20, 21, 22, 23, 24, 25, 26, 27, 28, 29 or 30° C. and 5, 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

36. The inoculant composition of any one of paragraphs 21-35, wherein said one or more maltodextrins is present in an amount sufficient to ensure that at least about $1\times10^1$ to about $1\times10^{15}$ colony-forming units, optionally at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ or more colony-forming units, of said one or more microbial spores per seed remain viable when said inoculant composition is coated on a seed.

37. The inoculant composition of any one of paragraphs 21-36, wherein said one or more maltodextrins is present in an amount sufficient to ensure that at least about $1\times10^1$ to about $1\times10^{15}$ colony-forming units, optionally at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ or more colony-forming units, of said one or more microbial spores per seed remain viable when said inoculant composition is coated on a seed and stored at 4, 5, 6, 7, 8, 9, 10, 11, 12, 13, 14, 15, 16, 17, 18, 19, 20, 21, 22, 23, 24, 25, 26, 27, 28, 29 or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

38. The inoculant composition of any one of the preceding paragraphs, wherein said non-aqueous carrier comprises one or more disaccharides, optionally maltose, trehalose, lactose, sucrose and/or cellobiose.

39. The inoculant composition of paragraph 38, wherein said one or more disaccharides comprise about 5, 10, 15, 20, 25, 30, 35, 40, 45, 50, 55, 60, 65, 70, 75, 80, 85, 90% or more (by weight) of said inoculant composition.

40. The inoculant composition of paragraph 38, wherein said one or more disaccharides comprises about 5 to about 90% (by weight), optionally about 1 to about 20%, about 1% to about 15%, about 1% to about 15%, about 5% to about 15%, or about 5 to about 10% (by weight), of said inoculant composition.

41. The inoculant composition of paragraph 38, wherein said one or more disaccharides constitutes about 1, 2, 3, 4, 5, 6, 7, 8, 9, 10, 11, 12, 13, 14, 15, 16, 17, 18, 19, 20, 21, 22, 23, 24, 25% of the said inoculant composition (by weight).

42. The inoculant composition of any one of paragraphs 38 to 41, wherein said one or more maltodextrins and said one or more disaccharides collectively comprise about 5, 10, 15, 20, 25, 30, 35, 40, 45, 50, 55, 60, 65, 70, 75, 80, 85, 90, 95% or more (by weight) of said inoculant composition.

43. The inoculant composition of any one of paragraphs 38 to 41, wherein said one or more maltodextrins and said one or more disaccharides collectively comprise about 5 to about 95% (by weight), optionally about 50 to about 99%, about 55% to about 95%, about 60% to about 90%, about 65% to about 90%, about 70% to about 90%, about 75% to about 90%, or about 80 to about 90% (by weight), of said inoculant composition.

44. The inoculant composition of any one of paragraphs 38 to 41, wherein said one or more maltodextrins and said one or more disaccharides are present in said inoculant composition in a maltodextrin:disaccharide ratio of about 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5 or more, optionally about 70:30, 75:25, 80:20, 85:15, 90:10, 95:5, 96:4, 97:3, 98:2, 99:1 or more.

45. The inoculant composition of any one of paragraphs 1-37, wherein said inoculant composition comprises one or more malt extracts.

46. The inoculant composition of paragraph 45, wherein said one or more malt extracts comprise about 5, 10, 15, 20, 25, 30, 35, 40, 45, 50, 55, 60, 65, 70, 75, 80, 85, 90% or more (by weight) of said inoculant composition.

47. The inoculant composition of paragraph 45, wherein said one or more malt extracts comprises about 5 to about 90% (by weight), optionally about 1 to about 20%, about 1% to about 15%, about 1% to about 15%, about 5% to about 15%, or about 5 to about 10% (by weight), of said inoculant composition.

48. The inoculant composition of paragraph 45, wherein said one or more malt extracts constitutes about 1, 2, 3, 4, 5, 6, 7, 8, 9, 10, 11, 12, 13, 14, 15, 16, 17, 18, 19, 20, 21, 22, 23, 24, 25% of the said inoculant composition (by weight).

49. The inoculant composition of any one of paragraphs 45 to 48, wherein said one or more maltodextrins and said one or more malt extracts collectively comprise about 5, 10, 15, 20, 25, 30, 35, 40, 45, 50, 55, 60, 65, 70, 75, 80, 85, 90, 95% or more (by weight) of said inoculant composition.

50. The inoculant composition of any one of paragraphs 45 to 48, wherein said one or more maltodextrins and said one or more malt extracts collectively comprise about 5 to about 95% (by weight), optionally about 50 to about 99%, about 55% to about 95%, about 60% to about 90%, about 65% to about 90%, about 70% to about 90%, about 75% to about 90%, or about 80 to about 90% (by weight), of said inoculant composition.

51. The inoculant composition of any one of paragraphs 45 to 48, wherein said one or more maltodextrins and said one or more malt extracts are present in said inoculant composition in a maltodextrin:disaccharide ratio of about 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5 or more, optionally about 70:30, 75:25, 80:20, 85:15, 90:10, 95:5, 96:4, 97:3, 98:2, 99:1 or more.

52. The inoculant composition of any one of the preceding paragraphs, wherein said inoculant composition comprises one or more dispersants.

53. The inoculant composition of paragraph 52, wherein said one or more dispersants comprise about 0.1 to about 5% (by weight) of said composition, optionally about 0.1 to about 2% (by weight) of said composition, optionally about 0.1, 0.2, 0.3, 0.4, 0.5, 0.6, 0.7, 0.8, 0.9, 1, 1.5, 2, 2.5, 3, 3.5, 4, 4.5 or 5% (by weight) of said composition.

54. The inoculant composition of any one of paragraphs 52-53, wherein said one or more dispersants comprises:

one or more anionic surfactants, optionally one or more alkyl carboxylates, alkyl sulfates, alkyl ether sulfates, alkyl amido ether sulfates, alkyl aryl polyether sulfates, alkyl aryl sulfates, alkyl aryl sulfonates, alkyl sulfonates, alkyl amide sulfonates, alkyl aryl sulfonates, alkyl benzene sulfonates, alkyl diphenyloxide sulfonate, alpha-olefin sulfonates, alkyl naphthalene sulfonates, paraffin sulfonates, alkyl sulfosuccinates, alkyl ether sulfosuccinates, alkylamide sulfosuccinates, alkyl sulfosuccinamates, alkyl sulfoacetates, alkyl phosphates, alkyl ether phosphates, acyl sarconsinates, acyl isethionates, N-acyl taurates, N-acyl-N-alkyltaurates, benzene sulfonates, cumene sulfonates, dioctyl sodium sulfosuccinate, ethoxylated sulfosuccinates, lignin sulfonates, linear alkylbenzene sulfonates, monoglyceride sulfates, perfluorobutanesulfonate, perfluorooctanesulfonate, phosphate ester, styrene acrylic polymers, toluene sulfonates and/or xylene sulfonates.

one or more cationic surfactants, optionally one or more alkyltrimethylammonium salts, cetylpyridinium chloride, benzalkonium chloride, benzethonium chloride, 5-Bromo-5-nitro-1,3-dioxane, dimethyldioctadecylammonium chloride, cetrimonium bromide, dioctadecyldimethylammonium bromide and/or octenidine dihydrochloride; and/or one or more non-ionic surfactants, optionally one or more alcohol ethoxylates, alkanolamides, alkanolamine condensates, carboxylic acid esters, cetostearyl alcohol, cetyl alcohol, cocamide DEA, dodecyldimethylamine oxides, ethanolamides, ethoxylates of glycerol ester and glycol esters, ethylene oxide polymers, ethylene oxide-propylene oxide copolymers, glucoside alkyl ethers, glycerol alkyl ethers, glycerol esters, glycol alkyl ethers, glycol alkylphenol ethers, glycol esters, monolaurin, pentaethylene glycol monododecyl ethers, poloxamer, polyamines, polyglycerol polyricinoleate, polysorbate, polyoxyethylenated fatty acids, polyoxyethylenated mercaptans, polyoxyethylenated polyoxyproylene glycols, polyoxyethylene glycol sorbitan alkyl esters, polyethylene glycol-polypropylene glycol copolymers, polyoxyethylene glycol octylphenol ethers, polyvinyl pynolidones, sugar-based alkyl polyglycosides, sulfoanylamides, sorbitan fatty acid alcohol ethoxylates, sorbitan fatty acid ester ethoxylates, sorbitan fatty acid ester and/or tertiary acetylenic glycols; and/or one or more wetting agents, optionally one or more naphthalene sulfonates, optionally one or more alkyl naphthalene sulfonates, one or more isopropyl naphthalene sulfonates and/or one or more butyl naphthalene sulfonates.

55. The inoculant composition of any one of paragraphs 52-54, wherein said one or more dispersants comprises one or more polyoxyethylene alkyl ethers, one or more acrylic copolymers, one or more polyoxyethylene sorbitan trioleates and/or one or more secondary alcohol ethoxylates.

56. The inoculant composition of any one of the preceding paragraphs, wherein said inoculant composition comprises one or more dust suppressants, optionally one or more adhesives, glycerin, mineral oils, paraffinic oils, vegetable oils and/or synthetic polymers.

57. The inoculant composition of paragraph 56, wherein said one or more dust suppressants comprises about 0.5 to about 15%, optionally about 1 to about 10%, about 1 to about 5%, about 2 to about 5%, about 2 to about 4% or about 2 to about 3 (by weight) of the inoculant composition.

58. The inoculant composition of any one of the preceding paragraphs, wherein said inoculant composition comprises one or more protectants.

59. The inoculant composition of paragraph 58, wherein said one or more protectants comprise about 0.0001 to about 10% (by weight) of said composition, optionally about 2 to about 6% (by weight) of said composition, optionally about 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 1, 1.5, 2, 2.5, 3, 3.5, 4, 4.5, 5, 5.5, 6, 7, 7.5, 8, 8.5, 9, 9.5 or 10% (by weight) of said composition.

60. The inoculant composition of any one of paragraphs 58-59, wherein said one or more protectants comprises comprises one or more hygroscopic polymers, optionally one or more albumins, alginates, celluloses, gums (e.g., cellulose gum, guar gum, gum arabic, gum combretum, xantham gum), methyl celluloses, nylons, pectins, polyacrylic acids, polycarbonates, polyethylene glycols (PEG), polyethylenimines (PEI), polylactides, polymethylacrylates (PMA), polyurethanes, polyvinyl alcohols (PVA), polyvinylpyrrolidones (PVP), propylene glycols, sodium carboxymethyl celluloses and/or starches.

61. The inoculant composition of any one of paragraphs 58-60, wherein said one or more protectants comprises comprises one or more oxidation control components, optionally one or more antioxidants (e.g., ascorbic acid, ascorbyl palmitate, ascorbyl stearate, calcium ascorbate, one or more carotenoids, lipoic acid, one or more phenolic compounds (e.g., one or more flavonoids, flavones and/or flavonols), potassium ascorbate, sodium ascorbate, one or more thiols (e.g., glutathione, lipoic acid and/or N-acetyl cysteine), one or more tocopherols, one or more tocotrienols, ubiquinone and/or uric acid) and/or one or more oxygen scavengers, optionally ascorbic acid and/or sodium hydrogen carbonate.

62. The inoculant composition of any one of the preceding paragraphs, wherein said inoculant composition comprises one or more pesticides, optionally:

one or more insecticides and/or nematicides, optionally one or more carbamates, diamides, macrocyclic lactones, neonicotinoids, organophosphates, phenylpyrazoles, pyrethrins, spinosyns, synthetic pyrethroids, tetronic acids and/or tetramic acids;

one or more fungicides, optionally one or more aromatic hydrocarbons, benzimidazoles, benzthiadiazole, carboxamides, carboxylic acid amides, morpholines, phenylamides, phosphonates, quinone outside inhibitors, thiazolidines, thiophanates, thiophene carboxamides and/or triazoles; and/or one or more herbicides, optionally one or more acetyl CoA carboxylase (ACCase) inhibitors, acetolactate synthase (ALS) inhibitors, acetohydroxy acid synthase (AHAS) inhibitors, photosystem II inhibitors, photosystem I inhibitors, protoporphyrinogen oxidase (PPO or Protox) inhibitors, carotenoid biosynthesis inhibitors, enolpyruvyl shikimate-3-phosphate (EPSP) synthase inhibitor, glutamine synthetase inhibitor, dihydropteroate synthetase inhibitor, mitosis inhibitors, 4-hydroxyphenyl-pyruvate-dioxygenase (4-HPPD) inhibitors, synthetic auxins, auxin herbicide salts, auxin transport inhibitors, and/or nucleic acid inhibitors.

63. The inoculant composition of any one of the preceding paragraphs, wherein said inoculant composition comprises one more lipo-chitooligosaccharides, optionally one or more lipo-chitooligosaccharides represented by formulas I-IV.

64. The inoculant composition of any one of the preceding paragraphs, wherein said inoculant composition comprises one more lipo-chitooligosaccharides, optionally one or more of the lipo-chitooligosaccharides represented by structures V-XXXIII.

65. The inoculant composition of any one of the preceding paragraphs, wherein said inoculant composition comprises one or more chitooligosaccharides, optionally one or more chitooligosaccharides represented by formulas XXXI-VXXXV.

66. The inoculant composition of any one of the preceding paragraphs, wherein said inoculant composition comprises one or more chitooligosaccharides, optionally one or more chitooligosaccharides represented by structures XXXVI-XXXIX.

67. The inoculant composition of any one of the preceding paragraphs, wherein said inoculant composition comprises one or more chitinous compounds, optionally one or more chitins and/or one or more chitosans.

68. The inoculant composition of any one of the preceding paragraphs, wherein said inoculant composition comprises one or more flavonoids, optionally:

one or more anthocyanidins, optionally cyanidin, delphinidin, malvidin, pelargonidin, peonidin and/or petunidin;

one or more anthoxanthins, optionally one or more flavones, such as apigenin, baicalein, chrysin, 7,8-dihydroxyflavone, diosmin, flavoxate, 6-hydroxyflavone, luteolin, scutellarein, tangeritin and/or wogonin; and/or flavonols, such as amurensin, astragalin, azaleatin, azalein, fisetin, furanoflavonols galangin, gossypetin, 3-hydroxyflavone, hyperoside, icariin, isoquercetin, kaempferide, kaempferitrin, kaempferol, isorhamnetin, morin, myricetin, myricitrin, natsudaidain, pachypodol, pyranoflavonols quercetin, quercitin, rhanmazin, rhamnetin, robinin, rutin, spiraeoside, troxerutin and/or zanthorhamnin;

one or more flavanones, optionally butin, eriodictyol, hesperetin, hesperidin, homoeriodictyol, isosakuranetin, naringenin, naringin, pinocembrin, poncirin, sakuranetin, sakuranin and/or sterubin;

one or more flavanonols, optionally dihydrokaempferol and/or taxifolin; flavans, such as flavan-3-ols (e.g., catechin (C), catechin 3-gallate (Cg), epicatechins (EC), epigallocatechin (EGC) epicatechin 3-gallate (ECg), epigallcatechin 3-gallate (EGCg), epiafzelechin, fisetinidol, gallocatechin (GC), gallcatechin 3-gallate (GCg), guibourtinidol, mesquitol, robinetinidol, theaflavin-3-gallate, theaflavin-3'-gallate, theflavin-3,3'-digallate, thearubigin), flavan-4-ols (e.g., apiforol and/or luteoforol) and/or flavan-3,4-diols (e.g., leucocyanidin, leucodelphinidin, leucofisetinidin, leucomalvidin, luecopelargonidin, leucopeonidin, leucorobinetinidin, melacacidin and/or teracacidin); and/or one or more isoflavonoids, optionally one or more isoflavones, such as biochanin A, daidzein, formononetin, genistein and/or glycitein; isoflavanes, such as equol, ionchocarpane and/or laxifloorane; isoflavandiols; isoflavenes, such asglabrene, haginin D and/or 2-methoxyjudaicin; coumestans, such as coumestrol, plicadin and/or wedelolactone; pterocarpans; and/or roetonoids; and/or one or more neoflavonoids, optionally calophyllolide, coutareagenin, dalbergichromene, dalbergin and/or nivetin; and/or one or more pterocarpans, optionally bitucarpin A, bitucarpin B, erybraedin A, erybraedin B, erythrabyssin II, erthyrabissin-1, erycristagallin, glycinol, glyceollidins, glyceollins, glycyrrhizol, maackiain, medicarpin, morisianine, orientanol, phaseolin, pisatin, striatine and/or trifolirhizin.

69. The inoculant composition of any one of the preceding paragraphs, wherein said inoculant composition comprises jasmonic acid and/or one or more derivatives thereof.

70. The inoculant composition of any one of the preceding paragraphs, wherein said inoculant composition comprises linoleic acid and/or one or more derivatives thereof.

71. The inoculant composition of any one of the preceding paragraphs, wherein said inoculant composition comprises linolenic acid and/or one or more derivatives thereof.

72. The inoculant composition of any one of the preceding paragraphs, wherein said inoculant composition comprises one or more karrakins, optionally one or more karrakins represented by formula XXXX.

73. The inoculant composition of any one of the preceding paragraphs, wherein said inoculant composition comprises gluconolactone.

74. The inoculant composition of any one of the preceding paragraphs, wherein said inoculant composition comprises one or more drying agents, optionally calcium stearate, one or more clays, graphite, magnesium stearate, magnesium sulfate, powdered milk, one or more silica powders, soy lecithin and/or talc.

75. The inoculant composition of any one of the preceding paragraphs, wherein said inoculant composition comprises one or more biostimulants, optionally one or more seaweed extracts, one or more humic acids, one or more fulvic acids, myo-inositol and/or glycine.

76. The inoculant composition of any one of the preceding paragraphs, wherein said inoculant composition comprises one or more microbial extracts, optionally one or more extracts from media comprising one or more diazotrophic, phosphosphate-solubilizing and/or biopesticidal microorganisms.

77. The inoculant composition of any one of the preceding paragraphs, wherein said inoculant composition comprises one or more nutrients, optionally one or more vitamins (e.g., vitamin A, vitamin B complex (i.e., vitamin $B_1$, vitamin $B_2$, vitamin $B_3$, vitamin $B_5$, vitamin $B_6$, vitamin $B_7$, vitamin $B_8$, vitamin $B_9$, vitamin $B_{12}$, choline) vitamin C, vitamin D, vitamin E, vitamin K, carotenoids ($\alpha$-carotene, $\beta$-carotene, cryptoxanthin, lutein, lycopene and/or zeaxanthin), macrominerals (e.g., calcium, iron, magnesium, nitrogen, phosphorous, potassium and/or sodium), trace minerals (e.g., boron, cobalt, chloride, chromium, copper, fluoride, iodine, iron, manganese, molybdenum, selenium and/or zinc) and/or organic acids (e.g., acetic acid, citric acid, lactic acid, malic acid and/or taurine).

78. The inoculant composition of any one of the preceding paragraphs, wherein said inoculant composition comprises one or more growth media, optionally YEM media, mannitol yeast extract, glycerol yeast extract, Czapek-Dox media and/or potato dextrose broth.

79. The inoculant composition of any one of the preceding paragraphs, wherein said inoculant composition comprises one or more agriculturally acceptable anti-freezing agents, optionally ethylene glycol, glycerin, propylene glycol and/or urea.

80. The inoculant composition of any one of the preceding paragraphs, wherein said inoculant composition comprises a trace amount of water.

81. The inoculant composition of any one of the preceding paragraphs, wherein said inoculant composition comprises, consists essentially of or is a solid.

82. The inoculant composition of any one of the preceding paragraphs, wherein said inoculant composition comprises, consists essentially of or is a wettable powder.

83. The inoculant composition of any one of the preceding paragraphs, wherein at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microbial spores remain viable when said inoculant composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 5, 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

84. The inoculant composition of any one of the preceding paragraphs, wherein at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microbial spores remain viable when said inoculant composition is coated on a plant propagation material.

85. The inoculant composition of any one of the preceding paragraphs, wherein at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microbial spores remain viable when said inoculant composition is coated on a plant propagation material and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 5, 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

86. The inoculant composition of any one of the preceding paragraphs, wherein at least about $1 \times 10^1$ to about $1 \times 10^{10}$ colony-forming units of said one or more microbial spores per gram and/or milliliter of said inoculant composition remain viable when said inoculant composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 5, 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more, optionally at least $1 \times 10^4$, $1 \times 10^5$, $1 \times 10^6$, $1 \times 10^7$ or more colony-forming units per gram and/or milliliter of said inoculant composition.

87. The inoculant composition of any one of the preceding paragraphs, wherein at least about $1\times10^1$ to about $1\times10^{10}$ colony-forming units of said one or more microbial spores per seed remain viable when said inoculant composition is coated on a seed and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 5, 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more, optionally $1\times10^4$, $1\times10^5$, $1\times10^6$, $1\times10^7$ or more colony-forming units per seed.

88. A coated plant propagation material, comprising, consisting essentially of, or consisting of:
a plant propagation material; and
a coating that covers at least a portion of an outer surface of said seed, said coating comprising, consisting essentially of, or consisting of the inoculant composition of any one of claims 1-87.

89. The coated plant propagation material paragraph 88, wherein said coating comprises, consists essentially of, or consists of an inner coating layer that comprises said microbial spores and an outer coating layer that is devoid of said microbial spores.

90. The coated plant propagation material of any one of paragraphs 88-89, wherein said coating comprises, consists essentially of or is an amorphous solid.

91. The coated plant propagation material of any one of paragraphs 88-89, wherein said coating comprises, consists essentially of or is a wettable powder.

92. The coated plant propagation material of any one of paragraphs 88-91, wherein said coating comprises about $1\times10^1$ to about $1\times10^{15}$ colony-forming units of said microbial spores, optionally $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ or more colony-forming units.

93. The coated plant propagation material any one of paragraphs 88-92, wherein said plant propagation material is a seed.

94. The coated plant propagation material of paragraph 93, wherein said seed is a monocot seed.

95. The coated plant propagation material of paragraph 93, wherein said seed is a dicot seed.

96. The coated plant propagation material of paragraph 93, wherein said seed is a leguminous seed.

97. The coated plant propagation material of paragraph 93, wherein said seed is a non-leguminous seed.

98. The coated plant propagation material of any one of paragraphs 88-93, wherein said plant propagation material is of the family Amaranthaceae, optionally chard, spinach, sugar beet, or *quinoa*.

99. The coated plant propagation material of any one of paragraphs 88-93, wherein said plant propagation material is of the family Asteraceae, optionally artichoke, asters, chamomile, chicory, chrysanthemums, dahlias, daisies, *echinacea*, goldenrod, guayule, lettuce, marigolds, safflower, sunflowers, or zinnias.

100. The coated plant propagation material of any one of paragraphs 88-93, wherein said plant propagation material is of the family Brassicaceae, optionally arugula, broccoli, bok choy, Brussels sprouts, cabbage, cauliflower, canola, collard greens, daikon, garden cress, horseradish, kale, mustard, radish, rapeseed, rutabaga, turnip, wasabi, watercress, or *Arabidopsis thaliana*.

101. The coated plant propagation material of any one of paragraphs 88-93, wherein said plant propagation material is of the family Cucurbitaceae, optionally cantaloupe, cucumber, honeydew, melon, pumpkin, squash (e.g., acorn squash, butternut squash, summer squash), watermelon, or zucchini.

102. The coated plant propagation material of any one of paragraphs 88-93, wherein said plant propagation material is of the family Fabaceae, optionally alfalfa, beans, carob, clover, guar, lentils, mesquite, peas, peanuts, soybeans, tamarind, tragacanth, or vetch.

103. The coated plant propagation material of any one of paragraphs 88-93, wherein said plant propagation material is of the family Malvaceae, optionally cacao, cotton, durian, hibiscus, kenaf, kola, or okra.

104. The coated plant propagation material of any one of paragraphs 88-93, wherein said plant propagation material is of the family Poaceae, optionally bamboo, barley, corn, fonio, lawn grass (e.g., Bahia grass, Bermudagrass, bluegrass, Buffalograss, Centipede grass, Fescue, or Zoysia), millet, oats, ornamental grasses, rice, lye, sorghum, sugar cane, triticale, or wheat.

105. The coated plant propagation material of any one of paragraphs 88-93, wherein said plant propagation material is of the family Polygonaceae, optionally buckwheat.

106. The coated plant propagation material of any one of paragraphs 88-93, wherein said plant propagation material is of the family Rosaceae, optionally almonds, apples, apricots, blackberry, blueberry, cherries, peaches, plums, quinces, raspberries, roses, or strawberries.

107. The coated plant propagation material of any one of paragraphs 88-93, wherein said plant propagation material is of the family Solanaceae, optionally bell peppers, chili peppers, eggplant, *petunia*, potato, tobacco, or tomato.

108. The coated plant propagation material of any one of paragraphs 88-93, wherein said plant propagation material is of the family Vitaceae, optionally grape.

109. A kit, comprising:
the coated plant propagation material of any one of paragraphs 88-108; and
a container housing said coated plant propagation material.

110. The kit of claim 109, wherein said container reduces the amount of ambient light that reaches said coated plant propagation material by about 5, 10, 15, 20, 25, 30, 35, 40, 45, 50, 55, 60, 65, 70, 75, 80, 85, 90, 95 or 100% when sealed.

111. The kit of any one of paragraphs 109-110, wherein said container reduces the amount of ambient oxygen that reaches said plant propagation material by about 5, 10, 15, 20, 25, 30, 35, 40, 45, 50, 55, 60, 65, 70, 75, 80, 85, 90, 95 or 100% when sealed.

112. The kit of any one of paragraphs 109-111, wherein said container comprises, consists essentially of, or consists of a material having light permeability of less than about 1, 2, 3, 4, 5, 6, 7, 8, 9, 10, 15, 20, 25, 30, 35, 40, 45, 50, 55, 60, 65, 70 or 75%.

113. The kit of any one of paragraphs 109-112, wherein said container comprises, consists essentially of, or consists of a material having an oxygen transmission rate of less than about 5, 10, 15, 20, 25, 30, 35, 40, 45, 50, 60, 70, 80, 90, 100, 125, 150, 175, 200, 225, 250, 275, 300, 325, 350, 375, 400, 425, 450, 475, or 500 cm$^3$/m$^2$·day (as measured in accordance with ASTM D3985).

114. The kit of any one of paragraphs 109-113, wherein said kit further comprises one or more oxygen-absorbing compound, optionally activated carbon, iron powder, sodium chloride, ferrous carbonate, one or more metal halide catalysts and/or sodium hydrogen carbonate.

115. A plant treated with the inoculant composition of any one of paragraphs 1-87.

116. A plant germinated from the coated plant propagation material of any one of paragraphs 88-108.

117. A plant part harvested from the plant of any one of paragraphs 115-116.

118. A processed product produced from the plant part of paragraph 117.

119. A crop comprising, consisting essentially of, or consisting of a plurality of the plant or plant part of any one of paragraphs 115-117.

120. A method, comprising, consisting essentially of, or consisting of:
applying the inoculant composition of any one of paragraphs 1-87 to a plant propagation material.

121. The method of paragraph 120, further comprising planting said plant propagation material in a growth medium, optionally soil.

122. The method of paragraph 121, wherein said plant propagation material is planted in soil in which plants of the same genus were cultivated in at least one of the three years prior to said planting, optionally in each of the one, two or three years immediately preceding said planting.

123. The method of any one of paragraphs 121-122, wherein said inoculant composition is applied to the plant propagation material at the time of planting.

124. The method of any one of paragraphs 121-122, wherein said inoculant composition is applied to the plant propagation material at least 1, 2, 3, 4, 5, 6, 7, 8, 9, 10, 11, 12, 15, 18, 21, 24, 27, 30, 33, 36, 39, 42, 45, 48 hours or more prior to planting.

125. The method of any one of paragraphs 121-122, wherein said inoculant composition is applied to the plant propagation material at least 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more prior to planting.

126. The method of any one of paragraphs 121-122, wherein said inoculant composition is applied to the plant propagation material about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 months or more prior to planting.

127. The method of any one of paragraphs 121-126, wherein said plant propagation material is a seed.

128. The method of any one of paragraphs 121-126, wherein said plant propagation material is a monocot seed.

129. The method of any one of paragraphs 121-126, wherein said plant propagation material is a dicot seed.

130. The method of any one of paragraphs 121-126, wherein said plant propagation material is a leguminous seed.

131. The method of any one of paragraphs 121-126, wherein said plant propagation material is a non-leguminous seed.

132. The method of any one of paragraphs 121-131, wherein said plant propagation material is of the family Amaranthaceae, optionally chard, spinach, sugar beet, or *quinoa*.

133. The method of any one of paragraphs 121-131, wherein said plant propagation material is of the family Asteraceae, optionally artichoke, asters, chamomile, chicory, chrysanthemums, dahlias, daisies, *echinacea*, goldenrod, guayule, lettuce, marigolds, safflower, sunflowers, or zinnias.

134. The method of any one of paragraphs 121-131, wherein said plant propagation material is of the family Brassicaceae, optionally arugula, broccoli, bok choy, Brussels sprouts, cabbage, cauliflower, canola, collard greens, daikon, garden cress, horseradish, kale, mustard, radish, rapeseed, rutabaga, turnip, wasabi, watercress, or *Arabidopsis thaliana*.

135. The method of any one of paragraphs 121-131, wherein said plant propagation material is of the family Cucurbitaceae, optionally cantaloupe, cucumber, honeydew, melon, pumpkin, squash (e.g., acorn squash, butternut squash, summer squash), watermelon, or zucchini.

136. The method of any one of paragraphs 121-131, wherein said plant propagation material is of the family Fabaceae, optionally alfalfa, beans, carob, clover, guar, lentils, mesquite, peas, peanuts, soybeans, tamarind, tragacanth, or vetch.

137. The method of any one of paragraphs 121-131, wherein said plant propagation material is of the family Malvaceae, optionally cacao, cotton, durian, hibiscus, kenaf, kola, or okra.

138. The method of any one of paragraphs 121-131, wherein said plant propagation material is of the family Poaceae, optionally bamboo, barley, corn, fonio, lawn grass (e.g., Bahia grass, Bermudagrass, bluegrass, Buffalograss, Centipede grass, Fescue, or Zoysia), millet, oats, ornamental grasses, rice, lye, sorghum, sugar cane, triticale, or wheat.

139. The method of any one of paragraphs 121-131, wherein said plant propagation material is of the family Polygonaceae, optionally buckwheat.

140. The method of any one of paragraphs 121-131, wherein said plant propagation material is of the family Rosaceae, optionally almonds, apples, apricots, blackberry, blueberry, cherries, peaches, plums, quinces, raspberries, roses, or strawberries.

141. The method of any one of paragraphs 121-131, wherein said plant propagation material is of the family Solanaceae, optionally bell peppers, chili peppers, eggplant, *petunia*, potato, tobacco, or tomato.

142. The method of any one of paragraphs 121-131, wherein plant propagation material seed is of the family Vitaceae, optionally grape.

143. A method comprising, consisting essentially of, or consisting of:
planting the coated plant propagation material of any one of paragraphs 88-108 in a growth medium, optionally soil.

144. The method of any one of paragraphs 121-143, further comprising applying the inoculant composition of any one of paragraphs 1-87 to the plant that grows from the plant propagation material.

145. A method of enhancing the stability and/or survivability of one or more microorganisms in a composition, comprising, consisting essentially of, or consisting of:
adding one or more protectants to said composition.

146. The method of paragraph 145, wherein said one or more protectants comprises, consists essentially of, or consists of:
one or more maltodextrins having a dextrose equivalent value of about 10 to about 25, optionally about 15 to about 20;
one or more hygroscopic polymers, optionally one or more albumins, alginates, celluloses, gums (e.g., cellulose gum, guar gum, gum arabic, gum combretum, xantham gum), methyl celluloses, nylons, pectins, polyacrylic acids, polycarbonates, polyethylene glycols (PEG), polyethylenimines (PEI), polylactides, polymethylacrylates (PMA), polyurethanes, polyvinyl alcohols (PVA), polyvinylpyrrolidones (PVP), propylene glycols, sodium carboxymethyl celluloses and/or starches; and/or oxidation control components, optionally one or more antioxidants (e.g., ascorbic acid, ascorbyl palmitate, ascorbyl stearate, calcium ascorbate, one or more carotenoids, lipoic acid, one or more phenolic compounds (e.g., one or more flavonoids, flavones and/or flavonols), potassium ascorbate, sodium ascorbate, one or more thiols (e.g., glutathione, lipoic acid and/or N-acetyl cysteine), one or more tocopherols, one or more tocotrienols, ubiquinone and/or uric acid) and/or one or more oxygen scavengers, optionally ascorbic acid and/or sodium hydrogen carbonate.

147. The method of any one of paragraphs 145-146, wherein said one or more protectants is added until it comprises about 0.0001 to about 10% (by weight) of said composition, optionally about 2 to about 6% (by weight) of said composition, optionally about 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 1, 1.5, 2, 2.5, 3, 3.5, 4, 4.5, 5, 5.5, 6, 7, 7.5, 8, 8.5, 9, 9.5 or 10% (by weight) of said composition.

148. The method of any one of paragraphs 145-147, wherein said one or more protectants is added in an amount sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said microbial spores remain viable when said inoculant composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

149. The method of any one of paragraphs 145-148, wherein said one or more protectants is added in an amount sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said microbial spores remain viable when said inoculant composition is coated on a plant propagation material.

150. The method of any one of paragraphs 145-149, wherein said one or more protectants is added in an amount sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said microbial spores remain viable when said inoculant composition is coated on a plant propagation material and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

151. The method of any one of paragraphs 145-150, wherein said one or more protectants is added in an amount sufficient to ensure that at least about $1\times10^1$ to about $1\times10^{15}$ colony-forming units of said microbial spores per gram and/or milliliter of said inoculant composition remain viable when said inoculant composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more, optionally at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ or more colony-forming units per gram and/or milliliter of said inoculant composition.

152. The method of any one of paragraphs 145-151, wherein said one or more protectants is added in an amount sufficient to ensure that at least about $1\times10^1$ to about $1\times10^{15}$ colony-forming units of said microbial spores per seed remain viable when said inoculant composition is coated on a seed and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more, optionally $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ or more colony-forming units per seed.

153. The method of any of paragraphs 145-152, further comprising:

adding one or more dispersants to said composition.

154. The method of paragraph 153, wherein said one or more dispersants comprises:

one or more anionic surfactants, optionally one or more alkyl carboxylates, alkyl sulfates, alkyl ether sulfates, alkyl amido ether sulfates, alkyl aryl polyether sulfates, alkyl aryl sulfates, alkyl aryl sulfonates, alkyl sulfonates, alkyl amide sulfonates, alkyl aryl sulfonates, alkyl benzene sulfonates, alkyl diphenyloxide sulfonate, alpha-olefin sulfonates, alkyl naphthalene sulfonates, paraffin sulfonates, alkyl sulfosuccinates, alkyl ether sulfosuccinates, alkylamide sulfosuccinates, alkyl sulfosuccinamates, alkyl sulfoacetates, alkyl phosphates, alkyl ether phosphates, acyl sarconsinates, acyl isethionates, N-acyl taurates, N-acyl-N-alkyltaurates, benzene sulfonates, cumene sulfonates, dioctyl sodium sulfosuccinate, ethoxylated sulfosuccinates, lignin sulfonates, linear alkylbenzene sulfonates, monoglyceride sulfates, perfluorobutanesulfonate, perfluorooctanesulfonate, phosphate ester, styrene acrylic polymers, toluene sulfonates and/or xylene sulfonates.

one or more cationic surfactants, optionally one or more alkyltrimethylammonium salts, cetylpyridinium chloride, benzalkonium chloride, benzethonium chloride, 5-bromo-5-nitro-1,3-dioxane, dimethyldioctadecylammonium chloride, cetrimonium bromide, dioctadecyldimethylammonium bromide and/or octenidine dihydrochloride; and/or one or more non-ionic surfactants, optionally one or more alcohol ethoxylates, alkanolamides, alkanolamine condensates, carboxylic acid esters, cetostearyl alcohol, cetyl alcohol, cocamide DEA, dodecyldimethylamine oxides, ethanolamides, ethoxylates of glycerol ester and glycol esters, ethylene oxide polymers, ethylene oxide-propylene oxide copolymers, glucoside alkyl ethers, glycerol alkyl ethers, glycerol esters, glycol alkyl ethers, glycol alkylphenol ethers, glycol esters, monolaurin, pentaethylene glycol monododecyl ethers, poloxamer, polyamines, polyglycerol polyricinoleate, polysorbate, polyoxyethylenated fatty acids, polyoxyethylenated mercaptans, polyoxyethylenated polyoxyproylene glycols, polyoxyethylene glycol sorbitan alkyl esters, polyethylene glycol-polypropylene glycol copolymers, polyoxyethylene glycol octylphenol ethers, polyvinyl pynolidones, sugar-based alkyl polyglycosides, sulfoanylamides, sorbitan fatty acid alcohol ethoxylates, sorbitan fatty acid ester ethoxylates, sorbitan fatty acid ester and/or tertiary acetylenic glycols; and/or one or more wetting agents, optionally one or more naphthalene sulfonates, optionally one or more alkyl naphthalene sulfonates, one or more isopropyl naphthalene sulfonates and/or one or more butyl naphthalene sulfonates.

155. The inoculant composition of any one of paragraphs 153-154, wherein said one or more dispersants comprises one or more polyoxyethylene alkyl ethers, one or more acrylic copolymers, one or more polyoxyethylene sorbitan trioleates and/or one or more secondary alcohol ethoxylates.

156. The method of any one of claims 145-155, further:
adding one or more non-aqueous microbial extracts to said composition.

157. The method of paragraph 156, wherein said one or more non-aqueous microbial extracts comprises:

one or more *Bacillus* extracts, optionally an extract of media comprising *B. amyloliquefaciens* D747, *B. amyloliquefaciens* NRRL B-50349, *B. amyloliquefaciens* TJ1000, *B. amyloliquefaciens* FZB24, *B. amyloliquefaciens* FZB42, *B. amyloliquefaciens* IN937a, *B. amyloliquefaciens* IT-45, *B. amyloliquefaciens* TJ1000, *B. amyloliquefaciens* MBI600, *B. amyloliquefaciens* BS27 (deposited as NRRL B-5015), *B. amyloliquefaciens* BS2084 (deposited as NRRL B-50013), *B. amyloliquefaciens* 15AP4 (deposited as ATCC PTA-6507), *B. amyloliquefaciens* 3AP4 (deposited as ATCC PTA-6506), *B. amyloliquefaciens* LSSA01 (deposited as NRRL B-50104), *B. amyloliquefaciens* ABP278 (deposited as NRRL B-50634), *B. amyloliquefaciens* 1013 (deposited as NRRL B-50509), *B. amyloliquefaciens* 918 (deposited as NRRL B-50508), *B. amyloliquefaciens* 22CP1 (deposited as ATCC PTA-6508) and *B. amyloliquefaciens* BS18 (deposited as NRRL B-50633), *B. cereus* 1-1562, *B. firmus* 1-1582, *B. lichenformis* BA842 (deposited as NRRL B-50516), *B. lichenformis* BL21 (deposited as NRRL B-50134), *B. mycoides* NRRL B-21664, *B. pumilus* NRRL B-21662, *B. pumilus* NRRL B-30087, *B. pumilus* ATCC 55608, *B. pumilus* ATCC 55609, *B. pumilus* GB34, *B. pumilus* KFP9F, *B. pumilus* QST 2808, *B. subtilis* ATCC 55078, *B. subtilis* ATCC 55079, *B. subtilis* MBI 600, *B. subtilis* NRRL B-21661, *B. subtilis* NRRL B-21665, *B. subtilis* CX-9060, *B. subtilis* GB03, *B. subtilis* GB07, *B. subtilis* QST-713, *B. subtilis* FZB24, *B. subtilis* D747, *B. subtilis* 3BP5 (deposited as NRRL B-50510), *B. thuringiensis* ATCC 13367, *B. thuringiensis* GC-91, *B. thuringiensis* NRRL B-21619, *B. thuringiensis* ABTS-1857, *B. thuringiensis* SAN 401 I, *B. thuringiensis* ABG-6305, *B. thuringiensis* ABG-6346, *B. thuringiensis* AM65-52, *B. thuringiensis* SA-12, *B. thuringiensis* SB4, *B. thuringiensis* ABTS-351, *B. thuringiensis* HD-1, *B. thuringiensis* EG 2348, *B. thuringiensis* EG 7826, *B. thuringiensis* EG 7841, *B. thuringiensis* DSM 2803, *B. thuringiensis* NB-125 and/or *B. thuringiensis* NB-176;

one or more *Bradyrhizobium* extracts, optionally an extract of media comprising *B. elkanii* SEMIA 501, *B. elkanii* SEMIA 587, *B. elkanii* SEMIA 5019, *B. japonicum* NRRL B-50586 (also deposited as NRRL B-59565), *B. japonicum* NRRL B-50587 (also deposited as NRRL B-59566), *B. japonicum* NRRL B-50588 (also deposited as NRRL B-59567), *B. japonicum* NRRL B-50589 (also deposited as NRRL B-59568), *B. japonicum* NRRL B-50590 (also deposited as NRRL B-59569), *B. japonicum* NRRL B-50591 (also deposited as NRRL B-59570), *B. japonicum* NRRL B-50592 (also deposited as NRRL B-59571), *B. japonicum* NRRL B-50593 (also deposited as NRRL B-59572), *B. japonicum* NRRL B-50594 (also deposited as NRRL B-50493), *B. japonicum* NRRL B-50608, *B. japonicum* NRRL B-50609, *B. japonicum* NRRL B-50610, *B. japonicum* NRRL B-50611, *B. japonicum* NRRL B-50612, *B. japonicum* NRRL B-50726, *B. japonicum* NRRL B-50727, *B. japonicum* NRRL B-50728, *B. japonicum* NRRL B-50729, *B. japonicum* NRRL B-50730, *B. japonicum* SEMIA 566, *B. japonicum* SEMIA 5079, *B. japonicum* SEMIA 5080, *B. japonicum* USDA 6, *B. japonicum* USDA 110, *B. japonicum* USDA 122, *B. japonicum* USDA 123, *B. japonicum* USDA 127, *B. japonicum* USDA 129 and/or *B. japonicum* USDA 532C;

one or more *Rhizobium* extracts, optionally an extract of media comprising *R. leguminosarum* 5012A-2;

one or more *Sinorhizobium* extracts, optionally an extract of media comprising *S. fredii* CCBAU114 and/or *S. fredii* USDA 205;

one or more *Penicillium* extracts, optionally an extract of media comprising *P. bilaiae* ATCC 18309, *P. bilaiae* ATCC 20851, *P. bilaiae* ATCC 22348, *P. bilaiae* NRRL 50162, *P. bilaiae* NRRL 50169, *P. bilaiae* NRRL 50776, *P. bilaiae* NRRL 50777, *P. bilaiae* NRRL 50778, *P. bilaiae* NRRL 50777, *P. bilaiae* NRRL 50778, *P. bilaiae* NRRL 50779, *P. bilaiae* NRRL 50780, *P. bilaiae* NRRL 50781, *P. bilaiae* NRRL 50782, *P. bilaiae* NRRL 50783, *P. bilaiae* NRRL 50784, *P. bilaiae* NRRL 50785, *P. bilaiae* NRRL 50786, *P. bilaiae* NRRL 50787, *P. bilaiae* NRRL 50788, *P. bilaiae* RS7B-SD1, *P. brevicompactum* AgRF18, *P. canescens* ATCC 10419, *P. expansum* ATCC 24692, *P. expansum* YT02, *P. fellatanum* ATCC 48694, *P. gaestrivorus* NRRL 50170, *P. glabrum* DAOM 239074, *P. glabrum* CBS 229.28, *P. janthinellum* ATCC 10455, *P. lanosocoeruleum* ATCC 48919, *P. radicum* ATCC 201836, *P. radicum* FRR 4717, *P. radicum* FRR 4719, *P. radicum* N93/47267 and/or *P. raistrickii* ATCC 10490;

one or more Sfreptomyces extracts, optionally an extract of media comprising *Streptomyces* NRRL B-30145, Sfreptomyces M1064, *S. galbus* NRRL 30232, S, *lydicus* WYEC 108 (ATCC 55445), *S. violaceusniger* YCED 9 (ATCC 55660) and/or *Streptomyces* WYE 53 (ATCC 55750); and/or one or more *Trichoderma* extracts, optionally an extract of media comprising *T. asperellum* SKT-1 (ECO-HOPE®, Kumiai Chemical Industry Co., Ltd., Japan), *T. atroviride* LC52 (SENTINEL®, Agrimm Technologies Ltd, NZ), *T. harzianum* T-22 (PLANTSHIELD®, der *Firma* BioWorks Inc., USA), *T. harzianum* TH-35 (ROOT PRO®, from Mycontrol Ltd., Israel); *T. harzianum* T-39 (TRICHODEX®, Mycontrol Ltd., Israel; T. 2000®, Makhteshim Ltd., Israel), *T. harzianum* ICC012 and *T. viride* TRICHOPEL (Agrimm Technologies Ltd, NZ), *T. harzianum* ICC012 and *T. viride* ICC080 (REMEDIER® WP, Isagro Ricerca, Italy), *T. polysporum* and *T. harzianum* (BINAB®, BINAB Bio-Innovation AB, Sweden), T. stromaticum TRICOVAB® (C.E.P.L.A.C., Brazil), *T. virens* GL-21 (SOILGARD®, Certis LLC, USA), *T. virens* G1-3, ATCC 57678, *T. virens* G1-21 (Thermo Trilogy Corporation, Wasco, Calif.), *T. virens* G1-3 and *Bacillus amyloliquefaciens* FZB2, *T. virens* G1-3 and *Bacillus amyloliquefaciens* NRRL B-50349, *T. virens* G1-3 and *Bacillus amyloliquefaciens* TJ1000, *T. virens* G1-21 and *Bacillus amyloliquefaciens* FZB24, *T. virens* G1-21 and *Bacillus amyloliquefaciens* NRRL B-50349, *T. virens* G1-21 and *Bacillus amyloliquefaciens* TJ1000, *T. viride* TRIECO® (Ecosense Labs. (India) Pvt. Ltd., Indien, BIO-CURE® F from T. Stanes & Co. Ltd., Indien), *T. viride* TV1 (Agribiotec srl, Italy), *T. viride* ICC080.

158. The inoculant composition of any one of paragraphs 156-157, wherein said one or more non-aqueous microbial extracts comprises less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5% water by weight, based upon the total weight of the composition.

159. The method of any one of paragraphs 156-158, wherein said one or more non-aqueous microbial extracts is added until it comprises about 0.1 to about 5% (by weight) of said composition, optionally about 0.1 to about 2% (by weight) of said composition, optionally about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% or more (by weight) of said composition.

160. A method, comprising, consisting essentially of or consisting of:
applying the inoculant composition of any one of paragraphs 1-87 to a seed and/or to the plant that grows from said seed;
applying a second composition to said seed and/or to the plant that grows from said seed, said second composition comprising:
one or more agriculturally beneficial microorganisms, optionally one or more diazotrophs, one or more phosphate-solubilizing microorganisms, one or more mycorrhizal fungi and/or one or more biopesticides, optionally one or more biofungicides, one or more bioinsecticides and/or one or more bionematicides;
one or more biostimulants, optionally one or more seaweed extracts, one or more humic acids, one or more fulvic acids, myo-inositol and/or glycine;
one or more nutrients, optionally one or more vitamins (e.g., vitamin A, vitamin B complex (i.e., vitamin B1, vitamin B2, vitamin B3, vitamin B5, vitamin B6, vitamin B7, vitamin B8, vitamin B9, vitamin B12, choline) vitamin C, vitamin D, vitamin E, vitamin K, carotenoids (α-carotene, β-carotene, cryptoxanthin, lutein, lycopene and/or zeaxanthin), macrominerals (e.g., calcium, iron, magnesium, nitrogen, phosphorous, potassium and/or sodium), trace minerals (e.g., boron, cobalt, chloride, chromium, copper, fluoride, iodine, iron, manganese, molybdenum, selenium and/or zinc) and/or organic acids (e.g., acetic acid, citric acid, lactic acid, malic acid and/or taurine);
one or more fungicides, optionally one or more of the fungicides disclosed on pages 31-32 above;
one or more herbicides, optionally one or more of the herbicides disclosed on page 33-34 above;
one or more insecticides, optionally one or more of the insecticides disclosed on page 30 above;
one or more nematicides, optionally one or more of the nematicides disclosed on page 30 above;
one or more lipo-chitooligosaccharides, optionally one or more of the lipo-chitooligosaccharides represented by formulas I—IV and/or one or more of the lipo-chitooligosaccharides represented by structures V-XXXIII
one or more chitooligosaccharides, optionally one or more of the chitooligosaccharides represented by formulas XXXIV-XXXV and/or one or more of the chitooligosaccharides represented by structures XXXVI-XXXIX,
one or more chitinous compounds, optionally one or more chitins and/or one or more chitosans;
one or more flavonoids, optionally one or more anthocyanidins, such as cyanidin, delphinidin, malvidin, pelargonidin, peonidin and/or petunidin; anthoxanthins, such as flavones (e.g., apigenin, baicalein, chrysin, 7,8-dihydroxyflavone, diosmin, flavoxate, 6-hydroxyflavone, luteolin, scutellarein, tangeritin and/or wogonin) and/or flavonols (e.g., amurensin, astragalin, azaleatin, azalein, fisetin, furanoflavonols galangin, gossypetin, 3-hydroxyflavone, hyperoside,icariin, isoquercetin, kaempferide, kaempferitrin, kaempferol, isorhamnetin, morin, myricetin, myricitrin, natsudaidain, pachypodol, pyranoflavonols quercetin, quericitin, rhanmazin, rhamnetin, robinin, rutin, spiraeoside, troxerutin and/or zanthorhamnin); flavanones, such as butin, eriodictyol, hesperetin, hesperidin, homoeriodictyol, isosakuranetin, naringenin, naringin, pinocembrin, poncirin, sakuranetin, sakuranin and/or sterubin; flavanonols, such as dihydrokaempferol and/or taxifolin; flavans, such as flavan-3-ols (e.g., catechin (C), catechin 3-gallate (Cg), epicatechins (EC), epigallocatechin (EGC) epicatechin 3-gallate (ECg), epigallcatechin 3-gallate (EGCg), epiafzelechin, fisetinidol, gallocatechin (GC), gallcatechin 3-gallate (GCg), guibourtinidol, mesquitol, robinetinidol, theaflavin-3-gallate, theaflavin-3'-gallate, theflavin-3,3'-digallate, thearubigin), flavan-4-ols (e.g., apiforol and/or luteoforol) and/or flavan-3,4-diols (e.g., leucocyanidin, leucodelphinidin, leucofisetinidin, leucomalvidin, luecopelargonidin, leucopeonidin, leucorobinetinidin, melacacidin and/or teracacidin); and/or isoflavonoids, such as isoflavones (e.g., biochanin A, daidzein, formononetin, genistein and/or glycitein), isoflavanes (e.g., equol, ionchocarpane and/or laxifloorane), isoflavandiols, isoflavenes (e.g., glabrene, haginin D and/or 2-methoxyjudaicin), coumestans (e.g., coumestrol, plicadin and/or wedelolactone), pterocarpans and/or roetonoids; and/or one or more analogues, derivatives, hydrates, isomers, polymers, salts and solvates thereof, such as neoflavonoids (e.g, calophyllolide, coutareagenin, dalbergichromene, dalbergin and/or nivetin) and/or pterocarpans (e.g., bitucarpin A, bitucarpin B, erybraedin A, erybraedin B, erythrabyssin II, erthyrabissin-1, erycristagallin, glycinol, glyceollidins, glyceollins, glycyrrhizol, maackiain, medicarpin, morisianine, orientanol, phaseolin, pisatin, striatine and/or trifolirhizin);
jasmonic acid and/or one or more derivatives thereof;
linoleic acid and/or one or more derivatives thereof;
linolenic acid and/or one or more derivatives thereof;
one or more karrakins, optionally one or more karrakins represented by formula XXXX;
gluconolactone; and/or
one or more oxidation control components, optionally one or more antioxidants (e.g., ascorbic acid, ascorbyl palmitate, ascorbyl stearate, calcium ascorbate, one or more carotenoids, lipoic acid, one or more phenolic compounds (e.g., one or more flavonoids, flavones and/or flavonols), potassium ascorbate, sodium ascorbate, one or more thiols (e.g., glutathione, lipoic acid and/or N-acetyl cysteine), one or more tocopherols, one or more tocotrienols, ubiquinone and/or uric acid) and/or one or more oxygen scavengers, optionally ascorbic acid and/or sodium hydrogen carbonate.

EXAMPLES

The following examples are not intended to be a detailed catalogue of all the different ways in which the present disclosure may be implemented or of all the features that may be added to the present disclosure. Subjects skilled in the art will appreciate that numerous variations and additions to the various embodiments may be made without departing from the present disclosure. Hence, the following descriptions are intended to illustrate some particular embodiments of the invention and not to exhaustively specify all permutations, combinations and variations thereof.

Example 1

Stable Wettable Powders Comprising *Penicillium* Spores

Solid non-aqueous inoculant compositions of the present disclosure comprising *Penicillium bilaiae* spores (ATCC 20851 and/or RS7B-SD1) were stored for four weeks at 40° C. or for twenty weeks at 20° C. alongside a commercially available wettable powder comprising *Penicillium bilaiae* spores (ATCC 20851 and RS7B-SD1). The survival rate of *Penicillium* spores was greater in each of the solid non-aqueous inoculant compositions of the present disclosure than in the commercially available wettable powder. Table 1.

TABLE 1

| | Inoculant Composition | Viable spores after 20 weeks at 20° C.[1] | Viable spores after 4 weeks at 40° C.[1] |
|---|---|---|---|
| A | *P. bilaiae* spores (10% w/w) + MALTRIN QD ® M580 (74.879% w/w) + maltose monohydrate (8.320% w/w) + MULTIWET MO-85P-PW-(AP) (2.750% w/w) + SUNSPRAY ® 6N (4.051% w/w) | 51% | 11% |
| B | *P. bilaiae* spores (10% w/w) + MALTRIN QD ® M580 (62.40% w/w) + maltose monohydrate (20.80% w/w) + MULTIWET MO-85P-PW-(AP) (2.75% w/w) + SUNSPRAY ® 6N (4.05% w/w) | 54% | 13% |
| C | *P. bilaiae* spores (10% w/w) + MALTRIN QD ® M580 (49.92% w/w) + maltose monohydrate (33.28% w/w) + MULTIWET MO-85P-PW-(AP) (2.5% w/w) + SUNSPRAY ® 6N (4.05% w/w) | 40% | 12% |
| D | *P. bilaiae* spores (10% w/w) + MALTRIN QD ® M580 (52.31% w/w) + maltose monohydrate (34.88% w/w) + BIOSOFT ® N23-3 (2.81% w/w) | 79% | 28% |
| E | *P. bilaiae* spores (10% w/w) + MALTRIN QD ® M580 (65.39% w/w) + maltose monohydrate (21.80% w/w) + BIOSOFT ® N23-3 (2.81% w/w) | 93% | 32% |
| F | *P. bilaiae* spores (10% w/w) + MALTRIN QD ® M580 (78.469% w/w) + maltose monohydrate (8.719% w/w) + BIOSOFT ® N23-3 (2.813% w/w) | 68% | 34% |
| Control | Commercially available wettable powder comprising *P. bilaiae* spores | 52% | 4% |

[1]Expressed as a percentage of the spore content (cfu per gram of inoculant composition) measured at time zero.

The abilities of the aforementioned inoculant compositions to disperse *Penicillium bilaiae* spores are tested by measuring the ease with which each inoculant composition can be mixed into 100 ml of water in a 250 ml Erlenmeyer flask at 130 rpm on an orbital shaker. As a follow up to this qualitative testing, the percentage of single spores (compared to clumps of >2 spores) in each inoculant composition is calculated by observing the spores under a microscope at 200× magnification. Each of the solid non-aqueous inoculant compositions of the present disclosure exhibits greater spore dispersion than the commercially available wettable powder.

Example 2

Stable Wettable Powders Enhance On-Seed Stability

Figure 2:
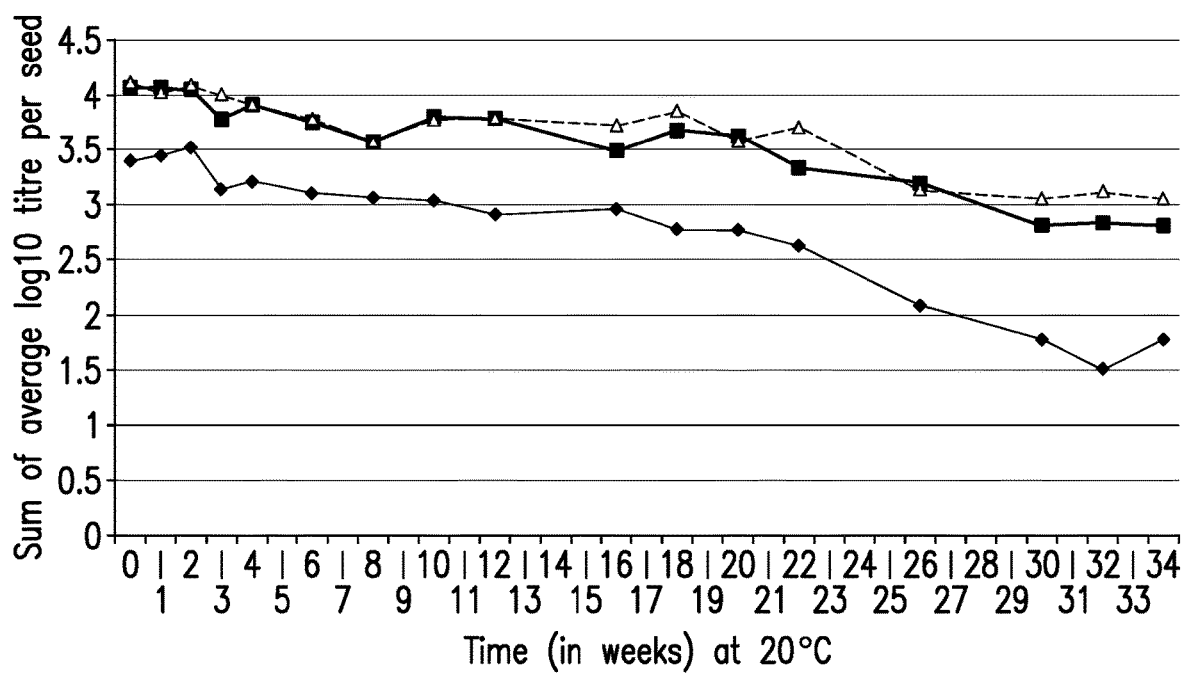
Figure 3:
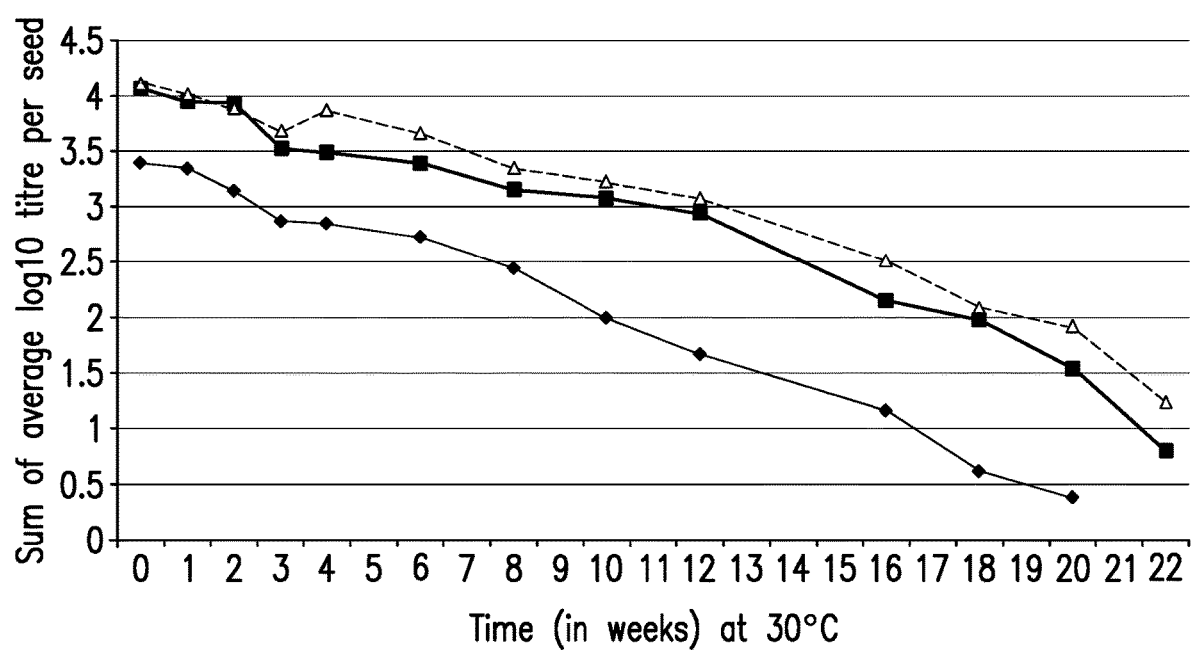

Solid non-aqueous inoculant compositions of the present disclosure comprising spores of *Penicillium bilaiae* and a commercially available wettable powder comprising corresponding spores were coated on corn seeds treated with a commercially available pesticide. The coated seeds were stored at 10, 20 or 30° C. and 50% relative humidity for 1, 2, 3, 4, 6, 8, 10, 12, 16, 18, 20, 22, 26, 30, 32, 34 or 42 weeks and then assayed for on-seed survivability. As indicated in Table 2 and FIGS. 1-3, the survival rate of *Penicillium* spores was greater on seeds coated with the solid non-aqueous inoculant compositions of the present disclosure than on seeds coated with the commercially available wettable powder.

TABLE 2

| | Inoculant Composition | Viable spores after 42 weeks at 10° C.[1] | Viable spores after 20 weeks at 20° C.[1] | Viable spores after 12 weeks at 30° C.[1] |
|---|---|---|---|---|
| F | *P. bilaiae* spores (10% w/w) + MALTRIN QD ® M580 (78.469% w/w) + maltose monohydrate (8.719% w/w) + BIOSOFT ® N23-3 (2.813% w/w) | 8% | 28% | 11% |
| A | *P. bilaiae* spores (10% w/w) + MALTRIN QD ® M580 (74.879% w/w) + maltose monohydrate (8.320% w/w) + MULTIWET MO-85P-PW-(AP) (2.750% w/w) + SUNSPRAY ® 6N (4.051% w/w) | 7% | 23% | 17% |
| Control | Commercially available wettable powder comprising *P. bilaiae* spores | 2% | 14% | 2% |

[1]Expressed as a percentage of the spore content (cfu per seed) measured at time zero.

Example 3

Stable Wettable Powders Enhance On-Seed Stability

Solid non-aqueous inoculant compositions of the present disclosure comprising spores of *Penicillium bilaiae* and a commercially available wettable powder comprising corresponding spores were coated on corn seeds treated with a commercially available pesticide. The coated seeds were stored at 20 or 30° C. and 50% relative humidity for 12 weeks and then assayed for on-seed survivability. As indicated in Table 3, the survival rate of *Penicillium* spores was greater on seeds coated with the solid non-aqueous inoculant compositions of the present disclosure than on seeds coated with the commercially available wettable powder.

TABLE 3

| | Inoculant Composition | Viable spores after 12 weeks at 20° C.[1] | Viable spores after 12 weeks at 30° C.[1] |
|---|---|---|---|
| E | *P. bilaiae* spores (10% w/w) + MALTRIN QD ® M580 (65.39% w/w) + maltose monohydrate (21.80% w/w) + BIOSOFT ® N23-3 (2.81% w/w) | 58% | 8% |

TABLE 3-continued

| | Inoculant Composition | Viable spores after 12 weeks at 20° C.[1] | Viable spores after 12 weeks at 30° C.[1] |
|---|---|---|---|
| D | P. bilaiae spores (10% w/w) + MALTRIN QD ® M580 (52.31% w/w) + maltose monohydrate (34.88% w/w) + BIOSOFT ® N23-3 (2.81% w/w) | 55% | 5% |
| B | P. bilaiae spores (10% w/w) + MALTRIN QD ® M580 (62.40% w/w) + maltose monohydrate (20.80% w/w) + MULTIWET MO-85P-PW-(AP) (2.75% w/w) + SUNSPRAY ® 6N (4.05% w/w) | 38% | 8% |
| C | P. bilaiae spores (10% w/w) + MALTRIN QD ® M580 (49.92% w/w) + maltose monohydrate (33.28% w/w) + MULTIWET MO-85P-PW-(AP) (2.5% w/w) + SUNSPRAY ® 6N (4.05% w/w) | 41% | 6% |
| Control | Commercially available wettable powder comprising P. bilaiae spores | 33% | 2% |

[1]Expressed as a percentage of the spore content (cfu per seed) measured at time zero.

That which is claimed:

1. A non-aqueous inoculant composition comprising microbial spores in a solid non-aqueous carrier that comprises one or more maltodextrins having a dextrose equivalent value of about 15 to about 20 and maltose, said one or more maltodextrins and said maltose comprising about 70 to about 95% w/w (weight by weight) of said inoculant composition based upon the total weight of said inoculant composition said inoculant composition comprising less than 0.5% w/w (weight by weight) water based upon the total weigh of said inoculant composition.

2. The non-aqueous inoculant composition of claim 1, in which said microbial spores comprise one or more agriculturally beneficial microorganisms.

3. The non-aqueous inoculant composition of claim 1, in which said microbial spores comprise about 5 to about 15% w/w of said inoculant composition based upon the total weight of said inoculant composition.

4. The non-aqueous inoculant composition of claim 1, in which said microbial spores are present in a concentration ranging from about $1 \times 10^1$ to about $1 \times 10^{15}$ colony-forming units per gram of said inoculant composition.

5. The non-aqueous inoculant composition of claim 1, in which said microbial spores are present in a concentration ranging from about $1 \times 10^4$ to about $1 \times 10^{11}$ colony-forming units per gram of said inoculant composition.

6. The non-aqueous inoculant composition of claim 1, in which said microbial spores are present at a concentration of at least $1 \times 10^7$ colony-forming units per gram of said inoculant composition.

7. The non-aqueous inoculant composition of claim 1, in which said one or more maltodextrins and said maltose comprise about 75 to about 85% w/w of said inoculant composition based upon the total weight of said inoculant composition.

8. The non-aqueous inoculant composition of claim 1, in which said one or more maltodextrins and said maltose are present in a maltodextrin:maltose ratio of about 15:85 to about 85:15.

9. The non-aqueous inoculant composition of claim 1, in which said one or more maltodextrins and said maltose are present in a maltodextrin:maltose ratio of about 35:65 to about 65:35.

10. The non-aqueous inoculant composition of claim 1, in which the solid non-aqueous carrier further comprises one or more dispersants.

11. The non-aqueous inoculant composition of claim 10, in which said one or more dispersants comprise about 2.5 to about 7.5% w/w of said inoculant composition based upon the total weight of said inoculant composition.

12. A method comprising applying the non-aqueous inoculant composition of claim 1 to a plant or plant part.

13. A method comprising applying the non-aqueous inoculant composition of claim 1 to a plant growth medium.

14. A coated plant seed, comprising:
a plant seed; and
a coating that covers at least a portion of an outer surface of said plant seed,
said coating comprising the non-aqueous inoculant composition of claim 1.

15. A kit comprising a plurality of plant seeds that have been treated with the non-aqueous inoculant composition of claim 1.

* * * * *